US010174302B1

(12) United States Patent
Friedrich et al.

(10) Patent No.: US 10,174,302 B1
(45) Date of Patent: Jan. 8, 2019

(54) MODIFIED L-ASPARAGINASE

(71) Applicants: XL-protein GmbH, Freising (DE); Jazz Pharmaceuticals Ireland Limited, Dublin (IE)

(72) Inventors: Lars Friedrich, Munich (DE); Anne O'Donnell, Dublin (IE)

(73) Assignees: XL-protein GmbH, Freising (DE); Jazz Pharmaceuticals Ireland Limited, Dublin (IE)

( * ) Notice: Subject to any disclaimer, the term of this patent is extended or adjusted under 35 U.S.C. 154(b) by 0 days.

(21) Appl. No.: 15/671,086

(22) Filed: Aug. 7, 2017

Related U.S. Application Data

(60) Provisional application No. 62/523,061, filed on Jun. 21, 2017.

(51) Int. Cl.

| | |
|---|---|
| *C12N 9/82* | (2006.01) |
| *A61K 38/02* | (2006.01) |
| *A61K 38/48* | (2006.01) |
| *C12N 15/00* | (2006.01) |
| *C07K 1/00* | (2006.01) |
| *C07H 21/04* | (2006.01) |
| *C07K 14/00* | (2006.01) |

(52) U.S. Cl.
CPC ............. *C12N 9/82* (2013.01); *A61K 38/02* (2013.01); *A61K 38/48* (2013.01); *C07K 14/00* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 5,286,637 A | 2/1994 | Veronese et al. | |
| 5,359,030 A | 10/1994 | Ekwuribe et al. | |
| 5,681,811 A | 10/1997 | Ekwuribe et al. | |
| 5,932,462 A | 8/1999 | Harris et al. | |
| 6,309,633 B1 | 10/2001 | Ekwuribe et al. | |
| 7,419,660 B1 | 9/2008 | Harris et al. | |
| 7,786,221 B2 | 8/2010 | Harris et al. | |
| 7,829,320 B2 | 11/2010 | Matsui et al. | |
| 7,871,806 B2 | 1/2011 | Matsui et al. | |
| 8,354,477 B2 | 1/2013 | Harris et al. | |
| 9,221,882 B2 * | 12/2015 | Skerra ................. | C07K 7/08 |

(Continued)

FOREIGN PATENT DOCUMENTS

| | | |
|---|---|---|
| WO | 03/018742 A2 | 3/2003 |
| WO | 2011/003633 A1 | 1/2011 |
| WO | 2011/003886 A1 | 1/2011 |

(Continued)

OTHER PUBLICATIONS

Branden et al. Introduction to Protein Structure, Garland Publishing Inc., New York, p. 247, 1991.*

(Continued)

*Primary Examiner* — Yong D Pak
(74) *Attorney, Agent, or Firm* — Morgan, Lewis & Bockius LLP

(57) ABSTRACT

The disclosure provides a modified protein that is a combination of (i) an L-asparaginase and (ii) one or more (poly) peptide(s), wherein the (poly)peptide consists solely of proline and alanine amino acid residues, and methods of preparation and use thereof.

17 Claims, 11 Drawing Sheets

Specification includes a Sequence Listing.

(56) References Cited

U.S. PATENT DOCUMENTS

| | | |
|---|---|---|
| 2012/0100121 A1 | 4/2012 | Abribat |
| 2016/0060613 A1 | 3/2016 | Abribat |

FOREIGN PATENT DOCUMENTS

| | | |
|---|---|---|
| WO | 2011/144756 A1 | 11/2011 |
| WO | 2017/109087 A1 | 6/2017 |

OTHER PUBLICATIONS

Figueiredo. Asparaginase Erwinia Chrysanthemi as a component of a multi-agent chemotherapeutic regimen for the treatment of patients with acute lymphoblastic leukemia who have developed hypersensitivity to *E. coli*-derive Expert Rev Hematol. Mar. 2016;9(3):227-34. doi: 10.1586/17474086.2016.1142370. Epub Feb. 19, 2016.*
P06608. UniProtKB Database. Jun. 8, 2016.*
Billett et al., "Allergic reactions to Erwinia asparaginase in children with acute lymphoblastic leukemia who had previous allergic reactions to *Escherichia coli* asparaginase," Cancer, 70: 201-206 (1992).
Albertsen et al., "Comparison of intramuscular therapy with Erwinia asparaginase and asparaginase Medac: Pharmacokinetics, pharmacodynamics, formation of antibodies and influence on the coagulation system," British Journal of Haematology,115: 983-990 (2001).
Duval et al., "Comparison of *Escherichia coli*-asparaginase with Erwinia-asparaginase in the treatment of childhood lymphoid malignancies: results of a randomized European Organization for Research and Treatment of Cancer—Children's Leukemia Group phase 3 trial," Blood, 99: 2734-2739 (2002).
Roberts et al. "Chemistry for peptide and protein PEGylation," Advanced Drug Delivery Reviews, 54: 459-476 (2002).
Graham, "Pegaspargase: a review of clinical studies," Advanced Drug Delivery Reviews, 55: 1293-1302 (2003).
Sokolov et al., "Design of recombinant L-Asparaginase erwinia carotovora drug with an antitumor action," Molekulyamaya Meditsina, Izdatel'stvo Meditsina, Ru,1: 45-53 (2005)(See English Abstract).
Avramis et al., "Pharmacokinetic/pharmacodynamic relationships of asparaginase formulations: the past, the present and recommendations for the future," Clinical Pharmacokinetics, 44: 367-393 (2005).
Kuchumova et al., "Modification of recombinant asparaginase from Erwinia carotovora with polyethylene glycol 5000," Biochemistry (Moscow) supplemental series B: Biomedical Chemistry,1: 230-232 (2007).
Sartore et al., "Accurate Evaluation Method of the Polymer Content in Monomethoxy (Polyethylene Glycol) Modified Proteins Based on Amino Acid Analysis," Applied Biochemistry and Biotechnology, 31: 213-222 (1991).
Veronese et al., "Improvement of pharmacokinetic, immunological and stability properties of asparaginase by conjugation to linear and branched monomethoxy poly( ethylene glycol)," Journal of Controlled Release, 40: 199-209 (1996).
Oncaspar (pegaspargase) injection for intramuscular or intravenous use, product insert, pp. 1-2, Feb. 1, 1994; Sigma-Tau Pharmaceuticals, Inc., Gaithersburg, Maryland, USA.
Minton et al., "Nucleotide sequence of the Erwinia chrysanthemi NCPPB 1066 L-asparaginase gene," Gene, 46: 25-35 (1986).
Miller et al., "A left-handed crossover involved in amidohydrolase catalysis Crystal structure of Erwinia chrysanthemi L-asparaginase with bound L-aspartate," FEBS Letters, 328: 275-279 (1993).
Keating et al., "L-Asparaginase and PEG Asparaginase—Past, Present, and Future," Leukemia and Lymphoma, 10: 153-157 (1993).
Abshire et al., "Weekly polyethylene glycol conjugated L-asparaginase compared with biweekly dosing produces superior induction remission rates in childhood relapsed acute lymphoblastic leukemia: a pediatric oncology group study," Blood, 96: 1709-1715 (2000).
Fu et al., "PEG-Asparaginase," Expert Opin. Pharmacother, 8: 1977-1984 (2007).
Genbank sequence: CAA31239, Oct. 23, 2008.
Genbank sequence: AAS67028, Jan. 8, 2007.
Park et al., "Pharmacology of *Escherichia coli*-L-Asparaginase Polyethylene Glycol Adduct," Anti-cancer Research, 1: 373-76 (1981).
Chien et al., "Pharmacology, immunogenicity, and efficacy of a novel pegylated recombinant Erwinia chrysanthemi-derived L-asparaginase," Invest. New Drug, 45: 1-16 (2014).
Yang, "PEGylation—Successful Approach for Therapeutic Protein Conjugation," Mod. Chem. Appl.,1: 4-5 (2013).
Third Party Observations submitted in EP App. No. 10730170.7 dated Oct. 21, 2014.
Chunhua et al., "New administration system—conjugate of protein or polypeptide drug and polyethylene glycol," Chinese Pharmacy Journal, 36: 292-293 (2001) (see translated office action issued in Chinese patent application No. 201080030392.6).
Jiahua et al., "Effects of the Lys190 in antigenic epitopes of recombinant *E. coli* L-asparaginase on its antigenicity," Journal of China Pharmaceutical University, 37: 2770-280 (2006).
Office Action issued in Chinese Patent Application No. 201080030392.6 dated Mar. 25, 2013.
International Search Report issued in PCT/EP2010/059599 dated Sep. 20, 2010.
International Preliminary Report on Patentability issued in PCT/EP2010/059599 dated Jan. 10, 2012.
International Search Report issued in PCT/EP2016/082407 dated Mar. 7, 2017.
Written Opinion of the International Authority issued in PCT/EP2016/082407 dated Mar. 7, 2017.
Tang et al., "Production and enhanced biological activity of a novel GHRH analog, hGHRH with an N-terminal Pro-Pro extension," Protein Expression and Purification, 34: 296-301 (2004).
Kim et al., "Application of repeated aspartate tags to improving extracellular production of *Escherichia coli* asparaginase isozyme II," Enzyme and Microbial Technology, 79: 49-54 (2015).
European search report issued in European Patent Application No. 17177237.9 dated Oct. 25, 2017.
Schlapschy et al., "PASylation: a biological alternative to PEGylation for extending the plasma half-life of pharmaceutically active protens," Protein Engineering, Design & Selection, 26: 489-501 (2013).
Morath et al., "PASylation of Murine Leptin Leads to Extended Plasma Half-Life and Enhanced in Vivo Efficacy," Molecular Pharmaceutics, 12: 1431-1442 (2015).
Harari et al., "Enhanced in Vivo Efficacy of a Type I Interferon Superagonist with Extended Plasma Half-life in a Mouse Model of Multiple Sclerosis," Journal of Biological Chemistry, 289: 29014-29029 (2014).
Mendler et al., "High contrast tumor imaging with radio-labeled antibody Fab fragments tailored for optimized pharmacokinetics via PASylation," MABS, 7: 96-109 (2015).

* cited by examiner

Figure 1: Chemistry of the conjugation of Crisantaspase with N-terminally protected P/A peptides via protein amino groups
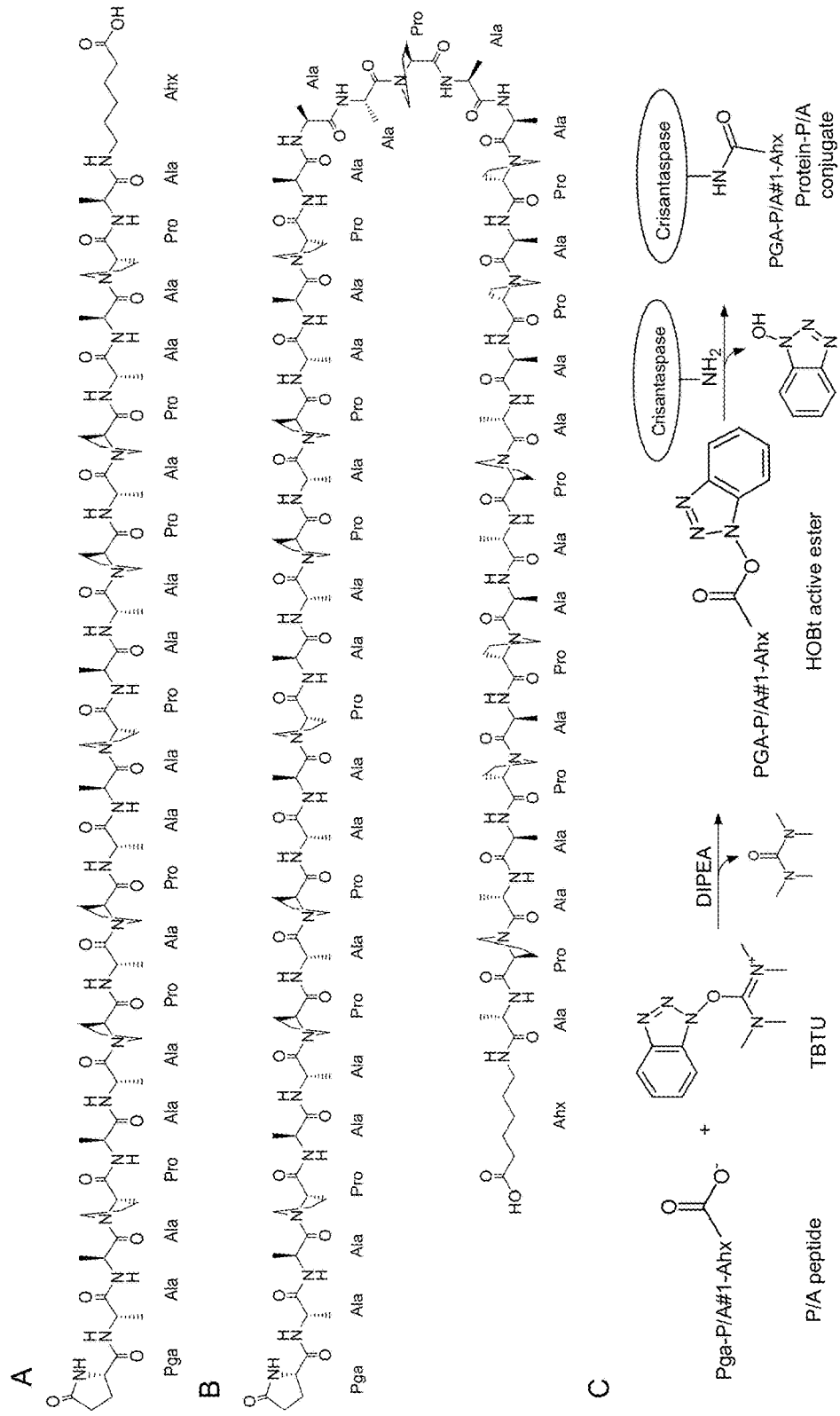

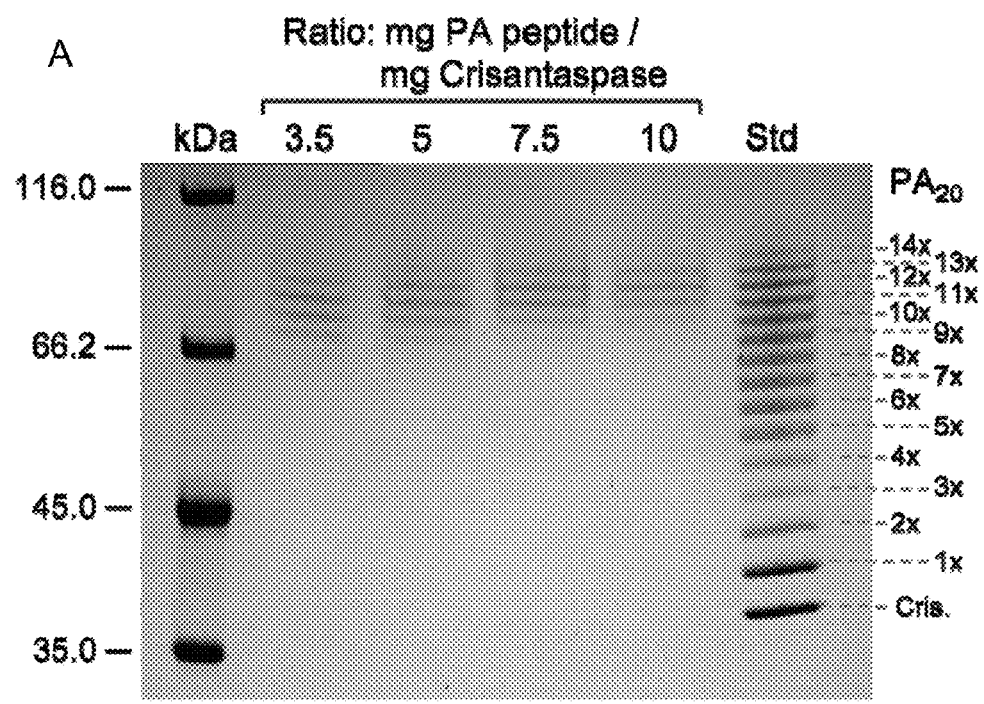
Figure 2: Optimization of Crisantaspase/Pga-P/A(20)-Ahx coupling ratio Figure 3: Purification of Crisantaspase/Pga-P/A(40)-Ahx peptide coupling product via anion exchange chromatography
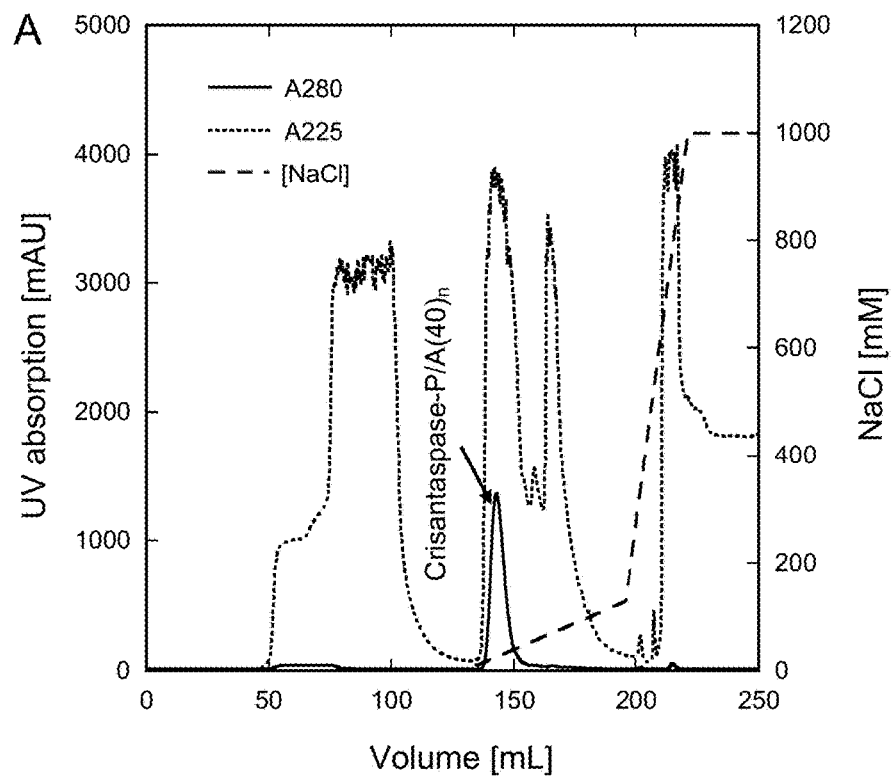
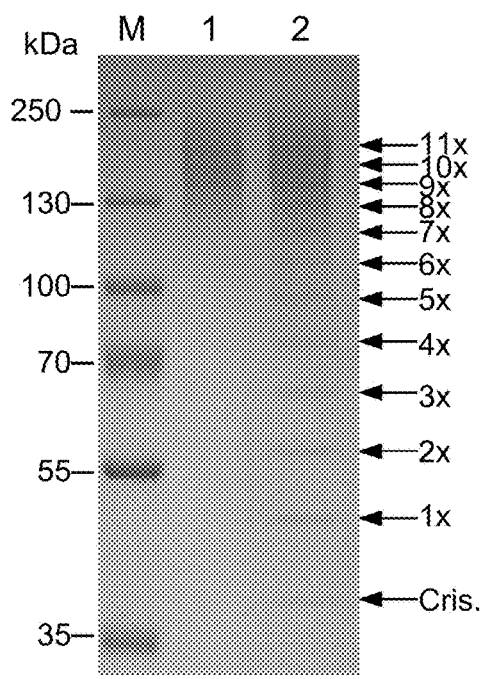

Figure 4: Purification of Crisantaspase/Pga-P/A(20)-Ahx peptide coupling product via anion exchange chromatography
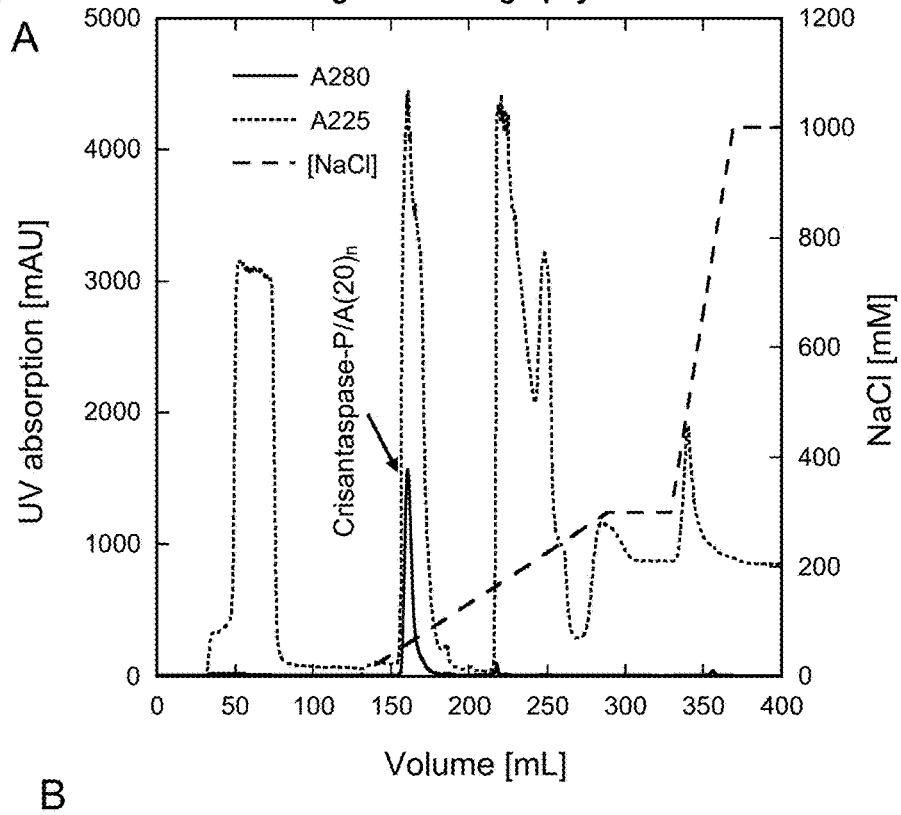
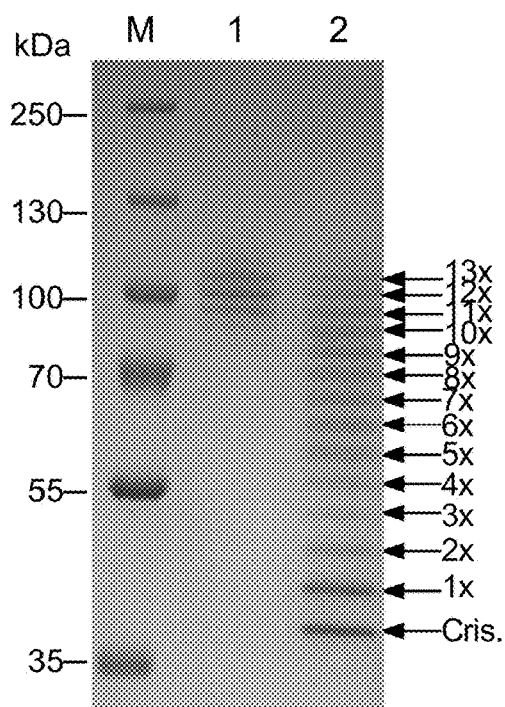

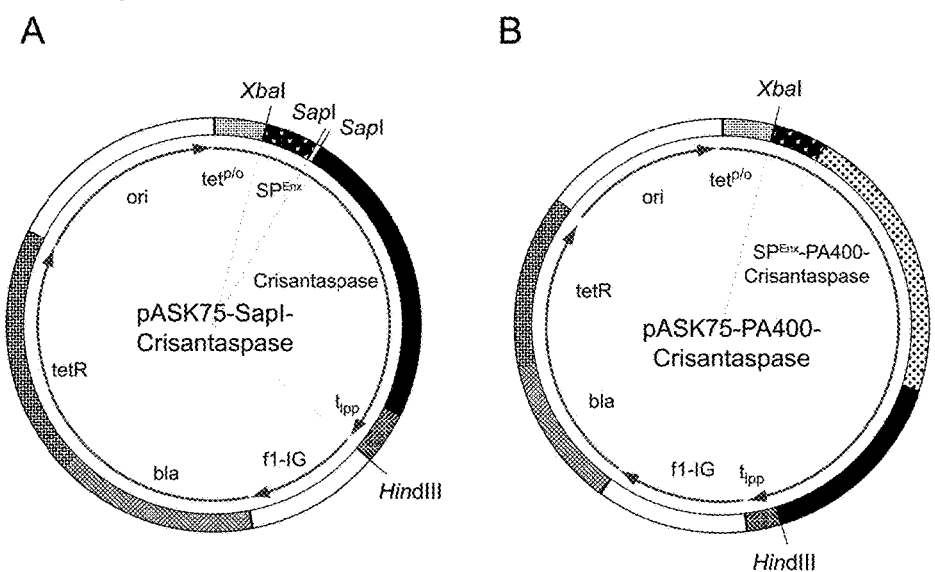
Figure 5: Cloning of the expression vectors for the production of PASylated Crisantaspase in E. coli

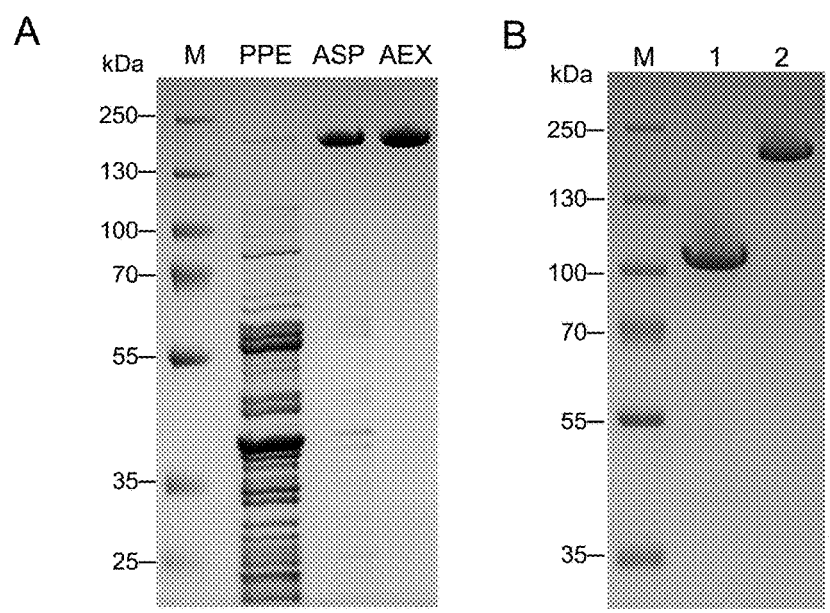
Figure 6: SDS-PGE analysis of recombinant Crisantaspase genetically fused with PA200 or PA400

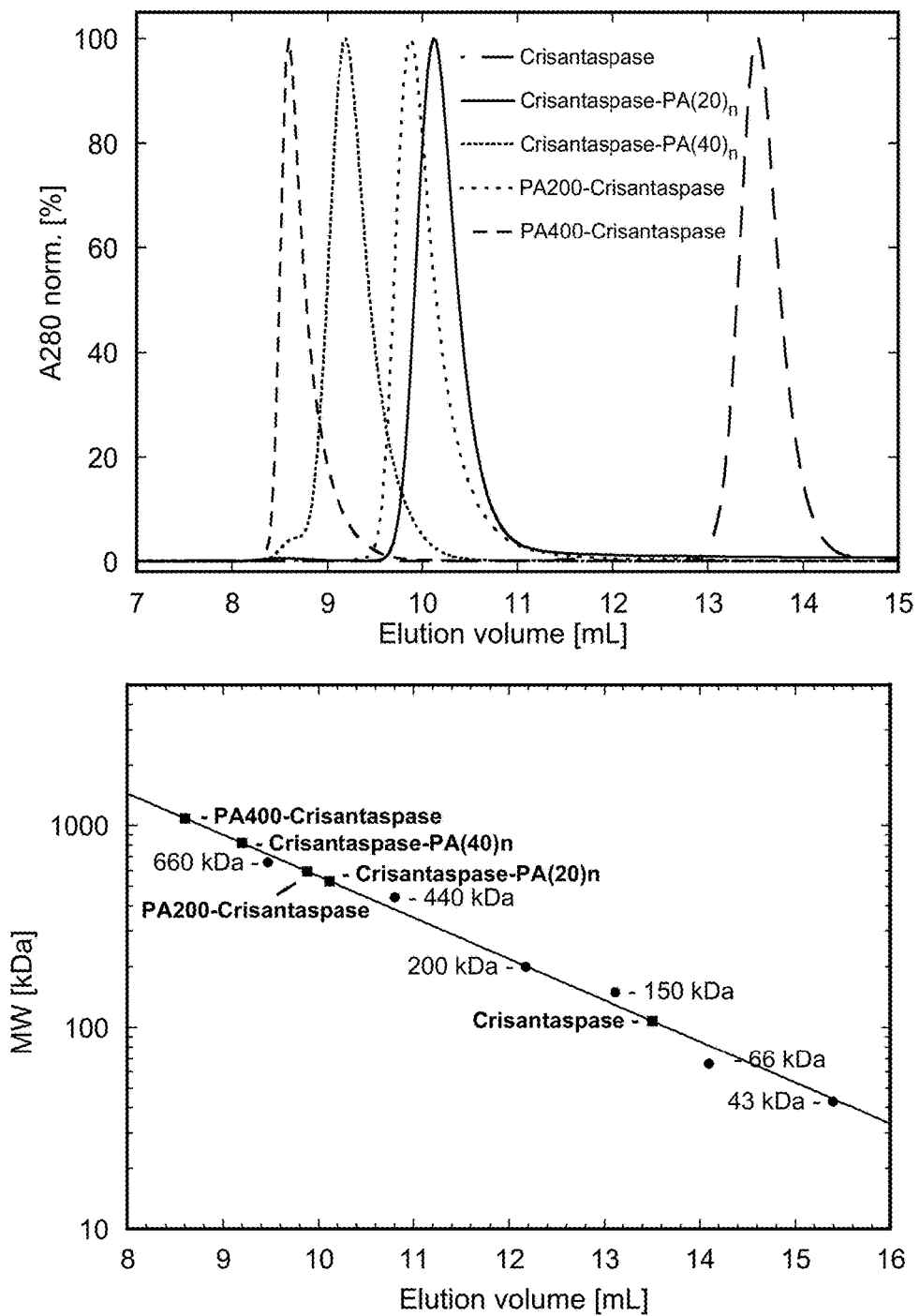
Figure 7: Size exclusion chromatography of PASylated Crisantaspase variants

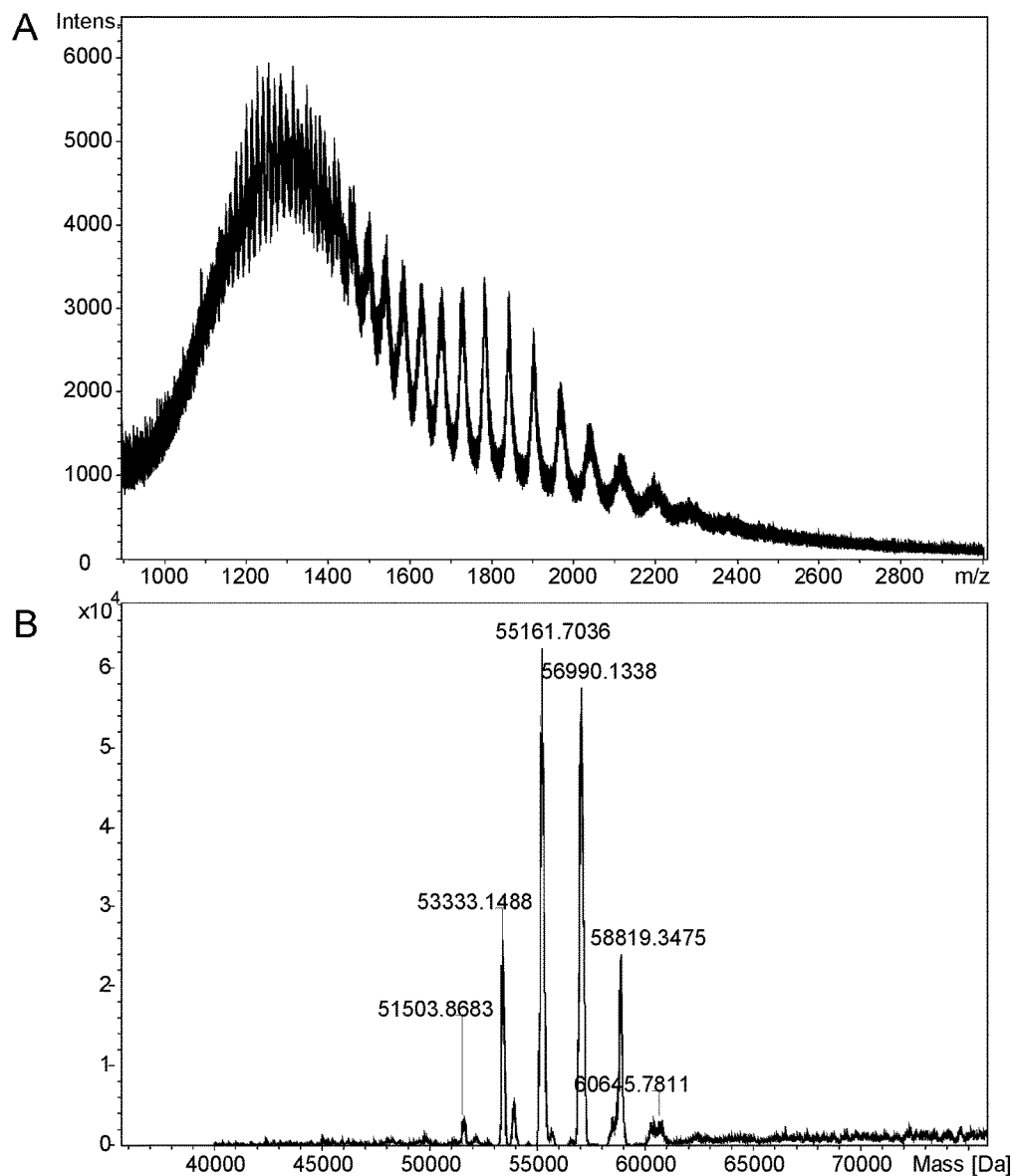
Figure 8: ESI-MS analysis of PASylated Crisantaspase variants

E
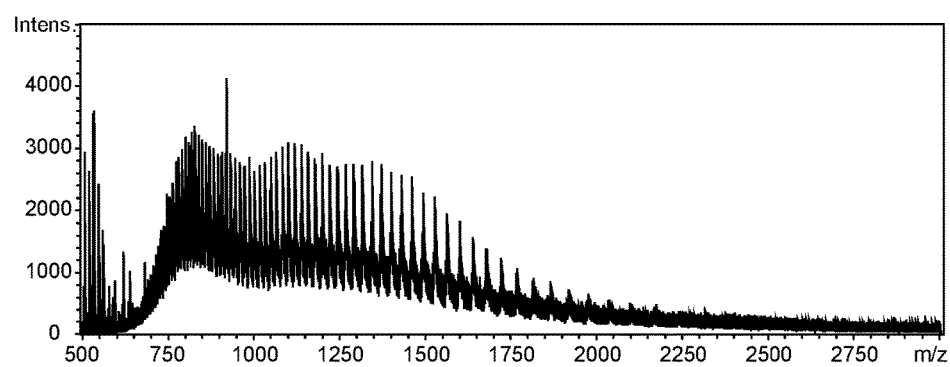
F
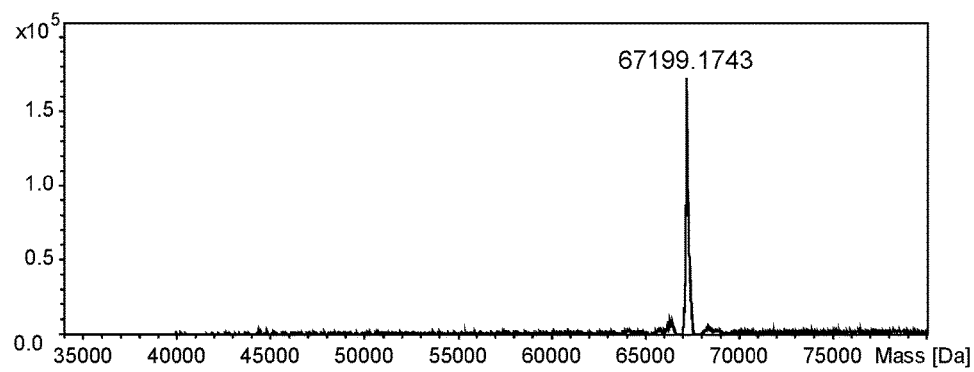
Figure 8 continued

SEQUENCE LISTING

```
<160> NUMBER OF SEQ ID NOS: 17

<210> SEQ ID NO 1
<211> LENGTH: 327
<212> TYPE: PRT
<213> ORGANISM: Dickeya chrysanthemi
<220> FEATURE:
<223> OTHER INFORMATION: L-Asparaginase

<400> SEQUENCE: 1

Ala Asp Lys Leu Pro Asn Ile Val Ile Leu Ala Thr Gly Gly Thr Ile
1               5                   10                  15

Ala Gly Ser Ala Ala Thr Gly Thr Gln Thr Thr Gly Tyr Lys Ala Gly
            20                  25                  30

Ala Leu Gly Val Asp Thr Leu Ile Asn Ala Val Pro Glu Val Lys Lys
        35                  40                  45

Leu Ala Asn Val Lys Gly Glu Gln Phe Ser Asn Met Ala Ser Glu Asn
    50                  55                  60

Met Thr Gly Asp Val Val Leu Lys Leu Ser Gln Arg Val Asn Glu Leu
65                  70                  75                  80

Leu Ala Arg Asp Asp Val Asp Gly Val Val Ile Thr His Gly Thr Asp
                85                  90                  95

Thr Val Glu Glu Ser Ala Tyr Phe Leu His Leu Thr Val Lys Ser Asp
            100                 105                 110

Lys Pro Val Val Phe Val Ala Ala Met Arg Pro Ala Thr Ala Ile Ser
        115                 120                 125

Ala Asp Gly Pro Met Asn Leu Leu Glu Ala Val Arg Val Ala Gly Asp
    130                 135                 140

Lys Gln Ser Arg Gly Arg Gly Val Met Val Val Leu Asn Asp Arg Ile
145                 150                 155                 160

Gly Ser Ala Arg Tyr Ile Thr Lys Thr Asn Ala Ser Thr Leu Asp Thr
                165                 170                 175

Phe Lys Ala Asn Glu Glu Gly Tyr Leu Gly Val Ile Ile Gly Asn Arg
            180                 185                 190

Ile Tyr Tyr Gln Asn Arg Ile Asp Lys Leu His Thr Thr Arg Ser Val
        195                 200                 205

Phe Asp Val Arg Gly Leu Thr Ser Leu Pro Lys Val Asp Ile Leu Tyr
    210                 215                 220

Gly Tyr Gln Asp Asp Pro Glu Tyr Leu Tyr Asp Ala Ala Ile Gln His
225                 230                 235                 240

Gly Val Lys Gly Ile Val Tyr Ala Gly Met Gly Ala Gly Ser Val Ser
                245                 250                 255

Val Arg Gly Ile Ala Gly Met Arg Lys Ala Met Glu Lys Gly Val Val
            260                 265                 270

Val Ile Arg Ser Thr Arg Thr Gly Asn Gly Ile Val Pro Pro Asp Glu
        275                 280                 285

Glu Leu Pro Gly Leu Val Ser Asp Ser Leu Asn Pro Ala His Ala Arg
    290                 295                 300

Ile Leu Leu Met Leu Ala Leu Thr Arg Thr Ser Asp Pro Lys Val Ile
```

```
305                 310                 315                 320
Gln Glu Tyr Phe His Thr Tyr
                325

<210> SEQ ID NO 2
<211> LENGTH: 981
<212> TYPE: DNA
<213> ORGANISM: Dickeya chrysanthemi
<220> FEATURE:
<223> OTHER INFORMATION: L-Asparaginase

<400> SEQUENCE: 2
gcagataaac tgccgaatat tgttattctg gcaaccggtg gcaccattgc aggtagcgca    60
gcaaccggca cccaaaccac aggttataaa gccggtgcac tgggtgttga tacccctgatt  120 aatgcagttc cggaagttaa aaaactggcc aatgtgaaag gtgaacagtt tagcaatatg   180
gccagcgaaa atatgaccgg tgatgttgtt ctgaaactga gccagcgtgt aatgaactg    240 ctggcacgtg atgatgttga tggtgtggtt attacccatg gcaccgatac cgttgaagaa   300
agcgcctatt ttctgcatct gaccgtgaaa agcgataaac cggttgtttt tgttgcagca   360
atgcgtccgg caaccgcaat tagcgcagat ggtccgatga atctgctgga agcagttcgt   420
gttgccggtg ataaacagag ccgtggtcgt ggtgttatgg ttgttctgaa tgatcgtatt   480
ggtagcgcac gctatattac caaaaccaat gcaagcaccc tggatacctt taaagccaat   540
gaagaaggtt atctgggcgt tattattggc aatcgcattt attatcagaa tcgcattgat   600
aaactgcata ccacccgtag cgtttttgat gttcgtggtc tgaccagcct gccgaaagtt   660
gatattctgt atggctatca ggatgatccg gaatatctgt atgatgcagc cattcagcat   720
ggtgttaaag gtattgtgta tgcaggtatg ggtgcaggta gcgttagcgt tcgtggtatt   780
gcaggtatgc gtaaagcaat ggaaaaaggc gttgttgtta ttcgtagcac ccgtaccggt   840
aatggtattg ttccgccgga tgaagaactg ccgggtctgg ttagcgatag cctgaatccg   900
gcacatgcac gtattctgct gatgctggca ctgacccgta ccagcgatcc gaaagtgatt   960
caggaatatt ttcataccta t                                            981

<210> SEQ ID NO 3
<211> LENGTH: 366
<212> TYPE: PRT
<213> ORGANISM: Dickeya chrysanthemi
<220> FEATURE:
<223> OTHER INFORMATION: L-Asparaginase with signal peptide

<400> SEQUENCE: 3

Met Phe Lys Phe Lys Lys Asn Phe Leu Val Gly Leu Ser Ala Ala Leu
1               5                   10                  15

Met Ser Ile Ser Leu Phe Ser Ala Thr Ala Ser Ala Ala Arg Arg Ala
            20                  25                  30

Ile Val Gly Arg Ser Ser Ala Ala Asp Lys Leu Pro Asn Ile Val Ile
        35                  40                  45

Leu Ala Thr Gly Gly Thr Ile Ala Gly Ser Ala Ala Thr Gly Thr Gln
    50                  55                  60

Thr Thr Gly Tyr Lys Ala Gly Ala Leu Gly Val Asp Thr Leu Ile Asn
65                  70                  75                  80

Ala Val Pro Glu Val Lys Lys Leu Ala Asn Val Lys Gly Glu Gln Phe
                85                  90                  95

Ser Asn Met Ala Ser Glu Asn Met Thr Gly Asp Val Val Leu Lys Leu
            100                 105                 110
```

Ser Gln Arg Val Asn Glu Leu Leu Ala Arg Asp Asp Val Asp Gly Val
            115                 120                 125

Val Ile Thr His Gly Thr Asp Thr Val Glu Glu Ser Ala Tyr Phe Leu
    130                 135                 140

His Leu Thr Val Lys Ser Asp Lys Pro Val Val Phe Val Ala Ala Met
145                 150                 155                 160

Arg Pro Ala Thr Ala Ile Ser Ala Asp Gly Pro Met Asn Leu Leu Glu
                165                 170                 175

Ala Val Arg Val Ala Gly Asp Lys Gln Ser Arg Gly Arg Gly Val Met
            180                 185                 190

Val Val Leu Asn Asp Arg Ile Gly Ser Ala Arg Tyr Ile Thr Lys Thr
        195                 200                 205

Asn Ala Ser Thr Leu Asp Thr Phe Lys Ala Asn Glu Glu Gly Tyr Leu
    210                 215                 220

Gly Val Ile Ile Gly Asn Arg Ile Tyr Tyr Gln Asn Arg Ile Asp Lys
225                 230                 235                 240

Leu His Thr Thr Arg Ser Val Phe Asp Val Arg Gly Leu Thr Ser Leu
                245                 250                 255

Pro Lys Val Asp Ile Leu Tyr Gly Tyr Gln Asp Asp Pro Glu Tyr Leu
            260                 265                 270

Tyr Asp Ala Ala Ile Gln His Gly Val Lys Gly Ile Val Tyr Ala Gly
        275                 280                 285

Met Gly Ala Gly Ser Val Ser Val Arg Gly Ile Ala Gly Met Arg Lys
    290                 295                 300

Ala Met Glu Lys Gly Val Val Val Ile Arg Ser Thr Arg Thr Gly Asn
305                 310                 315                 320

Gly Ile Val Pro Pro Asp Glu Glu Leu Pro Gly Leu Val Ser Asp Ser
                325                 330                 335

Leu Asn Pro Ala His Ala Arg Ile Leu Leu Met Leu Ala Leu Thr Arg
            340                 345                 350

Thr Ser Asp Pro Lys Val Ile Gln Glu Tyr Phe His Thr Tyr
        355                 360                 365

<210> SEQ ID NO 4
<211> LENGTH: 1147
<212> TYPE: DNA
<213> ORGANISM: Dickeya chrysanthemi
<220> FEATURE:
<223> OTHER INFORMATION: L-Asparaginase

<400> SEQUENCE: 4
tctagaaata attttgttta actttaagaa ggagatatac atatgttcaa attcaaaaaa    60
aacttcctgg tgggtctgag cgcagcactg atgagcatta gcctgtttag cgcaaccgca   120
agcgcagcca gaagagcgat tgtaggacgc tcttctgccg cagataaact gccgaatatt   180
gttattctgg caaccggtgg caccattgca ggtagcgcag caaccggcac ccagaccacc   240
ggttataaag ccggtgcact gggtgttgat accctgatta atgcagttcc ggaagttaaa   300
aaactggcca atgttaaagg tgagcagttt agcaatatgg ccagcgaaaa tatgaccggt   360
gatgttgttc tgaaactgag ccagcgtgtt aatgaactgc tggcacgtga tgatgttgat   420
ggtgttgtta ttacccatgg caccgatacc gttgaagaaa gcgcatattt tctgcatctg   480
accgtgaaaa gcgataaacc ggttgttttt gttgcagcaa tgcgtccggc aaccgccatt   540
agcgcagatg gtccgatgaa tctgctggaa gcagttcgtg ttgccggtga taaacagagc   600

```
cgtggtcgtg gtgttatggt tgtgctgaat gatcgtattg gtagcgcacg ttatattacc      660
aaaaccaatg caagcaccct ggataccttt aaagcaaatg aagaaggtta tctgggcgtc      720
attattggca atcgtatcta ttatcagaac cgcatcgaca aactgcatac cacccgtagc      780 gttttttgatg ttcgtggtct gaccagcctg ccgaaagtgg atattctgta tggttatcag     840
gatgatccgg aatatctgta tgatgcagca attcagcatg gtgtgaaagg tattgtttat      900
gcaggtatgg gtgcgggtag cgttagcgtt cgtggtattg ccggtatgcg taaagcaatg      960
gaaaaaggtg ttgttgtgat tcgtagcacc cgtaccggta atggtattgt tccgcctgat     1020
gaagaactgc ctggtctggt tagcgatagc ctgaatccgg cacatgcacg tattctgctg     1080
atgctggcac tgacccgtac cagcgatccg aaagttattc aagaatattt tcatacctat     1140
taagctt                                                               1147
```

<210> SEQ ID NO 5
<211> LENGTH: 20
<212> TYPE: PRT
<213> ORGANISM: Artificial Sequence
<220> FEATURE:
<223> OTHER INFORMATION: PA(20) peptide

<400> SEQUENCE: 5

```
Ala Ala Pro Ala Ala Pro Ala Pro Ala Ala Pro Ala Ala Pro Ala Pro
1               5                   10                  15

Ala Ala Pro Ala
            20
```

<210> SEQ ID NO 6
<211> LENGTH: 60
<212> TYPE: DNA
<213> ORGANISM: Artificial Sequence
<220> FEATURE:
<223> OTHER INFORMATION: Nucleotide sequence encoding PA(20) peptide

<400> SEQUENCE: 6

```
gccgcgccag cggccccggc ccctgccgcg cccgctgctc ccgcccctgc tgccccagcc      60
```

<210> SEQ ID NO 7
<211> LENGTH: 201
<212> TYPE: PRT
<213> ORGANISM: Artificial Sequence
<220> FEATURE:
<223> OTHER INFORMATION: PA(200)-polypeptide

<400> SEQUENCE: 7

```
Ala Ala Pro Ala Ala Pro Ala Pro Ala Ala Pro Ala Ala Pro Ala Pro
1               5                   10                  15

Ala Ala Pro Ala Ala Ala Pro Ala Ala Pro Ala Pro Ala Ala Pro Ala
            20                  25                  30

Ala Pro Ala Pro Ala Ala Pro Ala Ala Pro Ala Pro Ala Ala Pro Ala
        35                  40                  45

Ala Ala Pro Ala Ala Pro Ala Pro Ala Ala Pro Ala Ala Pro Ala Pro Ala
    50                  55                  60

Ala Pro Ala Pro Ala Ala Pro Ala Ala Pro Ala Pro Ala Ala Pro Ala
65                  70                  75                  80

Ala Ala Pro Ala Ala Pro Ala Pro Ala Ala Pro Ala Ala Pro Ala Pro
                85                  90                  95

Ala Ala Pro Ala Ala Ala Pro Ala Ala Pro Ala Pro Ala Ala Pro Ala
            100                 105                 110
```

```
Ala Pro Ala Pro Ala Ala Pro Ala Ala Pro Ala Ala Pro Ala Pro
            115                 120                 125

Ala Ala Pro Ala Ala Pro Ala Pro Ala Ala Pro Ala Ala Ala Pro Ala
        130                 135                 140

Ala Pro Ala Pro Ala Ala Pro Ala Ala Pro Ala Ala Pro Ala Pro Ala
145                 150                 155                 160

Ala Ala Pro Ala Ala Pro Ala Pro Ala Ala Pro Ala Ala Pro Ala Pro
            165                 170                 175

Ala Ala Pro Ala Ala Pro Ala Ala Pro Ala Pro Ala Ala Pro Ala
        180                 185                 190

Ala Pro Ala Pro Ala Ala Pro Ala Ala
        195                 200
```

<210> SEQ ID NO 8
<211> LENGTH: 603
<212> TYPE: DNA
<213> ORGANISM: Artificial Sequence
<220> FEATURE:
<223> OTHER INFORMATION: Nucleotide sequence encoding
    PA(200)-polypeptide

<400> SEQUENCE: 8

```
gccgcgccag cggccccggc ccctgccgcg cccgctgctc cgcccctgc tgccccagcc    60
gccgctcctg cggcacctgc gcccgccgcg cggcagcgc cggcaccggc agctccggcg   120
gccgcgcctg cagctcctgc accggcggct ccagcagccc cggcgccggc cgcacctgcg   180
gcggcgcccg cggcgcctgc acccgcagcg cctgcggcac cggccccagc agcccctgcc   240
gccgcaccgg ctgcgcctgc ccagcggcc cccgctgccc cggccccggc ggctccagcc   300
gcagcgcctg ccgccccagc gcccgcagca cggcggcac cagctccggc ggcgccggcg   360
gcggctccgg cagctccggc ccctgctgcg ccggctgcgc cggctccggc ggcccctgcg   420
gcggctccgg ccgcacctgc acctgccgcg ccggctgctc cggccccggc tgccccagca   480
gcggcaccag cagcgcctgc tcctgcggcg cctgcagctc cggcgccggc agccccggcc   540
gccgcacccg cggctccagc ccccgccgct ccagcagccc ccgcgccagc tgcacctgct   600
gcc                                                                603
```

<210> SEQ ID NO 9
<211> LENGTH: 401
<212> TYPE: PRT
<213> ORGANISM: Artificial Sequence
<220> FEATURE:
<223> OTHER INFORMATION: PA(400)-polypeptide

<400> SEQUENCE: 9

```
Ala Ala Pro Ala Ala Pro Ala Pro Ala Ala Pro Ala Ala Pro Ala Pro
1               5                   10                  15

Ala Ala Pro Ala Ala Ala Pro Ala Ala Pro Ala Pro Ala Ala Pro Ala
            20                  25                  30

Ala Pro Ala Pro Ala Ala Pro Ala Ala Pro Ala Pro Ala Ala Pro Ala
        35                  40                  45

Ala Pro Ala Ala Pro Ala Pro Ala Ala Pro Ala Ala Ala Pro Ala
    50                  55                  60

Ala Pro Ala Pro Ala Ala Pro Ala Ala Pro Ala Ala Pro Ala Pro Ala
65                  70                  75                  80

Ala Ala Pro Ala Ala Pro Ala Pro Ala Ala Pro Ala Ala Pro Ala Pro
            85                  90                  95
```

```
Ala Ala Pro Ala Ala Pro Ala Pro Ala Pro Ala Pro Ala
            100                 105                 110

Ala Pro Ala Pro Ala Ala Pro Ala Ala Pro Ala Pro Ala Pro
        115                 120                 125

Ala Ala Pro Ala Ala Pro Ala Pro Ala Ala Pro Ala Ala Pro Ala
    130                 135                 140

Ala Pro Ala Pro Ala Ala Pro Ala Ala Pro Ala Pro Ala Pro Ala
145                 150                 155                 160

Ala Ala Pro Ala Ala Pro Ala Pro Ala Ala Pro Ala Ala Pro
                165                 170                 175

Ala Ala Pro Ala Ala Ala Pro Ala Ala Pro Ala Pro Ala Pro Ala
            180                 185                 190

Ala Pro Ala Pro Ala Ala Pro Ala Ala Pro Ala Pro Ala Pro
        195                 200                 205

Ala Ala Pro Ala Ala Pro Ala Pro Ala Ala Pro Ala Ala Pro Ala
    210                 215                 220

Ala Pro Ala Pro Ala Ala Pro Ala Ala Pro Ala Ala Pro Ala
225                 230                 235                 240

Ala Ala Pro Ala Ala Pro Ala Pro Ala Ala Pro Ala Pro
                245                 250                 255

Ala Ala Pro Ala Ala Ala Pro Ala Ala Pro Ala Pro Ala Pro Ala
            260                 265                 270

Ala Pro Ala Pro Ala Ala Pro Ala Ala Pro Ala Ala Pro Ala Pro
        275                 280                 285

Ala Ala Pro Ala Ala Pro Ala Pro Ala Ala Ala Pro Ala
    290                 295                 300

Ala Pro Ala Pro Ala Ala Pro Ala Pro Ala Ala Pro Ala
305                 310                 315                 320

Ala Ala Pro Ala Ala Pro Ala Pro Ala Ala Pro Ala Pro
                325                 330                 335

Ala Ala Pro Ala Ala Pro Ala Ala Pro Ala Pro Ala Ala Pro Ala
            340                 345                 350

Ala Pro Ala Pro Ala Ala Pro Ala Ala Pro Ala Ala Pro Ala Pro
        355                 360                 365

Ala Ala Pro Ala Ala Pro Ala Pro Ala Ala Pro Ala Ala Ala Pro Ala
    370                 375                 380

Ala Pro Ala Pro Ala Ala Pro Ala Ala Pro Ala Ala Pro Ala
385                 390                 395                 400

Ala
```

<210> SEQ ID NO 10
<211> LENGTH: 1203
<212> TYPE: DNA
<213> ORGANISM: Artificial Sequence
<220> FEATURE:
<223> OTHER INFORMATION: Nucleotide sequence encoding
      PA(400)-polypeptide

<400> SEQUENCE: 10

```
gccgcgccag cggccccggc ccctgccgcg cccgctgctc ccgcccctgc tgccccagcc    60
gccgctcctg cggcacctgc gccgccgcg ccggcagcgc cggcaccggc agctccggcg   120
gccgcgcctg cagctcctgc accggcggct ccagcagccc cggcgccggc cgcacctgcg   180
gcggcgcccg cggcgcctgc acccgcagcg cctgcgcac cggccccagc agcccctgcc   240
gccgcaccgg ctgcgcctgc cccagcggcc cccgctgccc cggcccccggc ggctccagcc   300
```

-continued

```
gcagcgcctg ccgccccagc gcccgcagca ccggcggcac cagctccggc ggcgccggcg      360
gcggctccgg cagctccggc ccctgctgcg ccggctgcgc cggctccggc ggcccctgcg      420
gcggctccgg ccgcacctgc acctgccgcg ccggctgctc cggccccggc tgccccagca      480
gcggcaccag cagcgcctgc tcctgcggcg cctgcagctc cggcgccggc agccccggcc      540
gccgcacccg cggctccagc ccccgccgct ccagcagccc ccgcgccagc tgcacctgct      600
gccgctcctg ctgcccctgc tcccgctgcc ccgccgccc ccgccccagc tgcccccgct       660
gccgcacctg ctgccccagc tcccgctgcc ccagccgcgc cggccccgc agctccagcc       720 gcggcaccag ctgccccagc tccagcggcg cctgctgccc cggccccgc ggcaccggct       780 gccgcgcccg cagctccagc gcctgctgca ccggctgctc cggcacccgc cgcgccagca      840 gctgccctg cggcaccagc tcctgctgcc ccgcggcac ctgcacccgc tgccccggcg        900
gcagctcccg ccgcgccagc ccctgcagct cctgctgcac ctgctcctgc cgcccctgct      960
gctgcccctg ctgctccagc ccctgcagca ccggccgctc cagctcctgc cgctcctgcc     1020
gctgcgcccg ctgctccagc cccagctgcg ccagcagctc ctgcacctgc tgcccctgcc     1080
gccgcccctg cggctccagc acctgctgca ccggccgccc cggcgcccgc tgccccgca      1140 gcagccccag ccgcacccgc tccagcagct cccgcagccc cagcacccgc agcaccagcc     1200
gcc                                                                   1203
```

```
<210> SEQ ID NO 11
<211> LENGTH: 528
<212> TYPE: PRT
<213> ORGANISM: Artificial Sequence
<220> FEATURE:
<223> OTHER INFORMATION: Asparaginase-PA(200)-fusion protein

<400> SEQUENCE: 11

Ala Ala Pro Ala Ala Pro Ala Pro Ala Ala Pro Ala Ala Pro Ala Pro
1               5                   10                  15

Ala Ala Pro Ala Ala Pro Ala Pro Ala Pro Ala Ala Pro Ala
                20                  25                  30

Ala Pro Ala Pro Ala Ala Pro Ala Ala Pro Ala Ala Pro Ala Pro
                35                  40                  45

Ala Ala Pro Ala Ala Pro Pro Ala Ala Pro Ala Ala Ala Pro Ala
        50                  55                  60

Ala Pro Ala Pro Ala Ala Pro Ala Ala Pro Ala Pro Ala Pro Ala
65                  70                  75                  80

Ala Ala Pro Ala Ala Pro Ala Pro Ala Ala Pro Ala Ala Pro Ala Pro
                85                  90                  95

Ala Ala Pro Ala Ala Ala Pro Ala Ala Pro Ala Pro Ala Ala Pro Ala
                100                 105                 110

Ala Pro Ala Pro Ala Ala Pro Ala Ala Pro Ala Ala Pro Ala Pro
                115                 120                 125

Ala Ala Pro Ala Ala Pro Ala Pro Ala Ala Pro Ala Ala Pro Ala
        130                 135                 140

Ala Pro Ala Pro Ala Ala Pro Ala Ala Pro Ala Pro Ala Ala Pro Ala
145                 150                 155                 160

Ala Ala Pro Ala Ala Pro Ala Pro Ala Ala Pro Ala Ala Pro Ala Pro
                165                 170                 175

Ala Ala Pro Ala Ala Ala Pro Ala Ala Pro Ala Pro Ala Ala Pro Ala
                180                 185                 190
```

Ala Pro Ala Pro Ala Ala Pro Ala Ala Asp Lys Leu Pro Asn Ile
        195                 200                 205

Val Ile Leu Ala Thr Gly Gly Thr Ile Ala Gly Ser Ala Ala Thr Gly
    210                 215                 220

Thr Gln Thr Thr Gly Tyr Lys Ala Gly Ala Leu Gly Val Asp Thr Leu
225                 230                 235                 240

Ile Asn Ala Val Pro Glu Val Lys Lys Leu Ala Asn Val Lys Gly Glu
                245                 250                 255

Gln Phe Ser Asn Met Ala Ser Glu Asn Met Thr Gly Asp Val Val Leu
            260                 265                 270

Lys Leu Ser Gln Arg Val Asn Glu Leu Leu Ala Arg Asp Asp Val Asp
        275                 280                 285

Gly Val Val Ile Thr His Gly Thr Asp Thr Val Glu Glu Ser Ala Tyr
    290                 295                 300

Phe Leu His Leu Thr Val Lys Ser Asp Lys Pro Val Val Phe Val Ala
305                 310                 315                 320

Ala Met Arg Pro Ala Thr Ala Ile Ser Ala Asp Gly Pro Met Asn Leu
                325                 330                 335

Leu Glu Ala Val Arg Val Ala Gly Asp Lys Gln Ser Arg Gly Arg Gly
            340                 345                 350

Val Met Val Val Leu Asn Asp Arg Ile Gly Ser Ala Arg Tyr Ile Thr
        355                 360                 365

Lys Thr Asn Ala Ser Thr Leu Asp Thr Phe Lys Ala Asn Glu Glu Gly
    370                 375                 380

Tyr Leu Gly Val Ile Ile Gly Asn Arg Ile Tyr Tyr Gln Asn Arg Ile
385                 390                 395                 400

Asp Lys Leu His Thr Thr Arg Ser Val Phe Asp Val Arg Gly Leu Thr
                405                 410                 415

Ser Leu Pro Lys Val Asp Ile Leu Tyr Gly Tyr Gln Asp Asp Pro Glu
            420                 425                 430

Tyr Leu Tyr Asp Ala Ala Ile Gln His Gly Val Lys Gly Ile Val Tyr
        435                 440                 445

Ala Gly Met Gly Ala Gly Ser Val Ser Val Arg Gly Ile Ala Gly Met
    450                 455                 460

Arg Lys Ala Met Glu Lys Gly Val Val Ile Arg Ser Thr Arg Thr
465                 470                 475                 480

Gly Asn Gly Ile Val Pro Pro Asp Glu Glu Leu Pro Gly Leu Val Ser
                485                 490                 495

Asp Ser Leu Asn Pro Ala His Ala Arg Ile Leu Leu Met Leu Ala Leu
            500                 505                 510

Thr Arg Thr Ser Asp Pro Lys Val Ile Gln Glu Tyr Phe His Thr Tyr
        515                 520                 525

<210> SEQ ID NO 12
<211> LENGTH: 1717
<212> TYPE: DNA
<213> ORGANISM: Artificial Sequence
<220> FEATURE:
<223> OTHER INFORMATION: Nucleotide sequence encoding
      Asparaginase-PA(200)-fusion protein

<400> SEQUENCE: 12
tctagaaata attttgttta actttaagaa ggagatatac atatgttcaa attcaaaaaa      60
aacttcctgg tgggtctgag cgcagcactg atgagcatta gcctgtttag cgcaaccgca     120
agcgcagccg cgccagcggc cccggccccct gccgcgcccg ctgctcccgc ccctgctgcc    180

```
ccagccgccg ctcctgcggc acctgcgccc gccgcgccgg cagcgccggc accggcagct    240
ccggcggccg cgcctgcagc tcctgcaccg gcggctccag cagccccggc gccggccgca    300
cctgcggcgg cgcccgcggc gcctgcaccc gcagcgcctg cggcaccggc cccagcagcc    360
cctgccgccg caccggctgc gcctgcccca gcggcccccg ctgccccggc ccggcggct     420 ccagccgcag cgcctgccgc cccagcgccc gcagcaccgg cggcaccagc tccggcggcg    480 ccggcggcg ctccggcagc tccggcccct gctgcgccgg ctgcgccggc tccggcggcc     540
cctgcggcgg ctccggccgc acctgcacct gccgcgccgg ctgctccggc cccggctgcc    600
ccagcagcgg caccagcagc gcctgctcct gcggcgcctg cagctccggc gccggcagcc    660
ccggccgccg cacccgcggc tccagccccc gccgctccag cagccccgc gccagctgca     720 cctgctgccg cagataaact gccgaatatt gttattctgg caaccggtgg caccattgca    780
ggtagcgcag caaccggcac ccagaccacc ggttataaag ccggtgcact gggtgttgat    840
accctgatta atgcagttcc ggaagttaaa aaactggcca atgttaaagg tgagcagttt    900
agcaatatgg ccagcgaaaa tatgaccggt gatgttgttc tgaaactgag ccagcgtgtt    960
aatgaactgc tggcacgtga tgatgttgat ggtgttgtta ttacccatgg caccgatacc   1020
gttgaagaaa gcgcatattt tctgcatctg accgtgaaaa gcgataaacc ggttgttttt   1080
gttgcagcaa tgcgtccggc aaccgccatt agcgcagatg gtccgatgaa tctgctggaa   1140
gcagttcgtg ttgccggtga taaacagagc cgtggtcgtg tgttatggt tgtgctgaat    1200 gatcgtattg gtagcgcacg ttatattacc aaaaccaatg caagcaccct ggatacctttt  1260 aaagcaaatg aagaaggtta tctgggcgtc attattggca atcgtatcta ttatcagaac   1320
cgcatcgaca aactgcatac cacccgtagc gttttgatg ttcgtggtct gaccagcctg    1380
ccgaaagtgg atattctgta tggttatcag gatgatccgg aatatctgta tgatgcagca   1440
attcagcatg gtgtgaaagg tattgtttat gcaggtatgg gtgcgggtag cgttagcgtt   1500
cgtggtattg ccggtatgcg taaagcaatg gaaaaaggtg ttgttgtgat tcgtagcacc   1560
cgtaccggta atggtattgt tccgcctgat gaagaactgc tggtctggt tagcgatagc   1620 ctgaatccgg cacatgcacg tattctgctg atgctggcac tgacccgtac cagcgatccg   1680
aaagttattc aagaatatatt tcatacctat taagctt                          1717
```

<210> SEQ ID NO 13
<211> LENGTH: 728
<212> TYPE: PRT
<213> ORGANISM: Artificial Sequence
<220> FEATURE:
<223> OTHER INFORMATION: Asparaginase-PA-(400)-fusion protein

<400> SEQUENCE: 13

```
Ala Ala Pro Ala Ala Pro Ala Pro Ala Ala Pro Ala Ala Pro Ala Pro
1               5                   10                  15

Ala Ala Pro Ala Ala Ala Pro Ala Ala Pro Ala Pro Ala Ala Pro Ala
            20                  25                  30

Ala Pro Ala Pro Ala Ala Pro Ala Ala Ala Pro Ala Ala Pro Ala Pro
        35                  40                  45

Ala Ala Pro Ala Ala Pro Ala Ala Pro Ala Ala Pro Ala Ala Pro Ala
    50                  55                  60

Ala Pro Ala Pro Ala Ala Pro Ala Ala Pro Ala Ala Pro Ala Ala Pro Ala
65                  70                  75                  80

Ala Ala Pro Ala Ala Pro Ala Pro Ala Ala Pro Ala Ala Pro Ala Pro
```

```
                    85                  90                  95
Ala Ala Pro Ala Ala Pro Ala Ala Pro Ala Pro Ala Ala Pro Ala
                100                 105                 110
Ala Pro Ala Pro Ala Ala Pro Ala Ala Ala Pro Ala Ala Pro Ala Pro
        115                 120                 125
Ala Ala Pro Ala Ala Pro Ala Pro Ala Ala Pro Ala Ala Pro Ala
        130                 135                 140
Ala Pro Ala Pro Ala Ala Pro Ala Pro Ala Ala Pro Ala
145                 150                 155                 160
Ala Ala Pro Ala Ala Pro Ala Pro Ala Ala Pro Ala Ala Pro
            165                 170                 175
Ala Ala Pro Ala Ala Pro Ala Ala Pro Ala Pro Ala Ala Pro Ala
            180                 185                 190
Ala Pro Ala Pro Ala Ala Pro Ala Ala Ala Pro Ala Ala Pro Ala Pro
        195                 200                 205
Ala Ala Pro Ala Ala Pro Ala Pro Ala Ala Pro Ala Ala Ala Pro Ala
        210                 215                 220
Ala Pro Ala Pro Ala Ala Pro Ala Ala Pro Ala Pro Ala Ala Pro Ala
225                 230                 235                 240
Ala Ala Pro Ala Ala Pro Ala Pro Ala Ala Pro Ala Ala Pro Ala Pro
            245                 250                 255
Ala Ala Pro Ala Ala Pro Ala Ala Pro Ala Pro Ala Ala Pro Ala
            260                 265                 270
Ala Pro Ala Pro Ala Ala Pro Ala Ala Pro Ala Ala Pro Ala Pro
        275                 280                 285
Ala Ala Pro Ala Ala Pro Ala Pro Ala Ala Pro Ala Ala Pro Ala
        290                 295                 300
Ala Pro Ala Pro Ala Ala Pro Ala Ala Pro Ala Ala Pro Ala Pro
305                 310                 315                 320
Ala Ala Pro Ala Ala Pro Ala Pro Ala Ala Pro Ala Ala Pro Ala Pro
            325                 330                 335
Ala Ala Pro Ala Ala Pro Ala Ala Pro Ala Pro Ala Ala Pro Ala
            340                 345                 350
Ala Pro Ala Pro Ala Ala Pro Ala Ala Pro Ala Ala Pro Ala Pro
        355                 360                 365
Ala Ala Pro Ala Ala Pro Ala Pro Ala Ala Pro Ala Ala Ala Pro Ala
        370                 375                 380
Ala Pro Ala Pro Ala Ala Pro Ala Ala Pro Ala Pro Ala Ala Pro Ala
385                 390                 395                 400
Ala Ala Asp Lys Leu Pro Asn Ile Val Ile Leu Ala Thr Gly Gly Thr
                405                 410                 415
Ile Ala Gly Ser Ala Ala Thr Gly Thr Gln Thr Thr Gly Tyr Lys Ala
                420                 425                 430
Gly Ala Leu Gly Val Asp Thr Leu Ile Asn Ala Val Pro Glu Val Lys
                435                 440                 445
Lys Leu Ala Asn Val Lys Gly Glu Gln Phe Ser Asn Met Ala Ser Glu
        450                 455                 460
Asn Met Thr Gly Asp Val Val Leu Lys Leu Ser Gln Arg Val Asn Glu
465                 470                 475                 480
Leu Leu Ala Arg Asp Asp Val Asp Gly Val Val Ile Thr His Gly Thr
                485                 490                 495
Asp Thr Val Glu Glu Ser Ala Tyr Phe Leu His Leu Thr Val Lys Ser
                500                 505                 510
```

```
Asp Lys Pro Val Val Phe Val Ala Ala Met Arg Pro Ala Thr Ala Ile
    515                 520                 525

Ser Ala Asp Gly Pro Met Asn Leu Leu Glu Ala Val Arg Val Ala Gly
    530                 535                 540

Asp Lys Gln Ser Arg Gly Arg Gly Val Met Val Val Leu Asn Asp Arg
545                 550                 555                 560

Ile Gly Ser Ala Arg Tyr Ile Thr Lys Thr Asn Ala Ser Thr Leu Asp
                565                 570                 575

Thr Phe Lys Ala Asn Glu Glu Gly Tyr Leu Gly Val Ile Ile Gly Asn
            580                 585                 590

Arg Ile Tyr Tyr Gln Asn Arg Ile Asp Lys Leu His Thr Thr Arg Ser
        595                 600                 605

Val Phe Asp Val Arg Gly Leu Thr Ser Leu Pro Lys Val Asp Ile Leu
    610                 615                 620

Tyr Gly Tyr Gln Asp Asp Pro Glu Tyr Leu Tyr Asp Ala Ala Ile Gln
625                 630                 635                 640

His Gly Val Lys Gly Ile Val Tyr Ala Gly Met Gly Ala Gly Ser Val
                645                 650                 655

Ser Val Arg Gly Ile Ala Gly Met Arg Lys Ala Met Glu Lys Gly Val
            660                 665                 670

Val Val Ile Arg Ser Thr Arg Thr Gly Asn Gly Ile Val Pro Pro Asp
        675                 680                 685

Glu Glu Leu Pro Gly Leu Val Ser Asp Ser Leu Asn Pro Ala His Ala
690                 695                 700

Arg Ile Leu Leu Met Leu Ala Leu Thr Arg Thr Ser Asp Pro Lys Val
705                 710                 715                 720

Ile Gln Glu Tyr Phe His Thr Tyr
                725

<210> SEQ ID NO 14
<211> LENGTH: 2317
<212> TYPE: DNA
<213> ORGANISM: Artificial Sequence
<220> FEATURE:
<223> OTHER INFORMATION: Nucleotide sequence encoding
      Asparaginase-PA(400)-fusion protein

<400> SEQUENCE: 14
tctagaaata attttgttta actttaagaa ggagatatac atatgttcaa attcaaaaaa    60
aacttcctgg tgggtctgag cgcagcactg atgagcatta gcctgtttag cgcaaccgca   120
agcgcagccg cgccagcggc cccggcccct gccgcgcccg ctgctcccgc ccctgctgcc   180
ccagccgccg ctcctgcggc acctgcgccc gccgcgccgg cagcgccggc accggcagct   240
ccggcggccg cgcctgcagc tcctgcaccg gcggctccag cagccccggc gccggccgca   300
cctgcgcggg cgcccgcggc gcctgcaccc gcagcgcctg cggcaccggc ccagcagcc   360 cctgccgcca ccggctgcg cctgccccca gggcccccg ctgccccggc ccggcggct   420 ccagccgcag cgcctgccgc cccagcgccc gcagcaccgg cggcaccagc tccggcggcg   480 ccggcggcg ctccggcagc tccggcccct gctgcgccgg ctgcgccggc tccggcggcc   540
cctgcggcgg ctccggccgc acctgcacct gccgcgccgg ctgctccggc cccggctgcc   600
ccagcagcgg caccagcagc gcctgctcct gcggcgcctg cagctccggc gccggcagcc   660
ccggccgccg cacccgcggc tccagccccc gccgctccag cagccccgc gccagctgca   720 cctgctgccg ctcctgctgc ccctgctccc gctgccccg ccgccccgc cccagctgcc   780
```

```
cccgctgccg cacctgctgc cccagctccc gctgccccag ccgcgccggc ccccgcagct    840
ccagccgcgg caccagctgc cccagctcca gcggcgcctg ctgccccggc ccccgcggca    900
ccggctgccg cgcccgcagc tccagcgcct gctgcaccgg ctgctccggc acccgccgcg    960
ccagcagctg cccctgcggc accagctcct gctgcccccg cggcacctgc acccgctgcc   1020
ccggcggcag ctcccgccgc gccagcccct gcagctcctg ctgcacctgc tcctgccgcc   1080
cctgctgctg cccctgctgc tccagcccct gcagcaccgg ccgctccagc tcctgccgct   1140
cctgccgctg cgcccgctgc tccagcccca gctgcgccag cagctcctgc acctgctgcc   1200
cctgccgccg cccctgcggc tccagcacct gctgcaccgg ccgccccggc gcccgctgcc   1260
cccgcagcag cccagccgc acccgctcca gcagctcccg cagccccagc acccgcagca   1320
ccagccgccg cagataaact gccgaatatt gttattctgg caaccggtgg caccattgca   1380
ggtagcgcag caaccggcac ccagaccacc ggttataaag ccggtgcact gggtgttgat   1440
accctgatta atgcagttcc ggaagttaaa aaactggcca atgttaaagg tgagcagttt   1500
agcaatatgg ccagcgaaaa tatgaccggt gatgttgttc tgaaactgag ccagcgtgtt   1560
aatgaactgc tggcacgtga tgatgttgat ggtgttgtta ttacccatgg caccgatacc   1620
gttgaagaaa gcgcatattt tctgcatctg accgtgaaaa gcgataaacc ggttgttttt   1680
gttgcagcaa tgcgtccggc aaccgccatt agcgcagatg gtccgatgaa tctgctggaa   1740
gcagttcgtg ttgccggtga taaacagagc cgtggtcgtg gtgttatggt tgtgctgaat   1800
gatcgtattg gtagcgcacg ttatattacc aaaaccaatg caagcaccct ggatatccttt  1860
aaagcaaatg aagaaggtta tctgggcgtc attattggca atcgtatcta ttatcagaac   1920
cgcatcgaca aactgcatac cacccgtagc gtttttgatg ttcgtggtct gaccagcctg   1980
ccgaaagtgg atattctgta tggttatcag gatgatccgg aatatctgta tgatgcagca   2040
attcagcatg gtgtgaaagg tattgtttat gcaggtatgg gtgcgggtag cgttagcgtt   2100
cgtggtattg ccggtatgcg taaagcaatg gaaaaaggtg ttgttgtgat tcgtagcacc   2160
cgtaccggta atggtattgt tccgcctgat gaagaactgc tggtctggt tagcgatagc   2220
ctgaatccgg cacatgcacg tattctgctg atgctggcac tgacccgtac cagcgatccg   2280
aaagttattc aagaatattt tcatacctat taagctt                            2317
```

<210> SEQ ID NO 15
<211> LENGTH: 40
<212> TYPE: PRT
<213> ORGANISM: Artificial Sequence
<220> FEATURE:
<223> OTHER INFORMATION: PA(40) peptide

<400> SEQUENCE: 15

Ala Ala Pro Ala Ala Pro Ala Pro Ala Ala Pro Ala Ala Pro Ala Pro
1               5                   10                  15

Ala Ala Pro Ala Ala Ala Pro Ala Ala Pro Ala Pro Ala Ala Pro Ala
            20                  25                  30

Ala Pro Ala Pro Ala Ala Pro Ala
        35                  40

<210> SEQ ID NO 16
<211> LENGTH: 22
<212> TYPE: PRT
<213> ORGANISM: Artificial Sequence
<220> FEATURE:
<223> OTHER INFORMATION: modified PA(20) peptide

```
<220> FEATURE:
<221> NAME/KEY: VARIANT
<222> LOCATION: 1
<223> OTHER INFORMATION: Xaa = Pga (pyroglutamic acid)
<220> FEATURE:
<221> NAME/KEY: VARIANT
<222> LOCATION: 22
<223> OTHER INFORMATION: Xaa = Ahx (6-aminohexanoic acid)

<400> SEQUENCE: 16

Xaa Ala Ala Pro Ala Ala Pro Ala Pro Ala Ala Pro Ala Ala Pro Ala
1               5                   10                  15

Pro Ala Ala Pro Ala Xaa
            20

<210> SEQ ID NO 17
<211> LENGTH: 42
<212> TYPE: PRT
<213> ORGANISM: Artificial Sequence
<220> FEATURE:
<223> OTHER INFORMATION: modified PA(40)-peptide
<220> FEATURE:
<221> NAME/KEY: VARIANT
<222> LOCATION: 1
<223> OTHER INFORMATION: Xaa = Pga (pyroglutamic acid)
<220> FEATURE:
<221> NAME/KEY: VARIANT
<222> LOCATION: 42
<223> OTHER INFORMATION: Xaa = Ahx (6-aminohexanoic acid)

<400> SEQUENCE: 17

Xaa Ala Ala Pro Ala Ala Pro Ala Pro Ala Ala Pro Ala Ala Pro Ala
1               5                   10                  15

Pro Ala Ala Pro Ala Ala Ala Pro Ala Ala Pro Ala Pro Ala Ala Pro
            20                  25                  30

Ala Ala Pro Ala Pro Ala Ala Pro Ala Xaa
            35                  40
```

MODIFIED L-ASPARAGINASE

The contents of the text file submitted electronically herewith are incorporated herein by reference in their entirety: A computer readable format copy of the Sequence Listing (filename: sequence listing; date recorded: Sep. 15, 2017; file size: 35 KB).

BACKGROUND

Proteins with L-asparagine aminohydrolase activity, commonly known as L-asparaginases, have successfully been used for the treatment of Acute Lymphoblastic Leukemia (ALL) in children for many years. ALL is the most common childhood malignant cancers (Avramis (2005) *Clin. Pharmacokinet.* 44, 367-393).

L-asparaginase has also been used to treat Hodgkin's disease, acute myelocytic Leukemia, acute myelomonocytic Leukemia, chronic lymphocytic Leukemia, lymphosarcoma, reticulosarcoma, and melanosarcoma (Kotzia (2007) *J. Biotechnol.* 127, 657-669). The anti-tumor activity of L-asparaginase is believed to be due to the inability or reduced ability of certain malignant cells to synthesize L-asparagine (Id). These malignant cells rely on an extracellular supply of L-asparagine. However, the L-asparaginase enzyme catalyzes the hydrolysis of L-asparagine to aspartic acid and ammonia, thereby depleting circulating pools of L-asparagine and killing tumor cells that cannot perform protein synthesis without L-asparagine (Id).

L-asparaginase from *E. coli* was the first enzyme drug used in ALL therapy and has been marketed as Elspar® in the United States or as KIDROLASE and L-asparaginase MEDAC in Europe. L-asparaginases have also been isolated from other microorganisms, e.g., an L-asparaginase protein from *Erwinia chrysanthemi*, named crisantaspase, that has been marketed as ERWINASE (Wriston (1985) *Meth. Enzymol.* 113, 608-618; Goward (1992) *Bioseparation* 2, 335-341). L-asparaginases from other species of *Erwinia* have also been identified, including, for example, *Erwinia chrysanthemi* 3937 (Genbank Accession No. AAS67028), *Erwinia chrysanthemi* NCPPB 1125 (Genbank Accession No. CAA31239), *Erwinia carotovora* (Genbank Accession No. AAP92666), and *Erwinia carotovora* subsp. *artroseptica* (Genbank Accession No. AAS67027). These *Erwinia chrysanthemi* L-asparaginases have about 91-98% amino acid sequence identity with each other, while the *Erwinia carotovora* L-asparaginases have approximately 75-77% amino acid sequence identity with the *Erwinia chrysanthemi* L-asparaginases (Kotzia (2007) *J. Biotechnol.* 127, 657-669).

L-asparaginases of bacterial origin have a high immunogenic and antigenic potential and frequently provoke adverse reactions ranging from mild allergic reaction to anaphylactic shock in sensitized patients (Wang (2003) *Leukemia* 17, 1583-1588). *E. coli* L-asparaginase is particularly immunogenic, with reports of the presence of anti-asparaginase antibodies to *E. coli* L-asparaginase following intravenous or intramuscular administration reaching as high as 78% in adults and 70% in children (Id).

L-asparaginases from *Escherichia Coli* and *Erwinia chrysanthemi* differ in their pharmacokinetic properties and have distinct immunogenic profiles, respectively (Klug Albertsen (2001) *Brit. J. Haematol.* 115, 983-990). Furthermore, it has been shown that antibodies that developed after a treatment with L-asparaginase from *E. coli* do not cross react with L-Asparaginase from *Erwinia* (Wang (2003) *Leukemia* 17, 1583-1588). Thus, L-asparaginase from *Erwinia* (crisantaspase) has been used as a second line treatment of ALL in patients that react to *E. coli* L-asparaginase (Duval (2002) *Blood* 15, 2734-2739; Avramis (2005) *Clin. Pharmacokinet.* 44, 367-393).

In another attempt to reduce immunogenicity associated with administration of microbial L-asparaginases, an *E. coli* L-asparaginase has been developed that is modified with methoxy-polyethyleneglycol (mPEG) This so-called mPEG-L-asparaginase, or pegaspargase, marketed as ONCASPAR (Enzon Inc.), was first approved in the U.S. for second line treatment of ALL in 1994, and has been approved for first-line therapy of ALL in children and adults since 2006.

ONCASPAR is an *E. coli* L-asparaginase that has been modified at multiple lysine residues using 5 kDa mPEG-succinimidyl succinate (SS-PEG) (U.S. Pat. No. 4,179,337). SS-PEG is a PEG reagent of the first generation that contains an unstable ester linkage that is sensitive to hydrolysis by enzymes or at slightly alkaline pH values (U.S. Pat. No. 4,670,417). These properties decrease both in vitro and in vivo stability and can impair drug safety.

Furthermore, it has been demonstrated that antibodies developed against L-asparaginase from *E. coli* will cross react with ONCASPAR (Wang (2003) *Leukemia* 17, 1583-1588). Even though these antibodies were not neutralizing, this finding clearly demonstrated the high potential for cross-hypersensitivity or cross-inactivation in vivo. Indeed, in one report 30-41% of children who received pegaspargase had an allergic reaction (Id).

In addition to outward allergic reactions, the problem of "silent hypersensitivity" was recently reported, whereby patients develop anti-asparaginase antibodies without showing any clinical evidence of a hypersensitivity reaction (Wang (2003) *Leukemia* 17, 1583-1588). This reaction can result in the formation of neutralizing antibodies to *E. coli* L-asparaginase and pegaspargase; however, these patients are not switched to *Erwinia* L-asparaginase because there are not outward signs of hypersensitivity, and therefore they receive a shorter duration of effective treatment (Holcenberg (2004) *J. Pediatr. Hematol. Oncol.* 26, 273-274).

*Erwinia chrysanthemi* L-asparaginase treatment is often used in the event of hypersensitivity to *E. coli*-derived L-asparaginases. However, it has been observed that as many as 30-50% of patients receiving *Erwinia* L-asparaginase are antibody-positive (Avramis (2005), *Clin. Pharmacokinet.* 44, 367-393). Moreover, because *Erwinia chrysanthemi* L-asparaginase has a shorter elimination half-life than the *E. coli* L-asparaginases, it must be administered more frequently (Id). In a study by Avramis et. al, *Erwinia* asparaginase was associated with inferior pharmacokinetic profiles (Avramis (2007), *J. Pediatr. Hematol. Oncol.* 29, 239-247). *E. coli* L-asparaginase and pegaspargase therefore have been the preferred first-line therapies for ALL over *Erwinia* L-asparaginase.

Numerous biopharmaceuticals have successfully been PEGylated and marketed for many years. However, in many cases, PEGylated biopharmaceuticals show significantly reduced activity compared to the unmodified biopharmaceutical. In the case of L-asparaginase from *Erwinia carotovora*, it has been observed that PEGylation reduced its in vitro activity to approximately 57% (Kuchumova (2007) *Biochemistry* (Moscow) Supplement Series B: Biomedical Chemistry, 1, 230-232). The L-asparaginase from *Erwinia carotovora* has only about 75% homology to the *Erwinia chrysanthemi* L-asparaginasc (crisantaspace). For ONCASPAR it is also known that its in vitro activity is approximately 50% compared to the unmodified *E. coli* L-asparaginase.

Thus, the technical problem underlying the present invention is the provision of means and methods for treating cancer, such as leukemia or non-Hodgkin's lymphoma, that avoids the limitations and disadvantages of prior art therapies, particularly of some PEGylated asparaginases.

The technical problem is solved by provision of the embodiments characterized in the claims.

SUMMARY OF THE INVENTION

The present invention relates to a modified protein that is a combination of (i) an L-asparaginase and (ii) one or more (poly)peptide(s), wherein the (poly)peptide consists solely of proline and alanine amino acid residues. The modified protein can be formed in a number of ways, including chemical conjugation between the L-asparaginase and the (poly)peptides or by expressing the modified protein as a fusion protein. Also provided herein are nucleic acids encoding the modified protein, vectors and/or host cells comprising same, as well as processes for their production. Compositions comprising the modified protein and their use in medicine, particularly in the treatment of cancer, are disclosed. In another aspect of the invention, the L-asparaginase can be derived from *Erwinia* and/or it has at least 85% identity to the amino acid sequence of SEQ ID NO: 1.

BRIEF DESCRIPTION OF THE DRAWINGS

The foregoing summary, as well as the following detailed description of the invention, will be better understood when read in conjunction with the appended drawings.

FIG. 1: Chemistry of the conjugation of Crisantaspase with N-terminally protected P/A peptides via amino groups.

Figure 8:
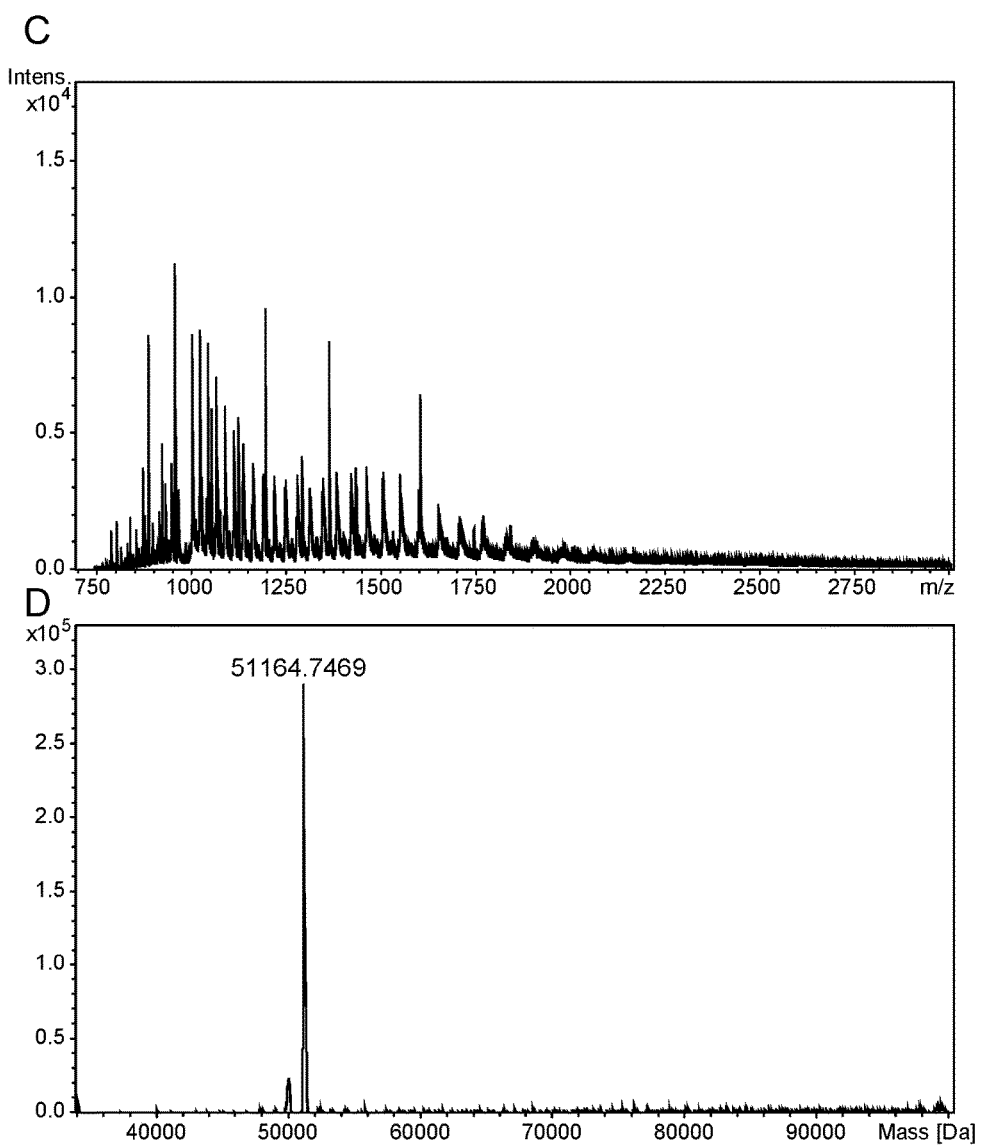

(A) and (B) depict the chemical structures of P/A peptides (SEQ ID NO: 16 and 17, amino acid sequence shown in SEQ ID NO: 5 and 15) containing either 20 or 40 Pro/Ala residues (respectively), which were obtained by solid-phase peptide synthesis. In order to avoid polymerization of the peptides upon chemical activation of the C-terminus, the N-terminus was protected with pyroglutamyl (Pga) residue Aminohexanoic acid (Ahx) was incorporated at the C-terminus of the peptides to serve as linker. (C) In the presence of the non-nucleophilic base N,N-diisopropylethylamine (DIPEA, Hünig's base), and with DMSO as solvent, the N-terminally protected P/A peptide is activated at its C-terminus with the benzotriazol derivative O-(benzotriazol-1-yl)-N,N,n',N'-tetramethyluronium tetrafluoroborate (TBTU). The hydroxybenzotriazol (HOBt) active ester of the peptide is subsequently used to derivatize the amino groups (ε-amino groups of lysine residues or α-amino group of N-terminus) of Crisantaspase with the P/A peptide through formation of peptide or isopeptide bonds, while free HOBt is released. This coupling step is performed in aqueous solution (e.g. PBS buffer) with a content of organic solvent ≤30%. The P/A-Crisantaspase modified protein may be purified from residual P/A peptide/coupling reagent by dialysis and/or chromatography (e.g. ion exchange chromatography).

FIG. 2: Optimization of Crisantaspase/Pga-P/A(20)-Ahx coupling ratio.

Recombinant Crisantaspase produced in *E. coli* was conjugated with the Pga-P/A#1(20)-Ahx peptide (Part A of FIG. 1)(SEQ ID NO: 16, amino acid sequence shown in SEQ ID NO: 5) as described in Example 1. The peptide-to-protein ratio was varied between 3.5 mg and 10 mg P/A peptide per 1 mg Crisantaspase. The gel was loaded with 7 μg of Crisantaspase from each coupling reaction. Additionally, a mix of coupling reactions with ratios of 0.3 to 10 mg peptide per mg protein was applied as size standard ("Std"). The number of coupled P/A peptides can be determined by counting the bands in that ladder starting from the unconjugated Crisantaspase as marked on the right. Lane "kDa": PIERCE Unstained Protein MW Marker (Thermo Fisher Scientific).

FIG. 3: Purification of Crisantaspase/Pga-P/A(40)-Ahx peptide coupling product via anion exchange chromatography Recombinant Crisantaspase produced in *E. coli* was conjugated with the Pga-P/A(40)-Ahx peptide (Part B of FIG. 1)(SEQ ID NO: 17, amino acid sequence shown in SEQ ID NO: 15) as described in Example 2. After dialysis against AIX running buffer (25 mM boric acid/NaOH pH 9.0, 1 mM EDTA) anion exchange chromatography was performed on an 85 mL SOURCE 15Q column (A). By applying an NaCl concentration gradient, the enzyme modified protein eluted in a single sharp peak, as revealed by the UV trace at 280 nm. Separation of remaining uncoupled peptide and other non-proteinous byproducts of the chemical conjugation devoid of UV absorption at 280 nm was monitored by the 225 nm UV trace. (B) SDS-PAGE analysis of the Crisantaspase/Pga-P/A(40)-Ahx modified protein after purification by anion exchange chromatography (lane 1). A mix of coupling reactions with ratios of 0.3 to 10 mg peptide per mg protein was applied to lane 2 to allow determination of the number of coupled P/A peptides per Crisantaspase monomer. PAGERULER Plus Prestained marker (Thermo Fisher Scientific) was applied to lane "M".

FIG. 4: Purification of Crisantaspase/Pga-P/A(20)-Ahx peptide coupling product via anion exchange chromatography Recombinant Crisantaspase produced in *E. coli* was conjugated with the Pga-P/A(20)-Ahx peptide (Part A of FIG. 1)(SEQ ID NO: 16, amino acid sequence shown in SEQ ID NO: 5) as described in Example 3. After dialysis against AIX running buffer (25 mM boric acid/NaOH pH 9.0, 1 mM EDTA) anion exchange chromatography was performed on an 85 mL SOURCE 15Q column (A). By applying an NaCl concentration gradient the enzyme modified protein eluted in a single sharp peak, as revealed by the UV trace at 280 nm. Separation of remaining uncoupled peptide and other non-proteinous byproducts of the chemical conjugation devoid of UV absorption at 280 nm was revealed by the 225 nm UV trace. (B) SDS-PAGE analysis of the Crisantaspase/Pga-P/A(20)-Ahx modified protein after purification by anion exchange chromatography (lane 1). A mix of coupling reactions with ratios of 0.3 to 10 mg peptide per mg protein was applied to lane 2 to allow determination of the number of coupled P/A peptides per Crisantaspase monomer. PAGERULER Plus Prestained marker (Thermo Fisher Scientific) was applied to lane "M".

FIG. 5: Cloning of the expression vectors for the production of PASylated Crisantaspase in *E. coli*

(A) Plasmid map of pASK75-SapI-Crisantaspase (SEQ ID NO: 4) and (B) of its derivative pASK75-PA400-Crisantaspase (SEQ ID NO: 14) after seamless insertion of a PA#1c/1b(400) (SEQ ID NO: 10) gene cassette via the two inversely oriented SapI restriction sites. The structural gene for the biologically/pharmacologically active (pre)protein PA#1(400)-Crisantaspase (SEQ ID NO: 13) comprising the low repetitive nucleotide sequence encoding a PA#1 polypeptide with 401 amino acid residues and the structural gene for Crisantaspase as well as coding region for the bacterial Enx signal sequence ($SP^{Enx}$) is cloned under transcriptional control of the tet promoter/operator)($tet^{p/o}$). The plasmid backbone outside the expression cassette flanked by the XbaI and HindIII restriction sites is identical with that of the generic expression vector pASK75 (Skerra (1994) Gene 151:131-135). A plasmid for the expression of Crisantaspase fused to PA#1(200) (SEQ ID NO: 11) was cloned in the same way using the PA#1b(200) gene cassette (SEQ ID NO: 12).

FIG. 6: SDS-PGE analysis of recombinant Crisantaspase genetically fused with PA200 or PA400

(A) Analysis of the mature PA#1(400)-Crisantaspase fusion protein (SEQ ID NO: 13) after periplasmic extraction (PPE), ammonium sulfate precipitation (ASP) and anion exchange chromatography (AEX) by 10% SD S-PAGE. (B) The gel shows 5 μg samples of purified mature PA#1(200)-Crisantaspase (lane 1) (SEQ ID NO: 11) or PA#1(400)-Crisantaspase (lane 2) (SEQ ID NO: 13). Sizes of the marker proteins (M) are indicated on the left. The PA#1(200)-Crisantaspase and the PA#1(400)-Crisantaspase fusion protein appear as single homogeneous bands with an apparent molecular size of about 105 kDa (lane 1) or 200 kDa (lane 2), respectively. Due to poor SDS binding, PA fusion proteins generally show significantly larger sizes (Schlapschy (2013) Protein Eng Des Sel. 26:489-501) than, e.g., the calculated mass of 51 kDa for the PA#1(200)-Crisantaspase monomer or 67 kDa for the PA#1(400)-Crisantaspase monomer.

FIG. 7: Size exclusion chromatography of PASylated Crisantaspase variants (A) Overlay of elution profiles for unmodified Crisantaspase, as well as for Crisantaspase chemically conjugated either to Pga-P/A(20)-Ahx or Pga-P/A(40)-Ahx peptides (described in Examples 3 and 2, respectively) and the recombinant Crisantaspase genetically fused with either PA#1(200) (SEQ ID NO: 7) or PA#1(400) (SEQ ID NO: 9) polypeptides (described in Example 5). 150 μL of the purified protein at a concentration of 1 mg/ml was applied to a SUPERDEX S200 10/300 GL column equilibrated with PBS buffer. Absorption at 280 nm was monitored and the peak of each chromatography run was normalized to 100%.

(B) Calibration curve for the chromatograms from (A) using a SUPERDEX 5200 10/300 GL column. The logarithm of the molecular weight of marker proteins (ovalbumin, 43.0 kDa; bovine serum albumin, 66.3 kDa; alcohol dehydrogenase, 150 kDa, □-amylase, 200 kDa, apo-ferritin, 440 kDa) was plotted vs. their elution volumes (black circles) and fitted by a straight line. From the observed elution volumes of the tetrameric Crisantaspase, its PA#1 peptide modified proteins and its recombinant PA#1 fusion proteins (black squares) their apparent molecular sizes were determined as follows. Crisantaspase, 105 kDa (true mass 140 kDa); Crisantaspase/Pga-P/A(20)-Ahx modified protein, 531 kDa (true mass 228 kDa); Crisantaspase/Pga-P/A(40)-Ahx modified protein, 820 kDa (true mass 284 kDa); PA200-Crisantaspase, 595 kDa (true mass 205 kDa); PA400-Crisantaspase, 1087 kDa (true mass 269 kDa). These data show that both the chemically conjugated P/A peptides and the genetic fusion with the PA#1 polypeptide confer a much enlarged hydrodynamic volume.

FIG. 8: ESI-MS analysis of PASylated Crisantaspase variants (A) The raw m/z spectrum obtained by Electrospray Ionisation Mass Spectrometry (ESI-MS) of the purified Crisantaspase/Pga-P/A(20)-Ahx modified protein prepared as described in Example 3 was deconvoluted yielding the mass spectrum (B). The observed mass species could unambiguously be assigned to Crisantaspase conjugated with 9 to 14 peptides (cf. Table 3). Major peaks, however, were observed only for protein species with 10 to 13 peptides, what corresponds to the determination of the peptide coupling ratio by SDS-PAGE (cf. Part B of FIG. 4). (C) and (E) show raw m/z spectra of the PA200-Crisantaspase and PA400-Crisantaspase fusion proteins prepared in Example 5. The deconvoluted mass spectra (D) and (F) revealed masses of 51164.75 Da and 67199.17 Da, respectively, which correspond almost perfectly to the calculated masses of 51163.58 Da.

Figure 9:
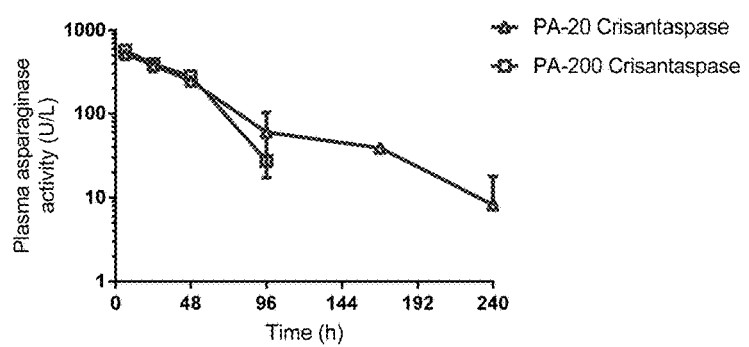

FIG. 9: Mean (±SD) Plasma concentration versus time profiles following a single IV bolus dose to Male CD-1 mice The figures shows plasma asparaginase activity of PA-crisantaspase conjugates following a single IV bolus dose to male mice.

DETAILED DESCRIPTION OF THE INVENTION

Unless defined otherwise, all technical and scientific terms used herein have the same meaning as is commonly understood by one of skill in the art to which this invention belongs. All patents and publications referred to herein are incorporated by reference in their entireties.

In one aspect, the present invention relates to a modified protein comprising (i) an L-asparaginase and (ii) one or more (poly)peptide(s), wherein the (poly)peptide consists solely of proline and alanine amino acid residues. In a preferred aspect the invention relates to a modified protein comprising (i) an L-asparaginase having at least 85% identity to the amino acid sequence of SEQ ID NO: 1 and (ii) one or more (poly)peptide(s), wherein the (poly)peptide consists solely of proline and alanine amino acid residues.

The present invention relates, inter alia, to a modified protein comprising (i) an L-asparaginase and (ii) one or more (poly)peptide(s), wherein the (poly)peptide consists solely of proline and alanine amino acid residues. In some embodiments, said L-asparaginase has at least 85% or 100% identity to the amino acid sequence of SEQ ID NO: 1. In additional embodiments, the modified protein has an asparaginase or glutaminase activity higher than that of the unmodified L-asparaginase. In further embodiments, said modified protein has an L-asparagine depletion activity at least about 20% higher than the unmodified L-asparaginase. In yet further embodiments, said L-asparaginase is a tetramer.

In some embodiments, the modified protein described herein is a modified protein of said L-asparaginase and a polypeptide, wherein the polypeptide consists solely of proline and alanine amino acid residues. In some embodiments, said polypeptide consists of about 100 to 600 proline and alanine amino acid residues, particularly about 200 to about 400 proline and alanine amino acid residues. In further embodiments, said polypeptide consists of a total of about 200 proline and alanine amino acid residues or a total of about 400 proline and alanine amino acid residues. In additional embodiments, said proline residues constitute more than about 10% and less than about 70% of the polypeptide. In yut additional embodiments, said polypeptide comprises a plurality of amino acid repeats, wherein said repeat consists of proline and alanine residues and wherein no more than 6 consecutive amino acid residues are identical. For example, said polypeptide comprises or consists of the amino acid sequence AAPAAPAPAAPAAPA-PAAPA (SEQ ID NO: 5) or circular permuted versions or (a) multimers(s) of the sequences as a whole or parts of the sequence. In one aspect, said polypeptide comprises or consists of an amino acid sequence as shown in SEQ ID NO: 7 or 9; said polypeptide comprises or consists of an amino acid sequence encoded by a nucleic acid having a nucleotide sequence as shown in SEQ ID NO: 8 or 10; said modified protein comprises or consists of an amino acid sequence as shown in SEQ ID NO: 11 or 13; or said modified protein comprises or consists of an amino acid sequence encoded by a nucleic acid having a nucleotide sequence as shown in SEQ ID NO: 12 or 14. In some embodiments, said polypeptide is a random coil polypeptide. In further embodiments, the modified protein is a fusion protein of the L-asparaginase and the polypeptide.

In one aspect, the modified protein is a modified protein of L-asparaginase and one or more peptide(s), wherein each is independently a peptide $R^N$-(P/A)-$R^C$, (P/A) is an amino acid sequence consisting solely of proline and alanine amino acid residues, wherein $R^N$ is a protecting group attached to the N-terminal amino group of the amino acid sequence, and $R^C$ is an amino acid residue bound via its amino group to the C-terminal carboxy group of the amino acid sequence, each peptide is conjugated to the L-asparaginase via an amide linkage formed from the carboxy group of the C-terminal amino acid residue $R^C$ of the peptide and a free amino group of the L-asparaginase, and at least one of the free amino groups, which the peptides are conjugated to, is not an N-terminal α-amino group of the L-asparaginase. In some embodiments, said amino acid sequence consists of a total of between 15 to 45 proline and alanine amino acid residues. In additional embodiments, said amino acid sequence consists of 20 or 40 proline and alanine amino acid residues. In further embodiments, said proline residues constitute more than about 10% and less than about 70% of the amino acid sequence. For example, said amino acid sequence is AAPAAPAPAAPAAPAPAAPA (SEQ ID NO: 5) or AAPAAPAPAAPAAPAPAAPAAAPAAPAPAAPAAPA-PAAPA (SEQ ID NO: 15). In yet further embodiments, $R^N$ is pyroglutamoyl or acetyl, and/or $R^C$ is ε-aminohexanoic acid. In some embodiments, the peptides comprised in said modified protein adopt a random coil conformation. In additional embodiments, all of the peptides comprised in said modified protein are the same. In yet additional embodiments, at least one of the free amino groups, which the peptides are conjugated to, is an ε-amino group of a lysine residue of the L-asparaginase. In further embodiments, the free amino groups, which the peptides are conjugated to, are selected from the group comprising the ε-amino group(s) of any lysine residue(s) of the L-asparaginase and the N-terminal α-amino group(s) of the L-asparaginase. In yet further embodiments, the L-asparaginase is composed of four subunits, and wherein 9 to 13 peptides as defined in any one of items 15 to 24 are conjugated to each subunit of the L-asparaginase.

In one aspect, the polypeptide or peptide described herein mediates a decreased immunogenicity of said modified protein.

In another aspect, the disclosure is related to a nucleic acid encoding the modified protein described herein. In some embodiments, said nucleic acid is selected from the group consisting of: (a) the nucleic acid comprising the nucleotide sequence of SEQ ID NO: 12 or 14; (b) the nucleic acid comprising the nucleotide sequence having at least 85% identity to the nucleotide sequence as defined in (a); and (c) the nucleic acid being degenerate as a result of the genetic code to the nucleotide sequence as defined in (a) or (b).

In another aspect, the disclosure is related to a vector comprising the nucleic acid described herein. In another aspect, the disclosure is related to a host cell comprising the nucleic acid and/or the vector described herein. In some embodiments, said host cell is selected from the group consisting of *Pseudomonas fluorescens* and *Corynebacterium glutamicum*.

In another aspect, the disclosure is related to a process for the preparation of a modified protein described herein or of a nucleic acid described herein. In some embodiments, the mprocess comprises culturing the host cell according to item 33 or 34 and isolating said modified protein from the culture or from said cell.

In another aspect, the disclosure is related to a process of preparing a modified protein as defined in any one of items 17 to 29, the process comprising: (a) coupling an activated peptide of the formula $R^N$-(P/A)-$R^{C\text{-}act}$, wherein $R^{C\text{-}act}$ is a carboxy-activated form of $R^C$, wherein $R^C$ and (P/A) are as defined in the modified protein to be prepared, and wherein $R^N$ is a protecting group which is attached to the N-terminal amino group of (P/A), with L-asparaginase to obtain a modified protein of the L-asparaginase and peptides in which $R^N$ is a protecting group. In some embodiments, the activated carboxy group of the amino acid residue $R^{C\text{-}act}$ in the activated peptide is an active ester group.

In another aspect, the disclosure is related to a composition comprising the modified protein described herein or the modified protein prepared by the process described herein. In some embodiments, the composition is a pharmaceutical composition, optionally further comprising (a) pharmaceutical acceptable carrier(s) or excipient(s).

In another aspect, the modified protein described herein, the modified protein prepared by the process described herein, or the composition described herein may be used as a medicament. In another aspect, the modified protein described herein, the modified protein prepared by the process described herein, or the composition described herein may be used in the treatment of a disease, e.g. a disease treatable by L-asparagine depletion in a patient. In another aspect, the modified protein described herein, the modified protein prepared by the process described herein, or the composition described herein may be used in the treatment of cancer.

In another aspect, the disclosure is related to a method of treating a disease treatable by L-asparagine depletion in a patient, said method comprising administering to said patient an effective amount of the modified protein described herein, the modified protein prepared by the process described herein, or the composition described herein. In some embodiments, said disease treatable by L-asparagine depletion is a cancer. In another aspect, the disclosure is related to a method of treating cancer comprising the administration of the modified protein described herein, the modified protein prepared by the process described herein, or the composition described herein, to a subject.

In some embodiments, said cancer is a non-solid cancer. In additional embodiments, said non-solid cancer is leukemia or non-Hodgkin's lymphoma. In yet additional embodiments, said leukemia is acute lymphoblastic leukemia (ALL) or acute myeloid leukemia (AML); or the method according to item 48, wherein said leukemia is acute lymphoblastic leukemia (ALL) or acute myeloid leukemia (AML).

In another aspect, said modified protein described herein elicits a lower immunogenic response in said patient compared to the unmodified L-asparaginase. In some embodiments, said modified protein has a longer in vivo circulating half-life after a single dose compared to the unmodified L-asparaginase. In additional embodiments, said modified protein has a greater AUC value after a single dose compared to the unmodified L-asparaginase. In yet additional embodiments, said patient has had a previous hypersensitivity to an *E. coli* L-asparaginase or PEGylated form thereof. In further embodiments, said patient has had a previous hypersensitivity to an *Erwinia* L-asparaginase. In yet further embodiments, the treatment comprises intravenous administration of said modified protein.

In one aspect, the present invention relates to a modified protein comprising (i) a recombinant L-asparaginase having at least 85% identity to the amino acid sequence of SEQ ID NO: 1 and (ii) one or more (poly)peptide(s), wherein the (poly)peptide consists solely of proline and alanine amino acid residues. The explanations and definitions given herein in relation to the terms "modified protein", "L-asparaginase", "(poly)peptide(s)" and the like provided herein apply mutatis mutandis. The term "recombinant L-asparaginase" as used herein refers to a recombinant form of L-asparaginase having at least 85% identity to the amino acid sequence of a native *Erwinia* L-asparaginase. The term "recombinant" may refer to a recombinantly produced L-asparaginase, e.g. a L-asparaginase produced in a host cell comprising a nucleic acid encoding the L-asparaginase.

The modified proteins further show an enhanced plasma half-life and, thus, a prolonged duration of action as compared to the respective unconjugated L-asparaginase. This allows for a reduction of the dosing frequency and thus the side-effect burden. The invention also provides processes of preparing the modified proteins as described herein.

In certain aspects, the invention relates to a modified protein comprising (i) an L-asparaginase having at least 85, 86, 87, 88, 89, 90, 91, 92, 93, 94, 95, 96, 97, 98, 99 or 100% identity to the amino acid sequence of SEQ ID NO: 1 and (ii) one or more (poly)peptide(s), wherein the (poly)peptide(s) consist(s) solely of proline and alanine amino acid residues. It is understood that the term "consisting solely of proline and alanine amino acid residues" means that at least one proline residue and at least one alanine residue are present, i.e. both at least one proline residue and at least one alanine residue must be present. In a preferred aspect, the invention relates to a modified protein comprising (i) a recombinant L-asparaginase having the amino acid sequence of SEQ ID NO: 1 and (ii) one or more (poly)peptide(s), wherein the (poly)peptide consists solely of proline and alanine amino acid residues. In one aspect, the L-asparaginase is a tetramer (i.e. the L-asparaginase composed of four subunits or monomers). One exemplary subunit or monomer has the amino acid sequence of SEQ ID NO: 1.

In one aspect, the (poly)peptide (i.e. polypeptide or peptide) mediates a decreased immunogenicity of the modified protein described herein, e.g. a decreased immunogenicity of the modified protein as compared to the unconjugated L-asparaginase.

As shown in the appended examples, the PA#1(200)-Crisantaspase protein had 109% and the PA#1(400)-Crisantaspase protein had 118% of enzyme activity compared to the unmodified Crisantaspase; see Example 5. This demonstrates that the fusion of asparaginases as described herein with polypeptides does not affect enzymatic activity. Surprisingly, the activity even increased with the length of the PA-polypeptide.

More generally, the herein provided modified proteins have the same or substantially the same (enzymatic) activity compared to unmodified asparaginase. The (enzymatic) activity may be assessed by the Nessler assay. Details of the Nessler assay are provided in the appended examples and/or are disclosed in the prior art e.g. Mashburn (1963) *Biochem. Biophys. Res. Commun.* 12, 50 (incorporated herein by reference in its entirety). Accordingly, in one aspect, the herein provided modified proteins have the same or substantially the same (enzymatic) activity compared to unmodified asparaginase as assessed by a Nessler assay. The term "unmodified asparaginase" as used herein refers to a native asparaginase, i.e. an asparaginase that is not modified by fusion/conjugation with (poly)peptides as defined herein.

For example, an "unmodified asparaginase" is an L-asparaginase having at least 85% identity to the amino acid sequence of SEQ ID NO: 1. In a preferred aspect, an "unmodified asparaginase" is an L-asparaginase having the amino acid sequence of SEQ ID NO:1.

In some aspects, the herein provided modified proteins have an (enzymatic) activity higher than that of the unmodified L-asparaginase. The (enzymatic) activity may be assessed by the Nessler assay for example. Details of the Nessler assay are provided in the appended examples and/or are disclosed in the prior art e.g. Mashburn (1963) *Biochem. Biophys. Res. Commun.* 12, 50 (incorporated herein by reference in its entirety). Accordingly, in one aspect, the herein provided modified proteins have an (enzymatic) activity higher than that of the unmodified L-asparaginase as assessed by a Nessler assay. The term "unmodified asparaginase" as used herein refers to a native asparaginase, i.e. an asparaginase that is not modified by fusion/conjugation with (poly)peptides as defined herein. For example, an "unmodified asparaginase" is an L-asparaginase having at least 85% identity to the amino acid sequence of SEQ ID NO: 1. In a preferred aspect, an "unmodified asparaginase" is an L-asparaginase having the amino acid sequence of SEQ ID NO: 1. For example, the modified proteins have an (enzymatic) activity that can be at least 5% and/or up to 30% (e.g. at least 10%, 15%, 20%, 25% (or more)) higher than that of the L-asparaginase, particularly higher than that of the unmodified L-asparaginase, particularly as assessed by the Nessler assay. The above explanations apply in particular to the herein provided fusion proteins (e.g. modified protein of L-asparaginase and a polypeptide, wherein the polypeptide consists solely of proline and alanine amino acid residues), but are not limited thereto.

In some aspects, the modified proteins have an asparaginase activity or glutaminase activity higher than that of the unmodified L-asparaginase. For example, the modified proteins can have an asparaginase activity or glutaminase activity at least 5% and/or up to 30% (e.g. at least 10%, 15%, 20%, 25% (or more)) higher than that of the L-asparaginase, particularly higher than that of the unmodified L-asparaginase. In some embodiments, the asparaginase activity or glutaminase activity may be measured by Nessler assay. The rate of hydrolysis of asparagine may be determined by measuring released ammonia, and the amount of released ammonia from using the modified proteins disclosed herein may be compared with that from using the L-asparaginase or unmodified L-asparaginase. In additional aspects, said modified proteins have an L-asparagine depletion activity higher than that of the unmodified L-asparaginase. In additional embodiments, the modified proteins have an L-asparagine depletion activity at least 5% and/or up to 30% (e.g. at least 10%, 15%, 20%, 25% (or more)) higher than that of the L-asparaginase, particularly higher than that of the unmodified L-asparaginase, for example as assessed by the Nessler assay. The invention also relates to a pharmaceutical composition comprising the modified protein, and the modified protein or the pharmaceutical composition for use in therapy, or for use as a medicament, or for use in medicine.

Generally, a modified protein can be obtained by chemical coupling or by genetic fusion (in the case of conjugation with another protein or peptide). The term "fusion protein"

as used herein relates primarily to a modified protein comprising (i) an L-asparaginase and (ii) one or more polypeptide(s), wherein the polypeptide consists solely of proline and alanine amino acid residues. In this context, the polypeptide can consist of about 200 to about 400 proline and alanine amino acid residues. Exemplary amino acid sequences of such polypeptides are shown in SEQ ID NO: 7 or 9.

If the modified protein is obtained by chemical coupling, it comprises (i) an L-asparaginase and (ii) one or more peptide(s), wherein the peptide consists solely of proline and alanine amino acid residues. In this context, the peptide can consist of a total of between 10 to 100 proline and alanine amino acid residues, from about 15 to about 60 proline and alanine amino acid residues, from about 15 to 45 proline and alanine amino acid residues, e.g. from about 20 to about 40, for example, 20 proline and alanine amino acid residues or 40 proline and alanine amino acid residues. Exemplary amino acid sequence of such peptides are AAPAAPA-PAAPAAPAPAAPA (SEQ ID NO: 5) or AAPAAPA-PAAPAAPAPAAPAAAPAAPAPAAPAAPAPAAPA (SEQ ID NO: 15).

The term "modified protein" as used herein can be used interchangeably with the term "conjugate", particularly if the term "modified protein" refers to a modified protein obtained by chemical coupling or as a fusion protein, i.e. primarily if it comprises (i) an L-asparaginase and (ii) one or more (poly)peptide(s), wherein the (poly)peptide consists solely of proline and alanine amino acid residues. Likewise, the terms "unmodified" and "unconjugated" can be used interchangeably herein.

The invention also relates to a process of preparing the modified protein, comprising (a) coupling an activated peptide of the formula $R^N$-(P/A)-$R^{C-act}$, wherein $R^{C-act}$ is a carboxy-activated form of $R^C$, wherein $R^C$ and (P/A) are as defined in the modified protein to be prepared, and wherein $R^N$ is a protecting group which is attached to the N-terminal amino group of (P/A), with L-asparaginase to obtain a modified protein of the L-asparaginase and peptides in which $R^N$ is a protecting group.

It has been demonstrated in the appended examples (cf. Example 1, Table 1) that the modified protein can be prepared using a variety of mass ratios of the activated peptide and asparaginase. For example, mass ratios of 10:1 (activated peptide: asparaginase), 7.5:1, 5:1 or 3.5:1 can be used. It was observed that (enzymatic) activity of the modified protein was highest, if a ratio of 5:1 or below was used (cf. Example 1, Table 2). Thus, it may be advantageous to use a mass ratio of activated peptide:asparaginase of 5:1 or below, e.g. 5:1, 4:1, 3.5:1 or 3:1, in the process described herein above. The term "mass ratio" as used herein refers to the ratio of the molecular weight of the activated peptide as defined herein and of the asparaginase as defined herein (e.g. asparaginase as shown in SEQ ID NO: 1 and proteins with at least 85% identity to SEQ ID NO: 1). The "molecular weight" is typically indicated herein using the scientific unit Dalton (Da). It is well known that the molecular weight unit of the asparaginase or peptide as indicated herein in dalton (Da), is an alternative name for the unified atomic mass unit (u). A molecular weight of, e.g., 500 Da is thus equivalent to 500 g/mol. The term "kDa" (kilodalton) refers to 1000 Da.

The molecular weight of asparaginase or peptide can be determined using methods known in the art, such as, e.g., mass spectrometry (e.g., electrospray ionization mass spectrometry, ESI-MS, or matrix-assisted laser desorption/ionization mass spectrometry, MALDI-MS), gel electrophoresis (e.g., polyacrylamide gel electrophoresis using sodium dodecyl sulfate, SDS-PAGE), hydrodynamic methods (e.g., gel filtration/size exclusion chromatography, SEC, or gradient sedimentation), or dynamic (DLS) or static light scattering (e.g., multi-angle light scattering, MALS), or the molecular weight of the asparaginase or peptide can be calculated from the known amino acid sequence (and the known post-translational modifications, if present) of the asparaginase or peptide. Preferably, the molecular weight of the asparaginase or peptide is determined using mass spectrometry.

The invention also relates to a process for the preparation of the modified protein or of a nucleic acid encoding the modified protein. In some aspects, the process comprises producing an L-asparaginase in a host selected from the group comprising yeasts, such as *Saccharomyces cerevisiae* and *Pichia Pistoris*, as well as bacteria, actinomycetes, fungi, algae, and other microorganisms, including *Escherichia coli*, *Bacillus* sp., *Pseudomonas fluorescens*, *Corynebacterium glutamicum* and bacterial hosts of the following genuses, *Serratia*, *Proteus*, *Acinetobacter* and *Alcaligenes*. Other hosts are known to those of skill in the art, including *Nocardiopsis alba*, which expresses a variant of Asparaginase lacking on glutaminase-activity (Meena et al. (2014) *Bioprocess Biosyst. Eng.* October 2014 Article, which is incorporated by reference herein in its entirety), and those disclosed in Savitri et al. (2003) *Indian Journal of Biotechnology*, 2, 184-194, which is incorporated by reference herein in its entirety.

The modified protein can be a fusion protein comprising (i) a L-asparaginase having at least 85% identity to the amino acid sequence of SEQ ID NO: 1 and (ii) one or more polypeptide(s), wherein the polypeptide consists solely of proline and alanine amino acid residues.

The proline residues in the polypeptide consisting solely of proline and alanine amino acid residues may constitute more than about 10% and less than about 70% of the polypeptide. Accordingly, it is preferred that 10% to 70% of the total number of amino acid residues in the polypeptide are proline residues; more preferably, 20% to 50% of the total number of amino acid residues comprised in the polypeptide are proline residues; and even more preferably, 30% to 40% (e.g., 30%, 35% or 40%) of the total number of amino acid residues comprised in the polypeptide are proline residues.

The polypeptide may comprise a plurality of amino acid repeats, wherein said repeat consists of proline and alanine residues and wherein no more than 6 consecutive amino acid residues are identical. Particularly, the polypeptide may comprise or consist of the amino acid sequence AAPAA-PAPAAPAAPAPAAPA (SEQ ID NO: 5) or circular permuted versions or (a) multimers(s) of the sequences as a whole or parts of the sequence.

Preferably, the polypeptide comprises or consists of the amino acid sequence as shown in SEQ ID NO: 7 or 9, or the polypeptide comprises or consists of an amino acid sequence encoded by a nucleic acid having a nucleotide sequence as shown in SEQ ID NO: 8 or 10. It is preferred herein that the modified protein (a) comprises or consists of an amino acid sequence as shown in SEQ ID NO: 11 or 13; or (b) comprises or consists of an amino acid sequence encoded by a nucleic acid having a nucleotide sequence as shown in SEQ ID NO: 12 or 14. In one aspect, the polypeptide is a random coil polypeptide.

In some aspects, the modified protein, e.g. the fusion protein, has an asparaginase or glutaminase activity higher than that of the unconjugated L-asparaginase. For example, the modified proteins can have an asparaginase or glutaminase activity at least 5% and/or up to 30% (e.g. at least 10%, 15%, 20%, 25% (or more)) higher than that of the unmodified L-asparaginase, particularly as assessed by the Nessler assay. In further aspects, the L-asparaginase in the modified protein, e.g. in the fusion protein, is covalently linked to a terminal residue of the polypeptide directly by an amine bond, and/or the fusion protein is manufactured recombinantly. In preferred aspects, the modified protein, e.g. the fusion protein, includes a linker between the L-asparaginase and the polypeptide. An exemplary linker may be an alanine amino acid residue. The invention also relates to a pharmaceutical composition comprising the modified protein, e.g. the fusion protein, or its use in therapy, or for use as a medicament, or for use in medicine.

The invention also relates to a nucleic acid encoding the modified protein, particularly a fusion protein as defined herein. Preferably, the nucleic acid is selected from the group consisting of: (a) the nucleic acid molecule comprising the nucleotide sequence of SEQ ID NO: 12 or 14; (b) the nucleic acid molecule comprising the nucleotide sequence having at least 85% identity to the nucleotide sequence as defined in (a); and (c) the nucleic acid molecule being degenerate as a result of the genetic code to the nucleotide sequence as defined in (a).

One aspect of the invention further relates to a process for the preparation of a modified protein as defined herein or of a nucleic acid as defined herein. The process may comprise culturing a host cell as defined herein and isolating said modified protein from the culture or from said cell. The process of preparing the modified protein as defined herein, particularly the fusion protein, can comprise culturing a host cell transformed with or comprising a vector comprising a nucleic acid encoding the modified protein, particularly the fusion protein, under conditions causing expression of the modified protein, particularly of the fusion protein. In some aspects, the host cell is selected from the group recited above.

The invention further relates to a method of treating a disease treatable by L-asparagine depletion in a patient, said method comprising administering to said patient an effective amount of the modified protein as defined herein, e.g. the fusion protein. The disease treatable by L-asparagine depletion may be a cancer. The modified protein as defined herein may elicit a lower immunogenic response in the patient compared to unconjugated L-asparaginase, may have a longer in vivo circulating half-life after a single dose compared to the unconjugated L-asparaginase, and/or may have a greater AUC value after a single dose compared to the L-asparaginase (particularly the unconjugated L-asparaginase).

The problem to be solved by the invention can be seen to be the provision of an L-asparaginase preparation with: high in vitro bioactivity; a stable protein-modifier linkage; prolonged in vivo half-life; significantly reduced immunogenicity, as evidenced, for example, by the reduction or elimination of an antibody response against the L-asparaginase preparation following repeated administrations; and/or usefulness as a second-line therapy for patients who have developed sensitivity to first-line therapies using, e g, non-*E. coli*-derived L-asparaginases.

This problem is solved according to the present invention by the embodiments characterized in the claims, in particular by providing a modified protein comprising an L-asparaginase and a modifier, i.e. (ii) one or more (poly)peptide(s), wherein the (poly)peptide consists solely of proline and alanine amino acid residues, and by providing methods for preparing and using the same.

In one aspect, described herein is a modified L-asparaginase with improved pharmacological properties as compared with the unmodified L-asparaginase protein.

The term "modified L-asparaginase" as used herein refers to "a modified protein comprising (i) L-asparaginase and (ii) one or more (poly)peptide(s), wherein the (poly)peptide consists solely of proline and alanine amino acid residues" as defined and described herein. In one aspect of the invention the L-asparaginase is derived from *Erwinia* having at least 85% identity to the amino acid of SEQ ID NO: 1.

The modified L-asparaginase described herein, e.g., L-asparaginase conjugated or fused to one or more (poly) peptide(s), wherein the (poly)peptide consists solely of proline and alanine amino acid residues, serves as a therapeutic agent particularly for use in patients who show hypersensitivity (e.g., an allergic reaction or silent hypersensitivity) to treatment with L-asparaginase or PEGylated L-asparaginase from *Erwinia* and/or *E. coli*, or unmodified L-asparaginase from *Erwinia*. The modified L-asparaginase described herein is also useful as a therapeutic agent for use in patients who have had a disease relapse, e.g., a relapse of ALL, and have been previously treated with another form of asparaginase.

*Erwinia chrysanthemi* (also known as *Pectobacterium chrysanthemi*) has been renamed *Dickeya chrysanthemi*. Thus, the terms *Erwinia chrysanthemi*, *Pectobacterium chrysanthemi* and *Dickeya chrysanthemi* are used interchangeably herein.

Unless otherwise expressly defined, the terms used herein will be understood according to their ordinary meaning in the art.

As used herein, the term "including" means "including, without limitation," and terms used in the singular shall include the plural, and vice versa, unless the context dictates otherwise.

As used herein, the terms "comprising", "including", "having" or grammatical variants thereof are to be taken as specifying the stated features, integers, steps or components but do not preclude the addition of one or more additional features, integers, steps, components or groups thereof. The terms "comprising"/"including"/"having" encompass the terms "consisting of" and "consisting essentially of". Thus, whenever the terms "comprising"/"including"/"having" are used herein, they can be replaced by "consisting essentially of" or, preferably, by "consisting of".

The terms "comprising"/"including"/"having" mean that any further component (or likewise features, integers, steps and the like) can be present.

The term "consisting of" means that no further component (or likewise features, integers, steps and the like) can be present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed product, composition, device or method and the like.

Thus, the term "consisting essentially of" means that specific further components (or likewise features, integers, steps and the like) can be present, namely those not materially affecting the essential characteristics of the product, composition, device or method. In other words, the term "consisting essentially of" (which can be interchangeably used herein with the term "comprising substantially"), allows the presence of other components in the product, composition, device or method in addition to the mandatory components (or likewise features, integers, steps and the like), provided that the essential characteristics of the product, composition, device or method are not materially affected by the presence of other components.

As used herein, the term "about" refers to ±10%, unless indicated otherwise herein.

As used herein, "a" or "an" may mean one or more.

As used herein, the term "disease treatable by depletion of asparagine" refers to a condition or disorder wherein the cells involved in or responsible for the condition or disorder either lack or have a reduced ability to synthesize L-asparagine. Depletion or deprivation of L-asparagine can be partial or substantially complete (e.g., to levels that are undetectable using methods and apparatus that are known in the art).

As used herein, the term "therapeutically effective amount" refers to the amount of a protein (e.g., asparaginase or modified protein thereof), required to produce a desired therapeutic effect.

As used herein, the term, "L-asparaginase" is an enzyme with L-asparagine aminohydrolase activity. L-asparaginase's enzymatic activity may include not only deamidation of asparagine to aspartic acid and ammonia, but also deamidation of glutamine to glutamic acid and ammonia. Asparaginases are typically composed of four monomers (although some have been reported with five or six). Each monomer can be about 32,000 to about 36,000 daltons.

Many L-asparaginase proteins have been identified in the art, isolated by known methods from microorganisms. (See, e.g., Savitri and Azmi, Indian *J. Biotechnol* 2 (2003) 184-194, incorporated herein by reference in its entirety). The most widely used and commercially available L-asparaginases are derived from *E. coli* or from *Erwinia chrysanthemi*, both of which share 50% or less structural homology.

The following relates to "L-asparaginase" to be used in accordance with the invention. Within the *Erwinia* species, typically 75-77% sequence identity was reported between *Erwinia chrysanthemi* and *Erwinia carotovora*-derived enzymes, and approximately 90% sequence identity was found between different subspecies of *Erwinia chrysanthemi* (Kotzia (2007), *Journal of Biotechnology* 127, 657-669, incorporated herein by reference in its entirety). Some representative *Erwinia* L-asparaginases include, for example, those provided in Table 1 below which discloses percent sequence identity to *Erwinia Chrysanthemi* NCPPB 1066:

TABLE 1

| Species | Accession No. | % Identity |
|---|---|---|
| *Erwinia chrysanthemi* 3937 | AAS67028 | 91% |
| *Erwinia chrysanthemi* NCPPB 1125 | CAA31239 | 98% |
| *Erwinia carotovora* subsp. *atroseptica* | AAS67027 | 75% |
| *Erwinia carotovora* | AAP92666 | 77% |

The sequences of the *Erwinia* L-asparaginases and the GenBank entries of Table 1 are herein incorporated by reference. Exemplary L-asparaginases used in therapy are L-asparaginase isolated from *E. coli* and from *Erwinia*, specifically, *Erwinia chrysanthemi*.

The L-asparaginases may be native enzymes isolated from the microorganisms. They can also be produced by recombinant enzyme technologies in producing microorganisms such as *E. coli*. As examples, the protein used in the modified protein of the invention can be a recombinant protein produced in an *E. coli* strain, preferably a protein from an *Erwinia* species, particularly *Erwinia chrysanthemi*, produced in a recombinant *E. coli* strain.

Enzymes can be identified by their specific activities. This definition thus includes all polypeptides that have the defined specific activity also present in other organisms, more particularly in other microorganisms. Often enzymes with similar activities can be identified by their grouping to certain families defined as PFAM or COG. PFAM (protein family database of alignments and hidden Markov models; pfam.xfam.org) represents a large collection of protein sequence alignments. Each PFAM makes it possible to visualize multiple alignments, see protein domains, evaluate distribution among organisms, gain access to other databases, and visualize known protein structures. COGs (Clusters of Orthologous Groups of proteins; ncbi.nlm.nih.gov/COG/) are obtained by comparing protein sequences from 43 fully sequenced genomes representing 30 major phylogenetic lines. Each COG is defined from at least three lines, which permits the identification of former conserved domains.

The means of identifying percentage sequence identity are well known to those skilled in the art, and include in particular the BLAST programs, which can be used from the website blast.ncbi.olo.nih.gov/Blast.cgi with the default parameters indicated on that website. The sequences obtained can then be exploited (e.g., aligned) using, for example, the program CLUSTALW (ebi.ac.uk/Tools/clustalw2/index.html) with the default parameters. Using the references given on GenBank for known genes, those skilled in the art are able to determine the equivalent genes in other organisms, bacterial strains, yeasts, fungi, mammals, plants, etc. This routine work is advantageously done using consensus sequences that can be determined by carrying out sequence alignments with genes derived from other microorganisms, and designing degenerate probes to clone the corresponding gene in another organism.

The person skilled in the art will understand how to select and design proteins retaining substantially their L-asparaginase activity. One approach for the measuring L-asparaginase activity is a Nessler assay as described by Mashburn (1963) *Biochem. Biophys. Res. Commun.* 12, 50 (incorporated herein by reference in its entirety).

In a particular aspect of the modified protein of the invention, the L-asparaginase has at least about 85% homology or sequence identity to the amino acid sequence of SEQ ID NO: 1, more specifically at least about 85%, 86%, 87%, 88%, 89%, 90%, 91%, 92%, 93%, 94%, 95%, 96%, 97%, 98%, 99%, or 100% homology or sequence identity to the amino acid sequence of SEQ ID NO:1 as set forth in the attached sequence listing. The terms "homology" and "sequence identity" are used interchangeably herein.

The term "comprising the sequence of SEQ ID NO:1" (e.g. if the L-asparaginase has 100% homology or sequence identity to the amino acid sequence of SEQ ID NO: 1) means that the amino-acid sequence of the asparaginase may not be strictly limited to SEQ ID NO:1 but may contain one, two, three, four, five, six, seven, eight, nine, ten or more additional amino-acids. In other words, if the L-asparaginase to be used herein has 100% homology or sequence identity to the amino acid sequence of SEQ ID NO: 1, the L-asparaginase can comprise or consist of the amino acid sequence of SEQ ID NO: 1. The term "comprising" means in this context that the amino acid sequence of the L-asparaginase of SEQ ID NO: 1 may contain one, two, three, four, five, six, seven, eight, nine, ten or more additional amino-acids.

In a particular aspect, the protein is the L-asparaginase of *Erwinia chrysanthemi* comprising or consisting of the sequence of SEQ ID NO: 1. In another aspect, the L-asparaginase is from *Erwinia chrysanthemi* NCPPB 1066 (Genbank Accession No. CAA32884, incorporated herein by reference in its entirety), either with or without signal peptides and/or leader sequences.

Fragments of the L-asparaginase, preferably the L-asparaginase of SEQ ID NO:1, are also comprised within the definition of the L-asparaginase used in the modified protein of the invention. The term "a fragment of asparaginase" (e.g. a fragment of the asparaginase of SEQ ID NO: 1) means that the sequence of the asparaginase may include less amino-acid than in the asparaginases exemplified herein (e.g. the asparaginase of SEQ ID NO: 1) but still enough amino-acids to confer L-aminohydrolase activity. For example, the "fragment of asparaginase" is a fragment that is/consists of at least about 150 or 200 contiguous amino acids of one of the asparaginases exemplified herein (e.g. the asparaginase of SEQ ID NO: 1) (e.g. about 150, 160, 170, 180, 190, 200, 210, 220, 230, 240, 250, 260, 270, 280, 290, 300, 310, 320, 321, 322, 323, 324, 325, 326 contiguous amino acids) and/or wherein said fragment has up to 50 amino acids deleted from the N-terminus of said asparaginase exemplified herein (e.g. the asparaginase of SEQ ID NO: 1) (e.g. up to 1, 2, 3, 4, 5, 6, 7, 8, 9, 10, 15, 20, 25, 30, 35, 40, 45, or 50) and/or has up to up to 75 or 100 amino acids deleted from the C-terminus of said asparaginase exemplified herein (e.g. the asparaginase of SEQ ID NO: 1) (e.g. up to 1, 2, 3, 4, 5, 6, 7, 8, 9, 10, 15, 20, 25, 30, 35, 40, 45, 50, 55, 60, 70, 75, 80, 85, 90, 95 or 100) and/or has deleted amino acids at both the N-terminus and the C-terminus of said asparaginase exemplified herein (e.g. the asparaginase of SEQ ID NO: 1), wherein the total number of amino acids deleted can be up to 125 or 150 amino acids.

It is well known in the art that a polypeptide can be modified by substitution, insertion, deletion and/or addition of one or more amino-acids while retaining its enzymatic activity. The term "one or more amino acids" in this context can refer to one, two, three, four, five, six, seven, eight, nine, ten or more amino acids. For example, substitution of one amino-acid at a given position by a chemically equivalent amino-acid that does not affect the functional properties of a protein is common Substitutions may be defined as exchanges within one of the following groups:

Small aliphatic, non-polar or slightly polar residues: Ala, Ser, Thr, Pro, Gly

Polar, negatively charged residues and their amides: Asp, Asn, Glu, Gln

Polar, positively charged residues: His, Arg, Lys

Large aliphatic, non-polar residues: Met, Leu, Ile, Val, Cys

Large aromatic residues: Phe, Tyr, Trp.

Thus, changes that result in the substitution of one negatively charged residue for another (such as glutamic acid for aspartic acid) or one positively charged residue for another (such as lysine for arginine) can be expected to produce a functionally equivalent product.

The positions where the amino-acids are modified and the number of amino-acids subject to modification in the amino-acid sequence are not particularly limited. The skilled artisan is able to recognize the modifications that can be introduced without affecting the activity of the protein. For example, modifications in the N- or C-terminal portion of a protein may be expected not to alter the activity of a protein under certain circumstances. With respect to asparaginases, in particular, much characterization has been done, particularly with respect to the sequences, structures, and the residues forming the active catalytic site. This provides guidance with respect to residues that can be modified without affecting the activity of the enzyme. All known L-asparaginases from bacterial sources have common structural features. All are homotetramers with four active sites between the N- and C-terminal domains of two adjacent monomers (Aghaipour (2001) *Biochemistry* 40, 5655-5664, incorporated herein by reference in its entirety). All have a high degree of similarity in their tertiary and quaternary structures (Papageorgiou (2008) *FEBS J.* 275, 4306-4316, incorporated herein by reference in its entirety). The sequences of the catalytic sites of L-asparaginases are highly conserved between *Erwinia chrysanthemi*, *Erwinia carotovora*, and *E. coli* L-asparaginase II (Id). The active site flexible loop contains amino acid residues 14-33, and structural analysis show that Thr15, Thr95, Ser62, Glu63, Asp96, and Ala120 contact the ligand (Id). Aghaipour et al. have conducted a detailed analysis of the four active sites of *Erwinia chrysanthemi* L-asparaginase by examining high resolution crystal structures of the enzyme complexed with its substrates (Aghaipour (2001) *Biochemistry* 40, 5655-5664). Kotzia et al. provide sequences for L-asparaginases from several species and subspecies of *Erwinia* and, even though the proteins have only about 75-77% identity between *Erwinia chrysanthemi* and *Erwinia carotovora*, they each still have L-asparaginase activity (Kotzia (2007) *J. Biotechnol.* 127, 657-669). Moola et al performed epitope mapping studies of *Erwinia chrysanthemi* 3937 L-asparaginase and were able to retain enzyme activity even after mutating various antigenic sequences in an attempt to reduce immunogenicity of the asparaginase (Moola (1994) *Biochem. J.* 302, 921-927). In view of the extensive characterization that has been performed on L-asparaginases, one of skill in the art could determine how to make fragments and/or sequence substitutions while still retaining enzyme activity.

As used herein, the term "about" modifying, for example, the dimensions, volumes, quantity of an ingredient in a composition, concentrations, process temperature, process time, yields, flow rates, pressures, and like values, and ranges thereof, refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods; and like considerations. The term "about" also encompasses amounts that differ due to aging of, for example, a composition, formulation, or cell culture with a particular initial concentration or mixture, and amounts that differ due to mixing or processing a composition or formulation with a particular initial concentration or mixture. Whether modified by the term "about" the claims appended hereto include equivalents to these quantities. The term "about" further may refer to a range of values that are similar to the stated reference value. In certain embodiments, the term "about" refers to a range of values that fall within 10, 9, 8, 7, 6, 5, 4, 3, 2, 1 percent or less of the stated reference value.

In the context of the present invention, it has surprisingly been found that the chemical conjugation of one or more peptides consisting solely of proline and alanine amino acid residues via a specific C-terminal amino acid residue ($R^C$) to L-asparaginase allows to provide an L-asparaginase modified protein having a particularly high coupling ratio of said peptides per molecule of asparaginase and, thus, a considerably reduced immunogenicity and enhanced plasma half-life. It has further been found that this novel technique can also be applied to L-asparaginase without impairing its catalytic activity, which greatly enhances the therapeutic value of the corresponding modified proteins described herein.

In one aspect, described herein is a modified protein comprising (i) an L-asparaginase having at least 85, 90, 91, 92, 93, 94, 95, 96, 97, 98, 99 or 100% identity to the amino acid sequence of SEQ ID NO: 1 and (ii) one or more peptide(s), wherein the peptide consists solely of proline and alanine amino acid residues.

In a preferred aspect, the modified protein is a modified protein of L-asparaginase and one or more peptide(s), wherein each is independently a peptide $R^N$-(P/A)-$R^C$, wherein (P/A) is an amino acid sequence consisting solely of proline and alanine amino acid residues, wherein $R^N$ is a protecting group attached to the N-terminal amino group of the amino acid sequence, and wherein $R^C$ is an amino acid residue bound via its amino group to the C-terminal carboxy group of the amino acid sequence, wherein each peptide is conjugated to the L-asparaginase via an amide linkage formed from the carboxy group of the C-terminal amino acid residue $R^C$ of the peptide and a free amino group of the L-asparaginase, and wherein at least one of the free amino groups, which the peptides are conjugated to, is not an N-terminal α-amino group of the L-asparaginase.

In some aspect, the monomer of the modified protein has from about 350, 400, 450, 500, amino acids to about 550, 600, 650, 700, or 750 amino acids after modification. In additional aspects, the modified protein has from about 350 to about 750 amino acids, or about 500 to about 750 amino acids.

Each peptide that is comprised in the modified protein as described herein is independently a peptide $R^N$-(P/A)-$R^C$. Accordingly, for each of the peptides comprised in a modified protein described herein, the N-terminal protecting group $R^N$, the amino acid sequence (P/A), and the C-terminal amino acid residue $R^C$ are each independently selected from their respective meanings. The two or more peptides comprised in the modified protein may thus be the same, or they may be different from one another. In one aspect, all of the peptides comprised in the modified protein are the same.

Furthermore, the peptides comprised in the modified protein preferably adopt a random coil conformation, particularly when the modified protein is present in an aqueous environment (e.g., an aqueous solution or an aqueous buffer). The presence of a random coil conformation can be determined using methods known in the art, in particular by means of spectroscopic techniques, such as circular dichroism (CD) spectroscopy.

The moiety (P/A) in the chemically conjugated modified protein, which is comprised in the peptide $R^N$-(P/A)-$R^C$, is an amino acid sequence that can consist of a total of between 10 to 100 or more proline and alanine amino acid residues, a total of 15 to 60 proline and alanine amino acid residues, a total of 15 to 45 proline and alanine amino acid residues, e.g. a total of 20 to about 40 proline and alanine amino acid residues, e.g. 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 proline and alanine amino acid residues. In a preferred aspect, said amino acid sequence consists of about 20 proline and alanine amino acid residues. In another preferred aspect, said amino acid sequence consists of about 40 proline and alanine amino acid residues. In the peptide $R^N$-(P/A)-$R^C$, the ratio of the number of proline residues comprised in the moiety (P/A) to the total number of amino acid residues comprised in (P/A) is preferably ≥10% and ≤70%, more preferably ≥20% and ≤50%, and even more preferably ≥25% and ≤40%. Accordingly, it is preferred that 10% to 70% of the total number of amino acid residues in (P/A) are proline residues; more preferably, 20% to 50% of the total number of amino acid residues comprised in (P/A) are proline residues; and even more preferably, 25% to 40% (e.g., 25%, 30%, 35% or 40%) of the total number of amino acid residues comprised in (P/A) are proline residues. Moreover, it is preferred that (P/A) does not contain any consecutive proline residues (i.e., that it does not contain any partial sequence PP). In a preferred aspect, (P/A) is the amino acid sequence AAPAAPAPAAPAAPAPAAPA (SEQ ID NO: 5). In another preferred aspect, (P/A) is the amino acid sequence AAPAAPAPAAPAAPAPAAPAAAPAAPA-PAAPAAPAPAAPA (SEQ ID NO: 15).

The group $R^N$ in the peptide $R^N$-(P/A)-$R^C$ may be a protecting group which is attached to the N-terminal amino group, particularly the N-terminal α-amino group, of the amino acid sequence (P/A). It is preferred that $R^N$ is pyroglutamoyl or acetyl.

The group $R^C$ in the peptide $R^N$-(P/A)-$R^C$ is an amino acid residue which is bound via its amino group to the C-terminal carboxy group of (P/A), and which comprises at least two carbon atoms between its amino group and its carboxy group. It will be understood that the at least two carbon atoms between the amino group and the carboxy group of $R^C$ may provide a distance of at least two carbon atoms between the amino group and the carboxy group of $R^C$ (which is the case if, e.g., $R^C$ is an ω-amino-$C_{3-15}$ alkanoic acid, such as ε-aminohexanoic acid). It is preferred that $R^C$ is ε-aminohexanoic acid.

In one embodiment, the peptide is Pga-AAPAAPA-PAAPAAPAPAAPA-Ahx-COOH (SEQ ID NO: 16) or Pga-AAPAAPAPAAPAAPAPAAPAAAPAAPAPAAPAAPA-PAAPA-Ahx-COOH (SEQ ID NO: 17). The term "Pga" is an abbreviation of "pyroglutamoyl" or "pyroglutamic acid". The term "Ahx" is an abbreviation of "ε-aminohexanoic acid".

As also demonstrated in the appended examples, it has surprisingly been found that the use of a C-terminal amino acid residue $R^C$ as defined herein, including in particular ε-aminohexanoic acid, allows to provide modified proteins with an advantageously high coupling ratio of peptides consisting solely of proline and alanine amino acid residues per molecule of asparaginase and, thus, an advantageously reduced immunogenicity and an advantageously enhanced plasma half-life.

In the modified proteins as described herein, each peptide $R^N$-(P/A)-$R^C$, can be conjugated to the L-asparaginase via an amide linkage formed from the carboxy group of the C-terminal amino acid residue $R^C$ of the peptide and a free amino group of the L-asparaginase. A free amino group of the L-asparaginase may be, e.g., an N-terminal α-amino group or a side-chain amino group of the L-asparaginase (e.g., an ε-amino group of a lysine residue comprised in the L-asparaginase). If the L-asparaginase is composed of multiple subunits, e.g. if the L-asparaginase is a tetramer, there may be multiple N-terminal α-amino groups (i.e., one on each subunit). In one aspect, 9 to 13 peptides as defined herein (e.g. 9, 11, 12, or 13 peptides) can be chemically conjugated to the L-asparaginase (e.g. to each subunit/monomer of the L-asparaginase).

In accordance with the above, in one aspect at least one of the free amino groups, which the peptides are chemically conjugated to, is not (i.e., is different from) an N-terminal α-amino group of the L-asparaginase. Accordingly, it is preferred that at least one of the free amino groups, which the peptides are conjugated to, is a side-chain amino group of the L-asparaginase, and it is particularly preferred that at least one of the free amino groups, which the peptides are conjugated to, is an ε-amino group of a lysine residue of the L-asparaginase.

Moreover, it is preferred that the free amino groups, which the peptides are conjugated to, are selected from the ε-amino group(s) of any lysine residue(s) of the L-asparaginase, the N-terminal α-amino group(s) of the L-asparaginase or of any subunit(s) of the L-asparaginase, and any combination thereof. It is particularly preferred that one of the free amino groups, which the peptides are conjugated to, is an N-terminal α-amino group, while the other one(s) of the free amino groups, which the peptides are conjugated to, is/are each an ε-amino group of a lysine residue of the L-asparaginase. Alternatively, it is preferred that each of the free amino groups, which the peptides are conjugated to, is an ε-amino group of a lysine residue of the L-asparaginase.

The modified proteins as described herein are composed of L-asparaginase and one or more peptides as defined herein. A corresponding modified protein may, e.g., consist of one L-asparaginase and one, two, three, four, five, six, seven, eight, nine, ten, 15, 20, 25, 30, 35, 40, 45, 50, 55 (or more) peptides which are each conjugated to the L-asparaginase. The L-asparaginase may be, e.g., a monomeric protein or a protein composed of multiple subunits, e.g. a tetramer. If the L-asparaginase is a monomeric protein, a corresponding modified protein may, e.g., consist of one monomeric L-asparaginase and nine to thirteen (or more) (e.g. 9, 10, 11, 12, or 13), peptides which are each conjugated to the monomeric L-asparaginase. An exemplary amino acid sequence of a monomeric L-asparaginase is shown in SEQ ID NO: 1. If the L-asparaginase is a protein composed of multiple subunits, e.g. of four subunits (i.e. if said L-asparaginase is a tetramer), a corresponding modified protein may, e.g., consist of four L-asparaginase subunits and nine to thirteen (or more) (e.g. 9, 10, 11, 12, or 13), peptides as defined herein which are each conjugated to each subunit of the L-asparaginase. An exemplary amino acid sequence of a subunit of L-asparaginase is shown in SEQ ID NO: 1. Likewise, if the L-asparaginase is a protein composed of multiple subunits, e.g. of four subunits (i.e. if said L-asparaginase is a tetramer), a corresponding modified protein may, e.g., consist of four L-asparaginase subunits and 30, 31, 32, 33, 34, 35, 36, 37, 38, 39, 40, 41, 42, 43, 44, 45, 46, 47, 48, 49, 50, 51, 52, 53, 54, 55 (or more) peptides which are each conjugated to the L-asparaginase tetramer. In one aspect the invention relates to a modified protein having an L-asparaginase and multiple chemically attached peptide sequences. In a further aspect the length of the peptide sequences are from about 10 to about 100, from about 15 to about 60 or from about 20 to about 40.

The peptide consisting solely of proline and alanine amino acid residues may be covalently linked to one or more amino acids of said L-asparaginase, such as lysine residues and/or N-terminal residue, and/or the peptide consisting solely of proline and alanine amino acid residues may be covalently linked to at least from about 40, 50, 60, 70, 80 or 90% to about 60, 70, 80, 90 or 100% of the accessible amino groups including amino groups of lysine residues and/or N-terminal residue on the surface of the L-asparaginase. For example, there may be about 11 to 12 lysine residues accessible per L-asparaginase, and about 9 to 12 lysines would be conjugated to the peptide consisting solely of proline and alanine amino acid residues. In further aspects, the peptide consisting solely of proline and alanine amino acid residues is covalently linked to from about 20, 30, 40, 50, or 60% to about 30, 40, 50, 60, 70, 80 or 90% of total lysine residues of said L-asparaginase. In further embodiments, the peptide consisting solely of proline and alanine amino acid residues is covalently linked to the L-asparaginase via a linker. Exemplary linkers include linkers disclosed in U.S. Patent Application Publication No. 2015/0037359, which is herein incorporated by reference in its entirety.

In addition, said modified protein may have a half-life of at least about 5, 10, 12, 15, 24, 36, 48, 60, 72, 84 or 96 hours at a dose of about 25 µg protein/kg, and/or a longer in vivo circulating half-life compared to the unmodified L-asparaginase. Moreover, said modified protein may have a greater area under the plasma drug concentration-time curve (AUC) compared to the L-asparaginase.

The modified protein according to the present invention can be prepared using methods known in the art. In particular, it can be prepared using the process described in the following, and/or in accordance with or in analogy to the procedures described in the examples.

The invention further relates to a process of preparing a modified protein as defined herein, the process comprising: (a) coupling an activated peptide of the formula $R^N$-(P/A)-$R^{C-act}$, wherein $R^{C-act}$ is a carboxy-activated form of $R^C$, wherein $R^C$ and (P/A) are as defined in the modified protein to be prepared, and wherein $R^N$ is a protecting group which is attached to the N-terminal amino group of (P/A), with L-asparaginase to obtain a modified protein of the L-asparaginase and peptides in which $R^N$ is a protecting group.

The carboxy-activated C-terminal amino acid residue $R^{C-act}$, which is comprised in activated peptide, may be any amino acid residue $R^C$, as described and defined herein with respect to the peptide, wherein the carboxy group of $R^C$ is in the form of an activated carboxy group. Preferably, the activated carboxy group of the amino acid residue $R^{C-act}$ in the activated peptide is an active ester group.

If the activated carboxy group of $R^{C-act}$ is an active ester group, it is preferably selected from any one the following active ester groups:

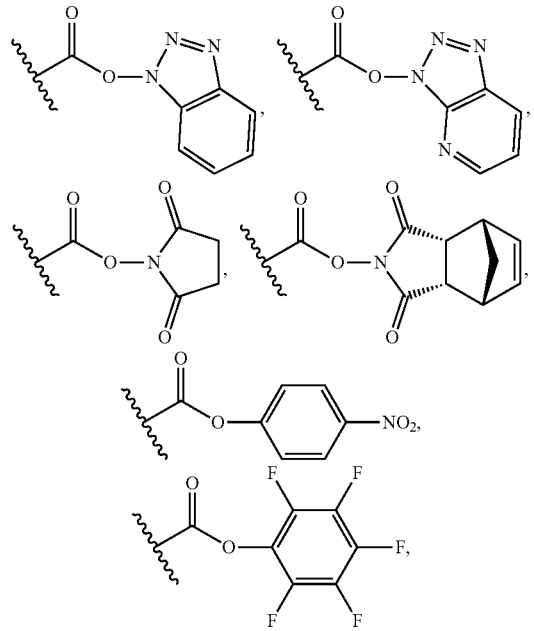

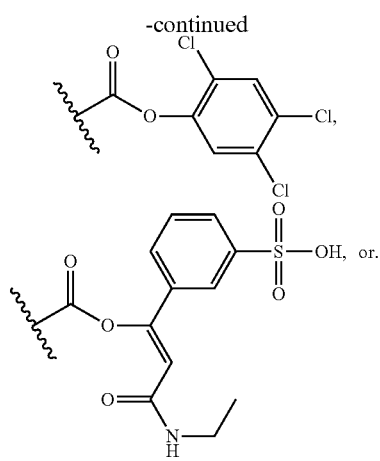

A particularly preferred active ester group is a 1-hydroxybenzotriazole (HOBt) active ester group. Accordingly, it is particularly preferred that the activated carboxy group of $R^{C-act}$ is a group of the following formula:

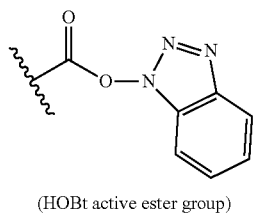 [SMILES: *C(=O)On1nnc2ccccc21]

(HOBt active ester group)

The process may additionally comprise, before step (a), a further step of converting a peptide of the formula $R^N$-(P/A)-$R^C$, wherein $R^C$ and (P/A) are as defined in the modified protein to be prepared, and wherein $R^N$ is a protecting group which is attached to the N-terminal amino group of (P/A), into the activated P/A peptide.

For example, in order to obtain an activated peptide having a 1-hydroxybenzotriazole active ester group as the activated carboxy group of $R^{C-act}$, the step of converting the peptide into the activated peptide can be conducted by reacting the peptide with a salt of a phosphonium, uronium or immonium ester of 1-hydroxybenzotriazole (HOBt) in the presence of a base. The salt of the phosphonium, uronium or immonium derivative of HOBt is preferably O-(benzotriazol-1-yl)-1,1,3,3-tetramethyluronium tetrafluoroborate (TBTU).

The coupling step (a) and the preceding optional step of converting a peptide into an activated peptide can be conducted, e.g., using any of the peptide coupling or amide bond formation procedures described in the literature, e.g., in any of: El-Faham et al., (2011) Chem Rev. 111(11), 6557-6602; Montalbetti et al., (2005) Tetrahedron, 61(46), 10827-10852; Klose et al. (1999) Chem. Commun. 18, 1847-1848; Carpino et al. (1995) J. Am. Chem. Soc. 117(19), 5401-5402); Valeur et al., (2009) Chem. Soc. Rev., 38(2), 606-631; or Hermanson, (2013) Bioconjugate techniques. Third edition. Academic press. Suitable reagents and reaction conditions for such procedures are further described in the aforementioned literature and in the further references cited therein. Additional descriptions are found in U.S. Pat. Nos. 8,563,521; 9,260,494; and 9,221,882, all of which are incorporated by references herein in their entirety.

Procedures for removing the protecting groups $R^N$, as required in the optional step (b), are well-known in the art and are described, e.g., in Wuts et al., (2012) Greene's Protective Groups in Organic Synthesis. Fourth Edition. John Wiley & Sons, and/or in Isidro-Llobet et al., (2009) Chem. Rev. 109(6), 2455-2504. The optional step (b) can thus be conducted, e.g., as described for the corresponding protecting group $R^N$ in any of the aforementioned references.

In some aspects, the invention relates to a modified protein comprising (i) an L-asparaginase having at least 85, 90, 91, 92, 93, 94, 95, 96, 97, 98, 99 or 100% identity to the amino acid sequence of SEQ ID NO: 1 and (ii) and a polypeptide, wherein the polypeptide consists solely of proline and alanine amino acid residues. In one aspect, the modified protein is a fusion protein. The polypeptide consisting solely of proline and alanine amino acid residues may have a length of about 200 to about 400 proline and alanine amino acid residues. In other words the polypeptide may consist of about 200 to about 400 proline and alanine amino acid residues. In a preferred aspect, the polypeptide consists of a total of about 200 (e.g. 201) proline and alanine amino acid residues (i.e. has a length of about 200 (e.g. 201) proline and alanine amino acid residues) or the polypeptide consists of a total of about 400 (e.g. 401) proline and alanine amino acid residues (i.e. has a length of about 400 (e.g. 401) proline and alanine amino acid residues). In some preferred embodiments, the polypeptide comprises or consists of an amino acid sequence as shown in SEQ ID NO: 7 or 9; or the polypeptide comprises or consists of an amino acid sequence encoded by a nucleic acid having a nucleotide sequence as shown in SEQ ID NO: 8 or 10. In some aspects, the modified protein, preferably wherein the modified protein is a fusion protein, and each monomer has from about 350, 400, 450, 500, amino acids to about 550, 600, 650, 700, 750 or 1,000 amino acids including the monomer and the P/A amino acid sequence. In additional aspects, the modified protein has from about 350 to about 800 amino acids or about 500 to about 750 amino acids.

For example, the polypeptide includes the peptides prepared in U.S. Pat. No. 9,221,882.

In a preferred aspect, the modified protein (a) comprises or consists of an amino acid sequence as shown in SEQ ID NO: 11 or 13; or (b) comprises or consists of an amino acid sequence encoded by a nucleic acid having a nucleotide sequence as shown in SEQ ID NO: 12 or 14. It is contemplated herein that the modified protein comprises (a) a protein having an amino acid sequence as shown in SEQ ID NO: 11 or 13; (b) a protein as defined in (a) wherein one to 65 amino acids are deleted, inserted, added or substituted in the asparaginase; (c) a protein encoded by a nucleic acid having a nucleotide sequence as shown in SEQ ID NO: 12 or 14; (d) a protein having an amino acid sequence encoded by a nucleic acid hybridizing under stringent conditions to the complementary strand of nucleic acid molecules as defined in (c); (e) a protein having at least 85% identity to the protein of any one of (a) to (d); and (f) a protein having an amino acid sequence encoded by a nucleic acid being degenerate as a result of the genetic code to the nucleotide sequence of a nucleic acid as defined in (c) or (d).

The modified protein as defined herein may be composed of four subunits, wherein the subunits are selected from the group consisting of (a) a protein having an amino acid sequence as shown in SEQ ID NO: 1; (b) a protein as defined in (a) wherein one to 65 amino acids are deleted, inserted, added or substituted in the asparaginase; (c) a protein encoded by a nucleic acid molecule having a nucleotide sequence as shown in SEQ ID NO: 2; (d) a protein having an amino acid sequence encoded by a nucleic acid hybridizing under stringent conditions to the complementary strand of nucleic acid molecules as defined in (c); (e) a protein having at least 85% identity to the protein of any one of (a) to (d); and (f) a protein having an amino acid sequence encoded by a nucleic acid being degenerate as a result of the genetic code to the nucleotide sequence of a nucleic acid as defined in (c) or (d).

The invention relates to a nucleic acid encoding the modified protein as defined herein, specifically if the modified protein is a modified protein of the L-asparaginase and a polypeptide, wherein the polypeptide consists solely of proline and alanine amino acid residues. In a preferred aspect, the modified protein is a fusion protein. In a preferred aspect, the nucleic acid is selected from the group consisting of: (a) the nucleic acid comprising the nucleotide sequence of SEQ ID NO: 12 or 14; (b) the nucleic acid comprising the nucleotide sequence having at least 85% identity to the nucleotide sequence as defined in (a); and (c) the nucleic acid being degenerate as a result of the genetic code to the nucleotide sequence as defined in (a).

In a further aspect, the invention relates to a nucleotide sequence encoding the fusion protein, including a nucleotide sequence having at least 85, 90, 91, 92, 93, 94, 95, 96, 97, 98, 99 or 100% identity to the nucleotide sequence selected from the group consisting of SEQ ID NO: 12 or 14. While the encoded polypeptide comprises a repetitive amino acid sequence that may form a random coil, the encoding nucleic acid comprises preferably a low repetitive nucleotide sequences. In other words, the nucleic acid can comprise a nucleotide sequence encoding a PA-rich polypeptide, wherein said coding nucleotide sequence comprises nucleotide repeats having a maximum length of 14, 15, 16, 17, about 20, about 25, about 30, about 35, about 40, about 45, about 50 or about 55 nucleotides. The low repetitive nucleic acid as disclosed herein can be advantageous compared to highly repetitive nucleic acid molecules. In particular, the genetic stability of the low repetitive nucleic acid molecules to be used herein can be improved.

In some aspects, the nucleotide sequence is a sequence encoding any of the modified proteins comprising the L-asparaginase and a polypeptide, wherein the polypeptide consists solely of proline and alanine amino acid residues, preferably wherein the modified protein is a fusion protein, described herein, except that one or more amino acid is added, deleted, inserted or substituted, with the proviso that the fusion protein having this amino acid sequence has L-asparaginase activity.

In additional aspects, the invention relates to a (recombinant) vector comprising the nucleotide sequence encoding the modified protein comprising the L-asparaginase and a polypeptide, wherein the polypeptide consists solely of proline and alanine amino acid residues, preferably wherein the modified protein is a fusion protein, as described herein, wherein the vector can express the modified protein (e.g. fusion protein). In further aspects, the invention also relates to a host comprising the (recombinant) vector described herein. The host may be yeasts, such as *Saccharomyces cerevisiae* and *Pichia Pistoris*, bacteria, actinomycetes, fungi, algae, and other microorganisms, including *Escherichia coli*, *Bacillus* sp., *Pseudomonas fluorescens*, *Corynebacterium glutamicum* and bacterial hosts of the following genuses, *Serratia*, *Proteus*, *Acinetobacter* and *Alcaligenes*. Other hosts are known to those of skill in the art, including *Nocardiopsis alba*, which expresses a variant of Asparaginase lacking on glutaminase-activity (Meena et al. (2014) *Bioprocess Biosyst. Eng.* October 2014 Article, which is incorporated by reference herein in its entirety), and those disclosed in Savitri et al. (2003) *Indian Journal of Biotechnology*, 2, 184-194, which is incorporated by reference herein in its entirety.

The present invention relates to a vector comprising the nucleic acid as described herein above, i.e. a nucleic acid encoding the modified protein as defined herein, particularly a modified protein of the L-asparaginase and a polypeptide, wherein the polypeptide consists solely of proline and alanine amino acid residue, such as a fusion protein. In a preferred aspect, the nucleic acid is selected from the group consisting of: (a) the nucleic acid comprising the nucleotide sequence of SEQ ID NO: 12 or 14; (b) the nucleic acid comprising the nucleotide sequence having at least 85% identity to the nucleotide sequence as defined in (a); and (c) the nucleic acid being degenerate as a result of the genetic code to the nucleotide sequence as defined in (a).

The invention relates to a host cell comprising the nucleic acid as defined herein or comprising the vector as defined herein. Example hosts are listed above.

The invention further relates to a process of preparing the modified protein as described herein, preferably the fusion protein, or of the nucleic acid encoding same. The process can comprise culturing a host cell as defined herein and isolating said modified protein from the culture or from said cell. The process can comprise culturing a host cell (e.g. a host cell transformed with or a host cell comprising the nucleic acid and/or the vector comprising a nucleotide sequence encoding the modified protein (preferably the fusion protein) under a condition causing expression of the modified protein (preferably the fusion protein). Example hosts are listed above.

Many suitable vectors are known to those skilled in molecular biology. The choice of a suitable vector depends on the function desired, including plasmids, cosmids, viruses, bacteriophages and other vectors used conventionally in genetic engineering.

Methods which are well known to those skilled in the art can be used to construct various plasmids; see, for example, the techniques described in Sambrook (2012) Molecular Cloning: A Laboratory Manual, Cold Spring Harbor Laboratory Press. Typical plasmid vectors include, e.g., pQE-12, the pUCseries of plasmids, pBluescript (Stratagene), the pET series of expression vectors (Novagen) or pCRTOPO (Invitrogen), lambda gt11, pJOE, the pBBR1-MCS series, pJB861, pBSMuL, pBC2, pUCPKS, pTACT1. Typical vectors compatible with expression in mammalian cells inlcude E-027 pCAG Kosak-Cherry (L45a) vector system, pREP (Invitrogen), pCEP4 (Invitrogen), pMClneo (Stratagene), pXT1 (Stratagene), pSG5 (Stratagene), EBO-pSV2neo, pBPV-1, pdBPVMMTneo, pRSVgpt, pRSVneo, pSV2-dhfr, pIZD35, Okayama-Berg cDNA expression vector pcDV1 (Pharmacia), pRc/CMV, pcDNA1, pcDNA3 (Invitrogen), pcDNA3.1, pSPORT1 (GIBCO BRL), pGEMHE (Promega), pLXIN, pSIR (Clontech), pIRES-EGFP (Clontech), pEAK-10 (Edge Biosystems) pTriEx-Hygro (Novagen) and pCINeo (Promega). Non-limiting examples for plasmid vectors suitable for *Pichia pastoris* comprise e.g. the plasmids pAO815, pPIC9K and pPIC3.5K (all Invitrogen).

Generally, vectors can contain one or more origins of replication (ori) and inheritance systems for cloning or expression, one or more markers for selection in the host, e.g., antibiotic resistance, and one or more expression cassettes. Examples of suitable origins of replication include, for example, the full length ColE1, its truncated versions such as those present on the pUC plasmids, the SV40 viral and the M13 phage origins of replication. Non-limiting examples of selectable markers include ampicillin, chloramphenicol, tetracycline, kanamycin, dhfr, gpt, neomycin, hygromycin, blasticidin or geneticin. Further, said vector comprises a regulatory sequence that is operably linked to said nucleotide sequence or the nucleic acid molecule defined herein.

The coding sequence(s), e.g., said nucleotide sequence encoding the polypeptide, comprised in the vector can be linked to (a) transcriptional regulatory element(s) and/or to other amino acid encoding sequences using established methods. Such regulatory sequences are well known to those skilled in the art and include, without being limiting, regulatory sequences ensuring the initiation of transcription, internal ribosomal entry sites (IRES) and, optionally, regulatory elements ensuring termination of transcription and stabilization of the transcript. Non-limiting examples for such regulatory sequences ensuring the initiation of transcription comprise promoters, a translation initiation codon, enhancers, insulators and/or regulatory elements ensuring transcription termination. Further examples include Kozak sequences and intervening sequences flanked by donor and acceptor sites for RNA splicing, nucleic acid sequences encoding secretion signals or, depending on the expression system used, signal sequences capable of directing the expressed protein to a cellular compartment or to the culture medium.

Examples of suitable promoters include, without being limiting, the cytomegalovirus (CMV) promoter, SV40 promoter, RSV (Rous sarcoma virus) promoter, the lacZ promoter, chicken β-actin promoter, CAG promoter (a combination of chicken β-actin promoter and cytomegalovirus immediate-early enhancer), human elongation factor 1α, promoter, AOX1 promoter, GAL1 promoter, CaM-kinase promoter, the lac, trp or tac promoter, the lacUV5 promoter, the T7 or T5 promoter, the *Autographa californica* multiple nuclear polyhedrosis virus (AcMNPV) polyhedral promoter or a globin intron in mammalian and other animal cells. One example of an enhancer is, e.g., the SV40 enhancer. Non-limiting additional examples for regulatory elements/sequences ensuring transcription termination include the SV40 poly-A site, the tk poly-A site or the AcMNPV polyhedral polyadenylation signals.

Furthermore, depending on the expression system, leader sequences capable of directing the polypeptide to a cellular compartment or secreting it into the medium may be added to the coding sequence of the nucleic acid provided herein. The leader sequence(s) is (are) assembled in frame with translation, initiation and termination sequences, and preferably, a leader sequence is capable of directing secretion of translated protein, or a portion thereof, into the periplasmic space or into the extracellular medium. Suitable leader sequences are, for example, the signal sequences of BAP (bacterial alkaline phosphatase), CTB (cholera toxin subunit B), DsbA, ENX, OmpA, PhoA, stII, OmpT, PelB, Tat (Twin-arginine translocation) in *E. coli*, and the signal sequences of bovine growth hormone, human chymotrypsinogen, human factor VIII, human ig-kappa, human insulin, human interleukin-2, luciferase from Metrida or Vargula, human trypsinogen-2, inulinase from *Kluyveromyces marxianus*, mating factor alpha-1 from *Saccharomyces cerevisiae*, mellitin, human azurocidin and the like in eukaryotic cells.

The vectors may also contain an additional expressible nucleic acid sequence coding for one or more chaperones to facilitate correct protein folding.

In some aspects, the vector of the present invention is an expression vector. An expression vector is capable of directing the replication and the expression of the nucleic acid molecule of the invention, e.g., the nucleic acid comprising the nucleotide sequence encoding the polypeptide and the nucleotide sequence encoding asparaginase.

The nucleic acid molecules and/or vectors as described herein above may be designed for introduction into cells by, e.g., non-chemical methods (electroporation, sonoporation, optical transfection, gene electrotransfer, hydrodynamic delivery or naturally occurring transformation upon contacting cells with the nucleic acid molecule of the invention), chemical-based methods (calcium phosphate, DMSO, PEG, liposomes, DEAE-dextrane, polyethylenimine, nucleofection etc.), particle-based methods (gene gun, magnetofection, impalefection), phage or phagemid vector-based methods and viral methods. For example, expression vectors derived from viruses such as retroviruses, vaccinia virus, adeno-associated virus, herpes viruses, Semliki Forest Virus or bovine papilloma virus, may be used for delivery of the nucleic acid molecules into a targeted cell population.

The present invention also relates to a host cell or a non-human host transformed with a vector or the nucleic acid described herein. It will be appreciated that the term "host cell or a non-human host transformed with the vector" relates to a host cell or a non-human host that comprises the vector or the nucleic acid as described herein. Host cells for the expression of polypeptides are well known in the art and comprise prokaryotic cells as well as eukaryotic cells. Appropriate culture media and conditions for the above described host cells are known in the art.

"Culturing the host or host cell" includes expression of the modified protein, including as a fusion protein, as defined herein and/or the polypeptide as defined herein and/or of the asparaginase in the host or host cell.

Methods for the isolation of the modified protein and/or the polypeptide as defined herein and/or of the asparaginase comprise, without limitation, purification steps such as affinity chromatography (preferably using a fusion tag such as the Strep-tag II or the $His_6$-tag), gel filtration (size exclusion chromatography), anion exchange chromatography, cation exchange chromatography, hydrophobic interaction chromatography, high pressure liquid chromatography (HPLC), reversed phase HPLC, ammonium sulfate precipitation or immunoprecipitation. These methods are well known in the art and have been generally described, e.g., in Scopes (1994) Protein Purification—Principles and Practice, Springer. Such methods provide substantially pure polypeptides. Said pure polypeptides have a homogeneity of, preferably, at least about 90 to 95% (on the protein level), more preferably, at least about 98 to 99%. Most preferably, these pure polypeptides are suitable for pharmaceutical use/applications.

It is envisaged herein that, a modified protein comprising L-asparaginase and the polypeptide can be prepared by expressing the nucleic acid molecule comprising the nucleotide sequence encoding the polypeptide and the nucleic acid sequence encoding the asparaginase. The expressed modified protein can be isolated. Alternatively, the modified protein can be prepared by culturing/raising the host comprising the nucleotide sequence or the nucleic acid molecule encoding said polypeptide consisting solely of proline and alanine. Thus, the nucleic acid is expressed in the host. The produced polypeptide can be isolated. The produced polypeptide can be conjugated to the asparaginase, e.g., via a peptide bond or a non-peptide bond.

The modified proteins described herein can be used in the treatment of a disease treatable by depletion of asparagine.

The disease treatable by depletion of asparagines is preferably cancer, such as non-solid cancer. Preferably, the non-solid cancer is leukemia or non-Hodgkin's lymphoma. The leukemia preferably is acute lymphoblastic leukemia (ALL) or acute myeloid leukemia (AML). For example, the modified proteins are useful in the treatment or the manufacture of a medicament for use in the treatment of acute lymphoblastic Leukemia (ALL) in both adults and children or acute myeloid leukemia (AML) in both adults and children. The use of the modified proteins described herein in the treatment of other conditions where asparagine depletion is expected to have a useful effect is contemplated. Such conditions include, but are not limited to the following: malignancies, or cancers, including but not limited to hematalogic malignancies, NK lymphoma, pancreatic cancer, Hodgkin's disease, acute myelocytic Leukemia, acute myelomonocytic Leukemia, chronic lymphocytic Leukemia, lymphosarcoma, reticulosarcoma, melanosarcoma, and diffuse large B-cell lymphoma (DLBCL). The cancer may be a solid cancer, e.g. lung cancer or breast cancer. Representative non-malignant hematologic diseases which respond to asparagine depletion include immune system-mediated Blood diseases, e.g., infectious diseases such as those caused by HIV infection (i.e., AIDS). Non-hematologic diseases associated with asparagine dependence include autoimmune diseases, for example rheumatoid arthritis, SLE, autoimmune, collagen vascular diseases, etc. Other autoimmune diseases include osteo-arthritis, Issac's syndrome, psoriasis, insulin dependent diabetes mellitus, multiple sclerosis, sclerosing panencephalitis, systemic lupus erythematosus, rheumatic fever, inflammatory bowel disease (e.g., ulcerative colitis and Crohn's disease), primary billiary cirrhosis, chronic active hepatitis, glomerulonephritis, myasthenia gravis, pemphigus vulgaris, and Graves' disease. Cells suspected of causing disease can be tested for asparagine dependence in any suitable in vitro or in vivo assay, e.g., an in vitro assay wherein the growth medium lacks asparagine.

The invention further relates to a method of treating a disease treatable by L-asparagine depletion in a patient, said method comprising administering to said patient an effective amount of the modified protein. In some preferred aspects, said disease treatable by L-asparagine depletion is Acute Lymphoblastic Leukemia (ALL), acute myeloid leukemia (AML) or non-Hodgkin's lymphoma. In some aspects, said disease treatable by L-asparagine depletion is a cancer including, but not limited to NK lymphoma, and pancreatic cancer. In additional embodiments, the modified protein described herein elicits a lower immunogenic response in said patient compared to the L-asparaginase of said modified protein.

In some aspects, the modified protein described above has a longer in vivo circulating half-life after a single dose compared to the unmodified L-asparaginase of said modified protein. The modified protein described herein can reduce plasma L-asparagine levels for a time period of at least about 12, 24, 48, 72, 96, or 120 hours when administered at a dose of 5 U/kg body weight (bw) or 10 µg/kg (protein content basis). The modified protein described herein can reduce plasma L-asparagine levels to undetectable levels for a time period of at least about 12, 24, 48, 72, 96, 120, or 144 hours when administered at a dose of 25 U/kg bw or 50 µg/kg (protein content basis). The modified protein described herein can reduce plasma L-asparagine levels for a time period of at least about 12, 24, 48, 72, 96, 120, 144, 168, 192, 216, or 240 hours when administered at a dose of 50 U/kg bw or 100 µg/kg (protein content basis). The modified protein described herein can reduce plasma L-asparagine levels to undetectable levels for a time period of at least about 12, 24, 48, 72, 96, 120, 144, 168, 192, 216, or 240 hours when administered at a dose ranging from about 10,000 to about 15,000 IU/m$^2$ (about 20-30 mg protein/m$^2$).

The modified protein described herein can result in a similar level of L-asparagine depletion over a period of time (e.g., 24, 48, or 72 hours) after a single dose.

The modified protein described herein can have a longer $t_{1/2}$ than the unmodified L-asparaginase administered at an equivalent protein dose. The modified protein described above can have a greater AUC value (e.g. at least 1.5, 2, 3, 4, 5, 6, 7, 8, 9 or 10 times) after a single dose compared to the L-asparaginase of said unmodified protein.

In some aspects the modified protein described herein does not raise any significant antibody response for a particular period of time after administration of a single dose, e.g, greater than about 1 week, 2 weeks, 3 weeks, 4, weeks, 5 weeks, 6 weeks, 7 weeks, 8 weeks, 9 weeks, 10 weeks, 11 weeks, 12 weeks, etc. For example, the modified protein does not raise any significant antibody response for at least 8 weeks. In one example, "does not raise any significant antibody response" means that the subject receiving the modified protein is identified within art-recognized parameters as antibody-negative. Antibody levels can be determined by methods known in the art, for example ELISA or surface plasmon resonance assays (Zalewska-Szewczyk (2009) Clin. Exp. Med. 9, 113-116; Avramis (2009) Anticancer Research 29, 299-302, each of which is incorporated herein by reference in its entirety). The modified protein may have any combination of these properties.

In some aspects, treatment with the modified protein described herein will be administered as a first line therapy. In another aspect, treatment with the modified protein will be administered as a second line therapy in patients, particularly patients with ALL, where objective signs of allergy or hypersensitivity, including "silent hypersensitivity," have developed to other asparaginase preparations, in particular, the native Escherichia coli-derived L-asparaginase or its PEGylated variant (pegaspargase). Non-limiting examples of objective signs of allergy or hypersensitivity include testing "antibody positive" for an asparaginase enzyme. In a specific aspect, the modified protein is used in second line therapy after treatment with pegaspargase. The patient may have had a previous hypersensitivity to an E. coli L-asparaginase, and/or may have had a previous hypersensitivity to an Erwinia L-asparaginase. The hypersensitivity may be selected from the group consisting of allergic reaction, anaphylactic shock, and silent hypersensitivity.

The incidence of relapse in ALL patients following treatment with L-asparaginase remains high, with approximately 10-25% of pediatric ALL patients having early relapse (e.g., some during maintenance phase at 30-36 months post-induction) (Avramis (2005) Clin. Pharmacokinet. 44, 367-393). If a patient treated with E. coli-derived L-asparaginase has a relapse, subsequent treatment with E. coli preparations could lead to a "vaccination" effect, whereby the E. coli preparation has increased immunogenicity during the subsequent administrations. The modified protein described herein may be used in a method of treating patients with relapsed ALL who were previously treated with other asparaginase preparations, in particular those who were previously treated with E. coli-derived asparaginases. The disease relapse may occur after treatment with an E. coli L-asparaginase or PEGylated form thereof.

In another aspect, the invention is directed to a method for treating acute lymphoblastic Leukemia comprising administering to a patient in need of the treatment a therapeutically effective amount of the modified protein described above. In a specific aspect, treatment will be administered at a dose ranging from about 1500 IU/m$^2$ to about 15,000 IU/m$^2$, typically about 10,000 to about 15,000 IU/m$^2$ (about 20-30 mg protein/m$^2$), at a schedule ranging from about twice a week to about once a month, typically once per week or once every other week. The modified protein described above may be administered as a single agent (e.g., monotherapy) or as a part of a combination of chemotherapy drugs, including, but not limited to glucocorticoids, corticosteroids, anticancer compounds or other agents, including, but not limited to methotrexate, dexamethasone, prednisone, prednisolone, vincristine, cyclophosphamide, and anthracycline. As an example, patients with ALL will be administered the modified protein described above as a component of multi-agent chemotherapy during 3 chemotherapy phases including induction, consolidation or intensification, and maintenance. In a specific example, the modified protein described above is not administered with an asparagine synthetase inhibitor (e.g., such as set forth in WO 2007/103290, which is herein incorporated by reference in its entirety). In another specific example, the modified protein described above is not administered with an asparagine synthetase inhibitor, but is administered with other chemotherapy drugs. The modified protein described above can be administered before, after, or simultaneously with other compounds as part of a multi-agent chemotherapy regimen.

In a specific embodiment, the method comprises administering the modified protein described above at an amount of about 1 U/kg to about 25 U/kg (e.g., about 1, 2, 3, 4, 5, 6, 7, 8, 9, 10, 11, 12, 13, 14, 15, 16, 17, 18, 19, 20, 21, 22, 23, 24, or 25 U/kg) or an equivalent amount thereof 20 (e.g., on a protein content basis). The amounts of the modified protein to be delivered will depend on many factors, for example, the IC$_{50}$, EC$_{50}$, the biological half-life of the compound, the age, size, weight, and physical condition of the patient, and the disease or disorder to be treated. The importance of these and other factors to be considered are well known to those of ordinary skill in the art. In certain embodiments, the amount of modified protein to be administered may range from about 10 International Units per square meter of the surface area of the patient's body (IU/m$^2$) to 50,000 IU/m$^2$. In additional aspects, the modified protein is administered at an amount selected from the group consisting of about 5, about 10, and about 25 U/kg. In another specific aspect, the modified protein is administered at a dose ranging from about 1,000 IU/m2 to about 20,000 IU/m2 (e.g., 1,000 IU/m$^2$, 2,000 IU/m$^2$, 3,000 IU/m$^2$, 4,000 IU/m$^2$, 5,000 IU/m$^2$, 6,000 IU/m$^2$, 7,000 IU/m$^2$, 8,000 IU/m$^2$, 9,000 IU/m$^2$, 10,000 IU/m$^2$, 11,000 IU/m$^2$, 25 12,000 IU/m$^2$, 13,000 IU/m$^2$, 14,000 IU/m$^2$, 15,000 IU/m$^2$, 16,000 IU/m$^2$, 17,000 IU/m$^2$, 18,000 IU/m$^2$, 19,000 IU/m$^2$, or 20,000 IU/m$^2$). In another specific aspect, the modified protein described above is administered at a dose that depletes L-asparagine to undetectable levels using methods and apparatus known in the art for a period of about 3 days to about 10 days (e.g., 3, 4, 5, 6, 7, 8, 9, or 10 days) for a single dose.

The modified protein may be administered in a dose that depletes L-asparagine to undetectable levels for a period of about 3 days to about 10 days, about 5 days to 20 days, about 1 day to 15 days, or about 2 day to 30 days. The modified protein may be administered in a dose that depletes L-asparagine to undetectable levels for a period of about 1, 2, 3, 4, 5, 6, 7, 8, 9, or 10 days to about 5, 6, 7, 8, 9, 10, 11, 12, 13, 14, 15, 16, 17, 18, 19 or 20 days. The modified protein may be administered intravenously or intramuscularly. In additional embodiments, said modified protein may be administered once or twice per week, less than once per week, or as monotherapy.

The present invention relates to a composition comprising the modified protein as defined herein or the modified protein prepared by the process as described herein. The composition may be a pharmaceutical composition, optionally further comprising (a) pharmaceutical acceptable carrier(s) or excipient(s).

The invention also relates to a pharmaceutical composition comprising the modified protein described above. In a specific aspect, the pharmaceutical composition is contained in a vial as a lyophilized powder to be reconstituted with a solvent, such as currently available native L-asparaginases, whatever the bacterial source used for its production (e.g. KIDROLASE, ELSPAR, ERWINASE). In another aspect, the pharmaceutical composition is a solution, such as pegaspargase (ONCASPAR) enabling, further to an appropriate handling, an administration through, e.g., intramuscular, intravenous (infusion and/or bolus), intra-cerebro-ventricular (icy), sub-cutaneous routes.

The modified protein, including compositions comprising the same (e.g., a pharmaceutical composition) can be administered to a patient using standard techniques. Techniques and formulations generally may be found in Remington's Pharmaceutical Sciences, 22nd ed., Pharmaceutical Press, (2012). Suitable dosage forms, in part, depend upon the use or the route of entry, for example, oral, transdermal, transmucosal, or by injection (parenteral). Such dosage forms should allow the therapeutic agent to reach a target cell or otherwise have the desired therapeutic effect. For example, pharmaceutical compositions injected into the blood stream preferably are soluble. The pharmaceutical compositions according to the invention can be formulated as pharmaceutically acceptable salts and complexes thereof. Pharmaceutically acceptable salts are non-toxic salts present in the amounts and concentrations at which they are administered. The preparation of such salts can facilitate pharmaceutical use by altering the physical characteristics of the compound without preventing it from exerting its physiological effect. Useful alterations in physical properties include lowering the melting point to facilitate transmucosal administration and increasing solubility to facilitate administering higher concentrations of the drug. The pharmaceutically acceptable salt of a modified protein as described herein may be present as a complex, as those in the art will appreciate. Pharmaceutically acceptable salts include acid addition salts such as those containing sulfate, hydrochloride, fumarate, maleate, phosphate, sulfamate, acetate, citrate, lactate, tartrate, methanesulfonate, ethanesulfonate, benzenesulfonate, p- to luenesulfonate, cyclohexylsulfamate, and quinate. Pharmaceutically acceptable salts can be obtained from acids, including hydrochloric acid, maleic acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, fumaric acid, and quinic acid. Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc, when acidic functional groups, such as carboxylic acid or phenol are present. For example, see Remington's Pharmaceutical Sciences, supra. Such salts can be prepared using the appropriate corresponding bases. Pharmaceutically acceptable carriers and/or excipients can also be incorporated into a pharmaceutical composition according to the invention to facilitate administration of the particular asparaginase. Examples of carriers suitable for use in the practice of the invention include calcium carbonate, calcium phosphate, various sugars such as lactose, glucose, or sucrose, or types of starch, cellulose derivatives, gelatin, vegetable oils, polyethylene glycols, and physiologically compatible solvents. Examples of physiologically compatible solvents include sterile solutions of water for injection (WFI), saline solution and dextrose. Pharmaceutical compositions according to the invention can be administered by different routes, including intravenous, intraperitoneal, subcutaneous, intramuscular, oral, topical (transdermal), or transmucosal administration. For systemic administration, oral administration is preferred. For oral administration, for example, the compounds can be formulated into conventional oral dosage forms such as capsules, tablets, and liquid preparations such as syrups, elixirs, and concentrated drops. Alternatively, injection (parenteral administration) may be used, e.g., intramuscular, intravenous, intraperitoneal, and subcutaneous injection. For injection, pharmaceutical compositions are formulated in liquid solutions, preferably in physiologically compatible buffers or solutions, such as saline solution, Hank's solution, or Ringer's solution. In addition, the compounds may be formulated in solid form and redissolved or suspended immediately prior to use. For example, lyophilized forms of the modified protein can be produced. In a specific aspect, the modified protein is administered intramuscularly. In preferred specific aspect, the modified protein is administered intravenously.

Systemic administration can also be accomplished by transmucosal or transdermal means. For transmucosal or transdermal administration, penetrants appropriate to the barrier to be permeated are used in the formulation. Such penetrants are well known in the art, and include, for example, for transmucosal administration, bile salts, and fusidic acid derivatives. In addition, detergents may be used to facilitate permeation. Transmucosal administration, for example, may be through nasal sprays, inhalers (for pulmonary delivery), rectal suppositories, or vaginal suppositories. For topical administration, compounds can be formulated into ointments, salves, gels, or creams, as is well known in the art.

In one aspect, the invention also relates to the use of the modified protein as described herein in therapy. The use may be for treating a disease treatable by L-asparagine depletion described above as a method of treating a disease treatable by L-asparagine depletion. In one aspect, the invention relates to the modified protein as described herein or the modified protein prepared by the process as described herein, or the composition comprising the modified protein as described herein, for use as a medicament/for use in therapy/for use in medicine.

In one aspect, the invention relates to the modified protein as described herein or the modified protein prepared by the process as described herein, or the composition comprising the modified protein as described herein, for use in the treatment of a disease treatable by L-asparagine depletion in a patient. The present invention also relates to the use of the modified protein as described herein or of the modified protein prepared by the process as described herein, or of the composition comprising the modified protein as described herein in the preparation of a medicament for treating a disease treatable by L-asparagine depletion in a patient, The present invention also relates to a method of treating a disease treatable by L-asparagine depletion in a patient, said method comprising administering to said patient an effective amount of the modified protein as described herein, the modified protein prepared by the process as described herein, or composition as described herein. Preferably, the disease treatable by L-asparagine depletion is a cancer.

In a preferred aspect, the invention relates to the modified protein as described herein or the modified protein prepared by the process as described herein, or the composition comprising the modified protein as described herein for use in the treatment of cancer. The present invention also relates to the use of the modified protein as described herein or of the modified protein prepared by the process as described herein, or of the composition comprising the modified protein as described herein in the preparation of a medicament for treating cancer. The present invention also relates to a method for treating cancer comprising the administration of the modified protein described herein, the modified protein prepared by the process described herein, or the composition described herein, to a subject.

It is preferred herein that the subject to be treated is a mammal, particularly a human The cancer may be a non-solid cancer, e.g. is leukemia or non-Hodgkin's lymphoma. Preferably, said leukemia is acute lymphoblastic leukemia (ALL) or acute myeloid leukemia (AML).

The modified protein may elicit a lower immunogenic response in the patient compared to the unconjugated L-asparaginase. The modified protein may have a longer in vivo circulating half-life after a single dose compared to the unconjugated L-asparaginase. The modified protein can have a greater AUC value after a single dose compared to the unconjugated L-asparaginase. The patient may have had a previous hypersensitivity to an *E. coli* L-asparaginase or PEGylated form thereof.

The following examples illustrate exemplary embodiments of the invention:

EXAMPLE 1: Optimization of Coupling Ratio for the Preparation of Pyroglutamoyl-P/A(20)-Aminohexanoyl-Crisantaspase 4.38 mg Pga-P/A#1(20)-Ahx peptide (Part A of FIG. 1; TFA salt, purity 98%; PSL Peptide Specialty Laboratories, Heidelberg, Germany) (SEQ ID NO: 16, amino acid sequence shown in SEQ ID NO: 5) was dissolved in 66.3 µl DMSO. The chemical activation of the P/A peptide via its terminal carboxylate group was started by addition of 23.7 µL of a solution of 500 mM TBTU (CAS#125700-67-6; Iris Biotech, Marktredwitz, Germany) in DMSO and 2.7 µL DIPEA to the peptide solution and vortexing (cf. Part C of FIG. 1). In this setup, the concentration of the peptide was 25.8 mM and the molar ratio between DIPEA, TBTU and Pga-P/A#1(20)-Ahx was 5:5:1. After 10 min incubation at 25° C. the mixture was diluted in Eppendorf tubes according to Table 1.

A solution of *Dickeya chrysanthemi* L-Asparaginase (Crisantaspase, SEQ ID NO: 1, recombinant, produced in *E. coli* (lot RE-LAP-P57D) with a concentration of 2 mg/mL was prepared in phosphate-buffered saline (PBS: 115 mM NaCl, 4 mM $KH_2PO_4$ and 16 mM $Na_2HPO_4$, pH 7.4) and pipetted into each Eppendorf tube according to the volumes stated in table 1. After mixing by repeated pipetting and vortexing, the coupling reaction was allowed to take place at 25° C. for 30 min. The reaction was quenched by addition of glycine (pH 8.0 adjusted with Tris base) to a final concentration of 250 mM.

TABLE 1

Dilution series of activated P/A peptide for coupling with Asparaginase

| Mass ratio | Peptide stock solution [µL] | DMSO [µL] | Asparaginase [µL] |
|---|---|---|---|
| 10x | 21 | 0 | 50 |
| 7.5x | 21 | 7 | 66.7 |
| 5x | 21 | 21 | 100 |
| 3.5x | 21 | 39 | 143 |

SDS-PAGE analysis of the modified proteins is shown in FIG. 2. The individual bands correspond to protein modified proteins varying by one coupled P/A peptide each. The additional application of a mix of coupling reactions with ratios of 0.3 to 10 mg peptide per mg protein allowed counting of the bands in a successive ladder starting from the unconjugated protein and thus the number of coupled P/A peptides could be precisely determined. The band intensities were quantified densitometrically using the Quant v12.2 software (TotalLab, Newcastle upon Tyne, UK) and arithmetic mean values of the number of coupled peptides per Crisantaspase monomer weighted for their band intensities were calculated (cf. Table 2). 3.5 mg P/A peptide per mg Crisantaspase resulted in a coupling ratio in the range of 9 to 12 P/A peptides per Crisantaspase monomer (mean value: 10.4). Increasing the applied mass ratio to 10 mg P/A peptide per mg Crisantaspase led only to a slight increase of the resulting coupling ratio of 10 to 13 P/A peptides per Crisantaspase (mean value 12.0), indicating a saturation of accessible amino groups.

The modified proteins were purified by anion exchange chromatography (AEX) on a MonoQ HR5/5 column (GE Healthcare) using 25 mM Na-borate pH 9.0, 1 mM EDTA as running buffer and a NaCl concentration gradient from 0 to 1 M to elute the proteins. L-asparaginase aminohydrolase activity of each Crisantaspase modified protein was determined by reaction of ammonia that is liberated via L-asparagine enzymatic activity with the Nessler reagent. Briefly, 50 µL of enzyme solution was mixed with 20 mM of L-asparagine in a 100 mM sodium borate buffer pH 8.6 containing 0.015% (w/v) bovine serum albumin and incubated for 15 min at 37° C. The reaction was stopped by addition of 200 µL of Nessler reagent (Sigma-Aldrich). Absorbance of this solution was measured at 450 nm. The activity was calculated from a calibration curve that was obtained from ammonium sulphate as reference. The results are summarized in Table 2.

TABLE 2

Enzymatic activities of Crisantaspase conjugated with Pga-P/A(20)-Ahx peptide in different amounts

| mg PA peptide/ mg Crisantaspase | mol PA peptide/ mol monomer | Specific activity [U/mg] | Rel. activity [%] |
|---|---|---|---|
| 0 | — | 540 ± 32 | 100 |
| 3.5 | 10.4 | 508 ± 20 | 94.1 |
| 5 | 11.2 | 436 ± 22 | 80.7 |
| 7.5 | 11.7 | 401 ± 21 | 74.3 |
| 10 | 12.0 | 256 ± 20 | 47.4 |

EXAMPLE 2: Preparation of Pyroglutamoyl-P/A(40)-Aminohexanoyl-Crisantaspase 28 mg of the Pyroglutamoyl-P/A#1(40)-Ahx peptide (SEQ ID NO. 17, amino acid sequence shown in SEQ ID NO: 15), Part B of FIG. 1, TFA salt, purity 98%; Almac Group, Craigavon, UK) was dissolved in 1324 µL of anhydrous DMSO (99.9%; Sigma-Aldrich, Taufkirchen, Germany). To achieve chemical activation of the P/A peptide via its terminal carboxylate group, 162 µL of a solution of 500 mM TBTU (CAS#125700-67-6; Iris Biotech, Marktredwitz, Germany) in DMSO and, after mixing, 14 µL DIPEA (99.5%, biotech. Grade, Sigma-Aldrich) were added. The whole mixture was vortexed briefly and incubated for 20 min at 25° C. (cf. Part C of FIG. 1). In this setup, the peptide concentration was 5.41 mM and the molar ratio between DIPEA, TBTU and Pga-P/A#1(40)-Ahx was 10:10:1.

3.5 mL of an ice-cold Crisantaspase solution (SEQ ID NO: 1)(2 mg/mL in PBS) was mixed with the activated peptide solution (1.5 mL), resulting in a mass ratio between Pga-P/A#1(40)-Ahx and Crisantaspase of 5:1, and incubated at room temperature for 30 min to allow coupling. Using a regenerated cellulose membrane dialysis tube (MWCO 50 kDa, Spectrum Laboratories, Los Angeles, Calif.), the solution was dialyzed against 5 L AEX running buffer (25 mM Na-borate pH 9.0, 1 mM EDTA) and subjected to anion exchange chromatography on a HISCALE 16/40 column packed with SOURCE 15Q resin (GE Healthcare). The column was equilibrated with AEX running buffer and the protein modified protein was eluted using a segmented NaCl concentration gradient from 0 to 150 mM in 1 column volume and from 150 to 1000 mM in 0.25 column volumes (Part A of FIG. 3).

Applying the eluate to SDS-PAGE alongside a ladder obtained from a mix of coupling reactions with ratios of 0.3 to 10 mg peptide per mg protein allowed determination of the coupling ratio of 9-11 PA peptides per Crisantaspase monomer (mean value: 10.0) (Part B of FIG. 3). Enzyme activity of the Crisantaspase/PA(40) modified protein determined using the Nessler assay described in example 1 was 78.2% of the activity of the equally assayed non-modified Crisantaspase.

EXAMPLE 3: Preparation of Pyroglutamoyl-P/A(20)-Aminohexanoyl-Crisantaspase 21 mg of the Pyroglutamoyl-P/A#1(20)-Ahx peptide (SEQ ID NO: 5, Part A of FIG. 1; TFA salt, purity 98%; PSL Peptide Specialty Laboratories, Heidelberg, Germany) was dissolved in 1376 µL of anhydrous DMSO (99.9%; Sigma-Aldrich, Taufkirchen, Germany). To achieve chemical activation of the P/A peptide via its terminal carboxylate group, 114 µL of a solution of 500 mM TBTU (CAS#125700-67-6; purchased from Iris Biotech, Marktredwitz, Germany) in DMSO and, after mixing, 10 µL DIPEA (99.5%, biotech. Grade, Sigma-Aldrich) were added. The whole mixture was vortexed briefly and incubated for 20 min at 25° C. (Part C of FIG. 1). In this setup, the peptide concentration was 7.58 mM and the molar ratio between DIPEA, TBTU and Pga-P/A#1(20)-Ahx was 5:5:1.

3.5 mL of an ice-cold Crisantaspase solution (SEQ ID NO: 1)(2 mg/mL in PBS) was mixed with the activated peptide solution (1.5 mL), resulting in a mass ratio between Pga-P/A#1(40)-Ahx and Crisantaspase of 5:1, and incubated at room temperature for 30 min to allow coupling. Using a regenerated cellulose membrane dialysis tube (MWCO 50 kDa, Spectrum Laboratories, Los Angeles, Calif.), the solution was dialyzed against 5 L AEX running buffer (25 mM Na-borate pH 9.0, 1 mM EDTA) and subjected to anion exchange chromatography on a HISCALE 16/40 column packed with SOURCE 15Q resin (GE Healthcare). The column was equilibrated with AEX running buffer and the protein modified protein was eluted using a segmented NaCl concentration gradient from 0 to 150 mM in 1 column volume and from 150 to 1000 mM in 0.25 column volumes (Part A of FIG. 4).

Applying the eluate to SDS-PAGE alongside a ladder obtained from a mix of coupling reactions with ratios of 0.3 to 10 mg peptide per mg protein, allowed determination of the coupling ratio of 10-13 PA peptides per Crisantaspase monomer (mean value 11.9) (Part B of FIG. 4). Enzyme activity of the Crisantaspase/PA(20) modified protein determined using the Nessler assay described in Example 1 was 91.2% of the activity of the equally assayed non-modified Crisantaspase.

EXAMPLE 4: Cloning of Expression Plasmids for the Periplasmic Production of Crisantaspase N-Terminally Fused to P/A Sequences of Varying Length A synthetic DNA fragment encoding the mature amino acid sequence of *Dickeya chrysanthemi* L-asparaginase (UniProt ID P06608) was obtained from a gene synthesis provider (Thermo Fisher Scientific, Regensburg, Germany). This gene fragment (SEQ ID NO: 4) comprised an XbaI restriction site, followed by a ribosomal binding site, the nucleotide sequence encoding the Enx signal peptide, followed by a GCC alanine codon, a first SapI recognition sequence GCTCTTC on the non-coding strand, an 11-nucleotide spacer, and a second SapI restriction sequence in reverse complementary orientation, with its recognition sequence GCTCTTC on the coding strand, followed by a GCC alanine codon directly linked to the coding sequence for mature L-asparaginase, which was finally followed by a HindIII restriction site.

This gene fragment was cloned on pASk75 via the flanking restriction sites XL and HindIII according to standard procedures (Sambrook (2012) Molecular Cloning: A Laboratory Manual, Cold Spring Harbor Laboratory Press). The resulting plasmid (Part A of FIG. 5) was digested with SapI, which led to the liberation of a small (30 bp) DNA insert containing both SapI recognition sites and a cleaved vector backbone with compatible 5'-GCC/5'-GGC sticky ends at the position directly in front of the encoded mature N-terminus of L-asparaginase, which is ideally suited for insertion of the low repetitive nucleic acid molecule encoding the proline/alanine-rich amino acid repeat sequence. After isolation of the vector fragment using the Promega Wizard gel extraction kit (Promega, Mannheim, Germany) and dephosphorylation with the thermosensitive alkaline phosphatase FastAP (Thermo Fisher Scientific, Waltham, Mass.), both according to the manufacturer's instructions, it was ligated with the PA#1b(200) gene cassette excised from pXL2-PA#1b(200) (SEQ ID NO: 8) or PA#1c/1b(400) gene cassette excised from pXL2-PA#1c/1b(400) (SEQ ID NO: 10) via EarI restriction digest. The resulting plasmids (SEQ ID NO: 12 and SEQ ID NO: 14)(Part B of FIG. 5) allow the bacterial expression of fusion proteins (SEQ ID NO: 11 and SEQ ID NO: 13) consisting of a proline/alanine-rich amino acid repeat sequence fused with the biologically active protein Crisantaspase (after in vivo processing of the Enx signal peptide upon periplasmic secretion in *E. coli*).

EXAMPLE 5: Bacterial Production and Purification of Fusion Proteins Between Either the PA#1(200) or the PA#1(400) Sequence and Crisantaspase Both, the PA#1(200)-Crisantaspase and the PA#1(400)-Crisantaspase fusion protein (calculated mass: 51 kDa and 67 kDa, respectively) were produced at 25° C. in *E. coli* W3110 harboring the expression plasmid pASK75-PA200-Crisantaspase or pASK75-PA400-Crisantaspase (Part B of FIG. 5) from Example 4 using an 8 L bench top fermenter with a synthetic glucose mineral medium supplemented with 100 mg/L ampicillin according to a published procedure (Schiweck (1995) Proteins 23: 561-565). Recombinant gene expression was induced by addition of 500 μg/L anhydrotetracycline (Skerra (1994) loc. cit.) as soon as the culture reached $OD_{550}=40$. After an induction period of 2.5 h, cells were harvested by centrifugation and resuspended during 10 min in ice-cold periplasmic fractionation buffer (500 mM sucrose, 1 mM EDTA, 200 mM boric acid/NaOH pH 8.0; 2 ml per L and $OD_{550}$). After adding 15 mM EDTA and 250 μg/mL lysozyme, the cell suspension was incubated for 20 min on ice, centrifuged several times, and the cleared supernatant containing the recombinant protein was recovered.

The periplasmic extracts were dialyzed twice at 4° C. against 15 L PBS containing 1 mM EDTA for at least 6 h, respectively, filtered using a 0.2 μm cellulose nitrate membrane (GE Healthcare) and precipitated by addition of ammonium sulfate (Ph. Eur. grade; Applichem, Darmstadt, Germany) to a saturation of 25% at 25° C. After centrifugation, the supernatant was removed and the sediment was resuspended in AEX running buffer (25 mM Na-borate pH 9.0, 1 mM EDTA) and dialyzed at 4° C. against 5L AEX running buffer for at least 6 h. The dialyzed protein solution was cleared from remaining insoluble matter by centrifugation and subjected to subtractive anion exchange chromatography using a 85 ml HISCALE column (GE Healthcare, Freiburg, Germany) packed with Source15Q resin, connected to an AKTA purifier system (GE Healthcare, Freiburg, Germany), equilibrated in AEX running buffer. The column flow-through containing the pure protein (cf. Part A of FIG. 6 and Part B of FIG. 6) was dialyzed twice against 5 L PBS.

Homogeneous protein preparations without signs of aggregation were obtained with a final yield of 128 mg for PA#1(200)-Crisantaspase and 48 mg for PA#1(400)-Crisantaspase from one 8 L fermenter, respectively. Protein concentrations were determined by measuring the absorption at 280 nm using a calculated extinction coefficient (Gill (1989) *Anal. Biochem.* 182: 319-326) of 19370 $M^{-1}$ $cm^{-1}$. Enzyme activities of the fusion proteins were determined using the Nessler assay described in example 1. In this setup, the PA#1(200)-Crisantaspase fusion protein had 109% and the PA#1(400)-Crisantaspase had 118% of enzyme activity compared to the equally assayed non-modified Crisantaspase. This demonstrates that the N-terminal fusion of Crisantaspase with P/A polypeptides to the length of at least 401 amino acids does not affect enzymatic activity.

EXAMPLE 6: Measurement of the Hydrodynamic Volume for Both Genetically and Chemically PASylated Crisantaspase by Analytical Gel Filtration Size exclusion chromatography (SEC) was carried out on a SUPERDEX 5200 increase 10/300 GL column (GE Healthcare Europe, Freiburg, Germany) at a flow rate of 0.5 mL/min using an AKTA Purifier 10 system (GE Healthcare) with PBS (115 mM NaCl, 4 mM $KH_2PO_4$, 16 mM $Na_2HPO_4$; pH 7.4) as running buffer. Using regenerated cellulose disposable ultrafiltration devices (MWCO 10 kDa; Merck-Millipore, Darmstadt, Germany) recombinant Crisantaspase genetically fused with PA#1(200) or PA#1(400)

polypeptides (described in Example 5) and Crisantaspase chemically conjugated with either the Pga-P/A(40)-Ahx peptide (described in Example 2) or with the Pga-P/A(20)-Ahx peptide (described in Example 3) were adjusted to a concentration of 1 mg/mL in PBS. 150 µL samples of the concentrated PASylated enzymes and of non-PASylated Crisantaspase were individually applied to the column and the chromatography traces were overlaid (Part A of FIG. 7). All five proteins eluted in single homogenous peaks.

For column calibration (Part B of FIG. 7) 150 µL of an appropriate mixture of the following globular proteins (Sigma, Deisenhofen, Germany) was applied in PBS at protein concentrations between 0.5 mg/ml and 1.0 mg/ml: cytochrome c, 12.4 kDa; ovalbumin, 43.0 kDa; bovine serum albumin, 66.3 kDa; alcohol dehydrogenase, 150 kDa; β-amylase, 200 kDa; apo-ferritin, 440 kDa; thyroglobulin, 660 kDa.

As result, both the recombinant PA fusion proteins and the chemically conjugated enzyme preparations exhibited a significantly larger size than corresponding globular proteins with the same molecular weight. With increasing size of the P/A (poly-)peptide moiety this mol. weight/hydrodynamic volume disproportion increased further. The apparent size increase for PA(200)-Crisantaspase was 5.1-fold compared with the unfused Crisantaspase whereas the true mass was only larger by 1.5-fold. The apparent size increase for PA(400)-Crisantaspase compared with the unfused Crisantaspase was 10.4-fold whereas the true mass was only larger by 1.9-fold. This observation clearly indicates a much increased hydrodynamic volume conferred to the biologically active Crisantaspase enzyme by the Pro/Ala polypeptide segment according to this invention.

EXAMPLE 7: ESI-MS Analysis of Chemically or Genetically PASylated Crisantaspase

250 µl of the purified chemical modified protein of Crisantaspase with Pga-P/A(20)-Ahx from Example 3 and of the recombinant PA200- and PA400-fusion proteins from Example 5, all at a concentration of 1 mg/mL, were applied to a 1 mL Resource™ RPC column (GE Healthcare, Freiburg, Germany) connected to an AKTA purifier system using 2% v/v acetonitrile, 1% v/v formic acid as running buffer. The proteins were eluted using an acetonitrile gradient from 2% v/v acetonitrile, 1% v/v formic acid to 80% v/v acetonitrile, 0.1% v/v formic acid over 20 column volumes. The eluted proteins were directly analyzed via ESI mass spectrometry on a MAXIS micrOTOF instrument (Bruker Daltonik, Bremen, Germany) using the positive ion mode. The raw m/z spectrum of the Crisantaspase/Pga-P/A(20)-Ahx chemical modified protein is shown in Part A of FIG. 8. The masses revealed by the deconvoluted mass spectrum (Part B of FIG. 8) are given in Table 3. The distribution of masses matches the coupling ratios determined by SDS-PAGE analysis described in Example 2.

The raw m/z spectrum of the recombinant PA#1(200)-Crisantaspase (SEQ ID NO: 11) fusion protein is shown in Part C of FIG. 8. The deconvoluted mass spectrum revealed a mass of 51164.75 Da (Part D of FIG. 8), which essentially coincides with the calculated mass of this protein (51163.58 Da). The raw m/z spectrum of the recombinant PA#1(400)-Crisantaspase fusion protein (SEQ ID NO: 13) is shown in Part E of FIG. 8. The deconvoluted spectrum (Part F of FIG. 8) revealed a mass of 67199.17 Da, which essentially coincides with the calculated mass of this protein (67201.99 Da). This clearly demonstrates that intact Crisantaspase enzyme genetically fused to either PA200 or PA400 can be produced in E. coli in a highly homogeneous form.

TABLE 3

Comparison of calculated and measured masses detected in the preparation of the Crisantaspase/Pga-P/A(20)-Ahx chemical modified protein

| Coupling ratio | Calculated mass | Measured mass |
| --- | --- | --- |
| 9x | 51506.1 | 51503.9 |
| 10x | 53334.1 | 53333.2 |
| 11x | 55162.1 | 55161.7 |
| 12x | 56990.1 | 56990.1 |
| 13x | 58818.1 | 58819.4 |
| 14x | 60646.1 | 60645.8 |

EXAMPLE 8: Asparaginase Activity

PASylated L-asparaginase enzyme activity was determined by catalysis of the conversion of L-asparagine into L-aspartic acid. This reaction liberates one mole of ammonia per mole of converted L-asparagine. The released ammonia is detected using Nessler's reagent. In the presence of Nessler's reagent the ammonia will form a water-soluble yellow complex that can be quantified by absorbance measurement at 450 nm (Mashburn et al. (1963) Biochem. Biophys. Res. Commun. 12, 50). One unit of L-asparaginase enzyme activity (International Unit or IU) is defined as the amount of enzyme that catalyzes the conversion of one µmol of L-asparagine per minute. The specific activity of the samples (IU/mg) is determined by dividing the value of L-asparaginase activity expressed in IU/mL by the protein concentration expressed in mg/mL. The mass of the protein monomer with the PASylated sequence was measured.

The measurement of L-asparaginase activity is based on an endpoint assay in which the sample is diluted to a series of final enzyme concentrations which are then incubated at 37° C. under saturating L-asparagine concentration for 15 minutes. The reaction is stopped by addition of Nessler's reagent and the amount of ammonia produced by the reaction is extrapolated from a calibration curve constructed from known quantities of ammonium sulfate used as standard. A plot of enzyme concentration versus ammonia is then created for each sample and the slope of the curve divided by the reaction time to obtain the specific activity in IU/mg. Specific activity is reported as IU/mg and is reported to the nearest whole number.

The initial testing results are displayed in the table below for each of the modified proteins or fusion proteins.

| Crisantaspase Expression System | Modified protein Type | Nessler Plate 1 (IU/mg) | Nessler Plate 2 (IU/mg) | Nessler Plate 3 (IU/mg) | Nessler (Average) |
| --- | --- | --- | --- | --- | --- |
| E. coli | PA200-Crisantaspase | 626 | 666 | 556 | 616 |
| E. coli | Crisantaspase-P/A(20)n | 694 | 732 | 602 | 676 |
| E. coli | PA400-Crisantaspase | 790 | 748 | 699 | 746 |
| E. coli | Crisantaspase-P/A(40)n | 567 | 528 | 490 | 528 |

EXAMPLE 9: Pharmacokinetics

The pharmacokinetic profile of E. coli expressed recombinant crisantaspase as a PASylated fusion protein (PA-200)

or chemically conjugated to PA-peptides (PA-20) was characterized following administration of a single intravenous bolus dose to CD-1 mice. The CD-1 mice is a model for a healthy mouse.

All animals received a single intravenous (IV) bolus via the lateral tail vein (10 mL/kg) based on the body weight taken prior to dosing. Individual doses were calculated based upon the most recent individual body weights to provide the proper dose. The first day of dosing was based on study day 0 body weights. All animals were observed for mortality, abnormalities, and signs of pain and distress twice daily, once in the morning and once in the afternoon.

PASylated asparaginase was administered as a single IV dose of 25 IU/kg body weight to mice. Groups of mice were dosed at 25 IU/kg body weight and plasma samples were collected at scheduled times for up to 10 days (240 h) following dosing. Asparaginase activity in mouse plasma was measured using a qualified biochemical assay as described in the previous examples. Mean plasma asparaginase activity (n=4) versus time data are plotted (FIG. 1) and pharmacokinetic analyses were conducted.

Blood samples were taken prior to dosing and at approximately 6, 24 (Day 1), 48 (Day 2), 51 (Day 2), 54 (Day 2), 60 (Day 2), 96 (Day 4), 168 (Day 7), and 240 (Day 10) hours post dose. Tail-snip (cut end of tail) blood collection procedure was employed. Approximately 1 to 2 mm was cut off the distal end of the tail for the first blood collection, all sequential blood collections were collected from the same site by removing the scab and facilitating blood flow by stroking the tail. Approximately 100 µL blood per time point was collected into chilled $K_3$EDTA (Minivette) sampling tubes. Blood was transferred into tubes appropriate for centrifugation. For plasma isolation, all samples were centrifuged within approximately 20 minutes of sampling at 3,000×g in a refrigerated centrifuge set to maintain approximately 4° C. for approximately 10 minutes. Following centrifugation, the maximum amount of plasma was recovered (targeting 30 µL) and placed into plastic vials. The plastic vials were stored at –65° C. to –85° C. until testing.

Asparaginase activity was measured as the concentration of asparaginase in the plasma samples as previously described (Alias et al. (2009) Blood, 114, 2033). Parameters dependent on sufficient characterization of the terminal phase of the concentration versus time profile ($t_{1/2}$, CL, and $V_{ss}$) were only reported if $R^2$ (the square of the correlation coefficient for linear regression used to estimate the terminal elimination rate constant, λz) was greater than 0.8. The pharmacokinetic data was imported into Phoenix WinNonlin v6.4 (Certara/Pharsight) for analysis. The plasma asparaginase activity versus time data were analyzed using non-compartmental methods with sparse sampling in an IV bolus administration model. Activity values below the limit of quantitation of the assay (10 U/L) were set to zero in the calculation of group means. Nominal dose levels and sample collection times were used for the calculations. The estimated t1/2 values were 50.2 h for PA-20 crisantaspase and 17.9 h for PA-200 crisantaspase.

The present invention refers to the following nucleotide and amino acid sequences:

Some sequences provided herein are available in the NCBI database and can be retrieved from ncbi.nlm.nih.gov/sites/entrez?db=gene; Theses sequences also relate to annotated and modified sequences. The present invention also provides techniques and methods wherein homologous sequences, and variants of the concise sequences provided herein are used. Preferably, such "variants" are genetic variants.

SEQ ID NO: 1:
Amino acid sequence of *Dickeya chrysanthemi* L-Asparaginase.

ADKLPNIVILATGGTIAGSAATGTQTTGYKAGALGVDTLINAVPEVKKLA

NVKGEQFSNMASENMTGDVVLKLSQRVNELLARDDVDGVVITHGTDTVEE

SAYFLHLTVKSDKPVVFVAAMRPATAISADGPMNLLEAVRVAGDKQSRGR

GVMVVLNDRIGSARYITKTNASTLDTFKANEEGYLGVIIGNRIYYQNRID

KLHTTRSVFDVRGLTSLPKVDILYGYQDDPEYLYDAAIQHGVKGIVYAGM

GAGSVSVRGIAGMRKAMEKGVVVIRSTRTGNGIVPPDEELPGLVSDSLNP

AHARILLMLALTRTSDPKVIQEYFHTY

SEQ ID NO: 2:
Nucleotide sequence encoding *Dickeya chrysanthemi* L-Asparaginase

GCAGATAAACTGCCGAATATTGTTATTCTGGCAACCGGTGGCACCATTGC

AGGTAGCGCAGCAACCGGCACCCAAACCACAGGTTATAAAGCCGGTGCAC

TGGGTGTTGATACCCTGATTAATGCAGTTCCGGAAGTTAAAAAACTGGCC

AATGTGAAAGGTGAACAGTTTAGCAATATGGCCAGCGAAAATATGACCGG

TGATGTTGTTCTGAAACTGAGCCAGCGTGTTAATGAACTGCTGGCACGTG

ATGATGTTGATGGTGTGGTTATTACCCATGGCACCGATACCGTTGAAGAA

AGCGCCTATTTTCTGCATCTGACCGTGAAAAGCGATAAACCGGTTGTTTT

TGTTGCAGCAATGCGTCCGGCAACCGCAATTAGCGCAGATGGTCCGATGA

ATCTGCTGGAAGCAGTTCGTGTTGCCGGTGATAAACAGAGCCGTGGTCGT

GGTGTTATGGTTGTTCTGAATGATCGTATTGGTAGCGCACGCTATATTAC

CAAAACCAATGCAAGCACCCTGGATACCTTTAAAGCCAATGAAGAAGGTT

ATCTGGGCGTTATTATTGGCAATCGCATTTATTATCAGAATCGCATTGAT

AAACTGCATACCACCCGTAGCGTTTTTGATGTTCGTGGTCTGACCAGCCT

GCCGAAAGTTGATATTCTGTATGGCTATCAGGATGATCCGGAATATCTGT

ATGATGCAGCCATTCAGCATGGTGTTAAAGGTATTGTGTATGCAGGTATG

GGTGCAGGTAGCGTTAGCGTTCGTGGTATTGCAGGTATGCGTAAAGCAAT

GGAAAAAGGCGTTGTTGTTATTCGTAGCACCCGTACCGGTAATGGTATTG

TTCCGCCGGATGAAGAACTGCCGGGTCTGGTTAGCGATAGCCTGAATCCG

GCACATGCACGTATTCTGCTGATGCTGGCACTGACCCGTACCAGCGATCC

GAAAGTGATTCAGGAATATTTTCATACCTAT

SEQ ID NO: 3:
Amino acid sequence of *Dickeya chrysanthemi* L-Asparaginase
Signal peptide: 1-28; removed during cloning: 29-39; 40-366 asparaginase

MKFKKNFLVGLSAALMSISLFSATASAARRAIVGRSSAADKLPNIVILA

TGGTIAGSAATGTQTTGYKAGALGVDTLINAVPEVKKLANVKGEQFSNMA

SENMTGDVVLKLSQRVNELLARDDVDGVVITHGTDTVEESAYFLHLTVKS

DKPVVFVAAMRPATAISADGPMNLLEAVRVAGDKQSRGRGVMVVLNDRIG

-continued

SARYITKTNASTLDTFKANEEGYLGVIIGNRIYYQNRIDKLHTTRSVFDV

RGLTSLPKVDILYGYQDDPEYLYDAAIQHGVKGIVYAGMGAGSVSVRGIA

GMRKAMEKGVVVIRSTRTGNGIVPPDEELPGLVSDSLNPAHARILLMLAL

TRTSDPKVIQEYFHTY

SEQ ID NO: 4
Nucleotide sequence (synthetic) encoding *Dickeya chrysanthemi* L-Asparaginase
mature asparaginase coded from base 160-1140 (bold letters). Thus, a nucleotide sequence encoding L-Asparaginase ranges from nucleotides at position 160 to 1140.

TCTAGAAATAATTTTGTTTAACTTTAAGAAGGAGATATACATATGTTCAA

ATTCAAAAAAAACTTCCTGGTGGGTCTGAGCGCAGCACTGATGAGCATTA

GCCTGTTTAGCGCAACCGCAAGCGCAGCCAGAAGAGCGATTGTAGGACGC

TCTTCTGCCGCAGATAAACTGCCGAATATTGTTATTCTGGCAACCGGTGG

CACCATTGCAGGTAGCGCAGCAACCGGCACCCAGACCACCGGTTATAAAG

CCGGTGCACTGGGTGTTGATACCCTGATTAATGCAGTTCCGGAAGTTAAA

AAACTGGCCAATGTTAAAGGTGAGCAGTTTAGCAATATGGCCAGCGAAAA

TATGACCGGTGATGTTGTTCTGAAACTGAGCCAGCGTGTTAATGAACTGC

TGGCACGTGATGATGTTGATGGTGTTGTTATTACCCATGGCACCGATACC

GTTGAAGAAAGCGCATATTTTCTGCATCTGACCGTGAAAAGCGATAAACC

GGTTGTTTTTGTTGCAGCAATGCGTCCGGCAACCGCCATTAGCGCAGATG

GTCCGATGAATCTGCTGGAAGCAGTTCGTGTTGCCGGTGATAAACAGAGC

CGTGGTCGTGGTGTTATGGTTGTGCTGAATGATCGTATTGGTAGCGCACG

TTATATTACCAAAACCAATGCAAGCACCCTGGATACCTTTAAAGCAAATG

AAGAAGGTTATCTGGGCGTCATTATTGGCAATCGTATCTATTATCAGAAC

CGCATCGACAAACTGCATACCACCCGTAGCGTTTTTGATGTTCGTGGTCT

GACCAGCCTGCCGAAAGTGGATATTCTGTATGGTTATCAGGATGATCCGG

AATATCTGTATGATGCAGCAATTCAGCATGGTGTGAAAGGTATTGTTTAT

GCAGGTATGGGTGCGGGTAGCGTTAGCGTTCGTGGTATTGCCGGTATCGCG

TAAAGCAATGGAAAAAGGTGTTGTTGTGATTCGTAGCACCCGTACCGGTA

ATGGTATTGTTCCGCCTGATGAAGAACTGCCTGGTCTGGTTAGCGATAGC

CTGAATCCGGCACATGCACGTATTCTGCTGATGCTGGCACTGACCCGTAC

CAGCGATCCGAAAGTTATTCAAGAATATTTTCATACCTATAAGCTT

SEQ ID NO: 5:
Amino acid sequence of PA(20) peptide

AAPAAPAPAAPAAPAPAAPA

SEQ ID NO: 6:
Nucleotide sequence encoding PA(20) peptide

GCCGCGCCAGCGGCCCCGGCCCCTGCCGCGCCCGCTGCTCCCGCCCCTGC

TGCCCCAGCC

SEQ ID NO: 7:
Amino acid sequence of PA(200)-polypeptide

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

A

SEQ ID NO: 8:
Nucleotide sequence encoding PA(200)-polypeptide

GCCGCGCCAGCGGCCCCGGCCCCTGCCGCGCCCGCTGCTCCCGCCCCTGC

TGCCCCAGCCGCCGCTCCTGCGGCACCTGCGCCCGCCGCGCCGGCAGCGC

CGGCACCGGCAGCTCCGGCGGCCGCGCCTGCAGCTCCTGCACCGGCGGCT

CCAGCAGCCCCGGCGCCGGCCGCACCTGCGGCGGCGCCCGCGGCGCCTGC

ACCCGCAGCGCCTGCGGCACCGGCCCCAGCAGCCCCTGCCGCCGCACCGG

CTGCGCCTGCCCCAGCGGCCCCCGCTGCCCCGGCCCCGGCGGCTCCAGCC

GCAGCGCCTGCCGCCCCAGCGCCCGCAGCACCGGCGGCACCAGCTCCGGC

GGCGCCGGCGGCGGCTCCGGCAGCTCCGGCCCCTGCTGCGCCGGCTGCGC

CGGCTCCGGCGGCCCCTGCGGCGGCTCCGGCCGCACCTGCACCTGCCGCG

CCGGCTGCTCCGGCCCCGGCTGCCCCAGCAGCGGCACCAGCAGCGCCTGC

TCCTGCGGCGCCTGCAGCTCCGGCGCCGGCAGCCCCGGCCGCCGCACCCG

CGGCTCCAGCCCCGCCGCTCCAGCAGCCCCGCGCCAGCTGCACCTGCT

GCC

SEQ ID NO: 9:
Amino acid sequence of PA(400)-polypeptide

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

A

SEQ ID NO: 10:
Nucleotide sequence encoding PA(400)-polypeptide

GCCGCGCCAGCGGCCCCGGCCCCTGCCGCGCCCGCTGCTCCCGCCCCTGC

TGCCCCAGCCGCCGCTCCTGCGGCACCTGCGCCCGCCGCGCCGGCAGCGC

CGGCACCGGCAGCTCCGGCGGCCGCGCCTGCAGCTCCTGCACCGGCGGCT

CCAGCAGCCCCGGCGCCGGCCGCACCTGCGGCGGCGCCCGCGGCGCCTGC

ACCCGCAGCGCCTGCGGCACCGGCCCCAGCAGCCCCTGCCGCCGCACCGG

-continued

CTGCGCCTGCCCCAGCGGCCCCCGCTGCCCCGGCCCCGGCGGCTCCAGCC

GCAGCGCCTGCCGCCCCAGCGCCCGCAGCACCGGCGGCACCAGCTCCGGC

GGCGCCGGCGGCGGCTCCGGCAGCTCCGGCCCCTGCTGCGCCGGCTGCGC

CGGCTCCGGCGGCCCCTGCGGCGGCTCCGGCCGCACCTGCACCTGCCGCG

CCGGCTGCTCCGGCCCCGGCTGCCCCAGCAGCGGCACCAGCAGCGCCTGC

TCCTGCGGCGCCTGCAGCTCCGGCGCCGGCAGCCCCGGCCGCCGCACCCG

CGGCTCCAGCCCCGCCGCTCCAGCAGCCCCGCGCCAGCTGCACCTGCT

GCCGCTCCTGCTGCCCCTGCTCCCGCTGCCCCGCCGCCCCGCCCCAGC

TGCCCCGCTGCCGCACCTGCTGCCCCAGCTCCCGCTGCCCCAGCCGCGC

CGGCCCCCGCAGCTCCAGCCGCGGCACCAGCTGCCCCAGCTCCAGCGGCG

CCTGCTGCCCGGCCCCGCGGCACCGGCTGCCGCGCCCGCAGCTCCAGC

GCCTGCTGCACCGGCTGCTCCGGCACCCGCCGCGCCAGCAGCTGCCCCTG

CGGCACCAGCTCCTGCTGCCCCGCGGCACCTGCACCCGCTGCCCCGGCG

GCAGCTCCCGCCGCGCCAGCCCCTGCAGCTCCTGCTGCACCTGCTCCTGC

CGCCCCTGCTGCTGCCCCTGCTGCTCCAGCCCCTGCAGCACCGGCCGCTC

CAGCTCCTGCCGCTCCTGCCGCTGCGCCCGCTGCTCCAGCCCCAGCTGCG

CCAGCAGCTCCTGCACCTGCTGCCCCTGCCGCCGCCCCTGCGGCTCCAGC

ACCTGCTGCACCGGCCGCCCGGCGCCCGCTGCCCCGCAGCAGCCCAG

CCGCACCCGCTCCAGCAGCTCCCGCAGCCCCAGCACCCGCAGCACCAGCC

GCC

SEQ ID NO: 11:
Amino acid sequence of Asparaginase-PA(200)-fusion protein

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AADKLPNIVILATGGTIAGSAATGTVQTTGYKAGALGVDTLINAVPEVKKL

ANVKGEQFSNMASENMTGDVVLKLSQRVNELLARDDVDGVVITHGTDTVE

ESAYFLHLTVKSDKPVVFVAAMRPATAISADGPMNLLEAVRVAGDKQSRG

RGVMVVLNDRIGSARYITKTNASTLDTFKANEEGYLGVIIGNRIYYQNRI

DKLHTTRSVFDVRGLTSLPKVDILYGYQDDPEYLYDAAIQHGVKGIVYAG

MGAGSVSVRGIAGMRKAMEKGVVVIRSTRTGNGIVPPDEELPGLVSDSLN

PAHARILLMLALTRTSDPKVIQEYFHTY

SEQ ID NO: 12:
Nucleotide sequence encoding Asparaginase-PA(200)-fusion protein (XbaI/HindIII)
Mature fusion protein (SEQ ID NO: 11) coded from base 127-1710 (bold letters). Thus, a nucleotide sequence encoding a fusion protein can range from nucleotides at position 127 to 1710 of SEQ ID NO: 12. Accordingly, the term "modified protein comprising or consisting of an amino acid sequence encoded by a nucleic acid having a nucleotide sequence as shown in SEQ ID NO: 12" as used herein can be more narrowly defined as "modified protein comprising or consisting of an amino acid sequence encoded by a nucleic acid having a nucleotide sequence as shown in positions 127 to 1710 of SEQ ID NO: 12".

TCTAGAAATAATTTTGTTTAACTTTAAGAAGGAGATATACATATGTTCAA

ATTCAAAAAAAACTTCCTGGTGGGTCTGAGCGCAGCACTGATGAGCATTA

GCCTGTTTAGCGCAACCGCAAGCGCAGCCGCGCCAGCGGCCCCGGCCCCT

GCCGCGCCCGCTGCTCCCGCCCCTGCTGCCCCAGCCGCCGCTCCTGCGGC

ACCTGCGCCCGCCGCCGGCAGCGCCGGCACCGGCAGCTCCGGCGGCCG

CGCCTGCAGCTCCTGCACCGGCGGCTCCAGCAGCCCCGGCGCCGGCCGCA

CCTGCGGCGGCGCCCGCGGCGCCTGCACCCGCAGCGCCTGCGGCACCGGC

CCCAGCAGCCCCTGCCGCCGCACCGGCTGCGCCTGCCCCAGCGGCCCCCG

CTGCCCCGGCCCCGGCGGCTCCAGCCGCAGCGCCTGCCGCCCCAGCGCCC

GCAGCACCGGCGGCACCAGCTCCGGCGGCGCCGGCGGCGGCTCCGGCAGC

TCCGGCCCCTGCTGCGCCGGCTGCGCCGGCTCCGGCGGCCCCTGCGGCGG

CTCCGGCCGCACCTGCACCTGCCGCGCCGGCTGCTCCGGCCCCGGCTGCC

CCAGCAGCGGCACCAGCAGCGCCTGCTCCTGCGGCGCCTGCAGCTCCGGC

GCCGGCAGCCCCGGCCGCCGCACCCGCGGCTCCAGCCCCGCCGCTCCAG

CAGCCCCGCGCCAGCTGCACCTGCTGCCGCAGATAAACTGCCGAATATT

GTTATTCTGGCAACCGGTGGCACCATTGCAGGTAGCGCAGCAACCGGCAC

CCAGACCACCGGTTATAAAGCCGGTGCACTGGGTGTTGATACCCTGATTA

ATGCAGTTCCGGAAGTTAAAAAACTGGCCAATGTTAAAGGTGAGCAGTTT

AGCAATATGGCCAGCGAAAATATGACCGGTGATGTTGTTCTGAAACTGAG

CCAGCGTGTTAATGAACTGCTGGCACGTGATGATGTTGATGGTGTTGTTA

TTACCCATGGCACCGATACCGTTGAAGAAAGCGCATATTTTCTGCATCTG

ACCGTGAAAAGCGATAAACCGGTTGTTTTTGTTGCAGCAATGCGTCCGGC

AACCGCCATTAGCGCAGATGGTCCGATGAATCTGCTGGAAGCAGTTCGTG

TTGCCGGTGATAAACAGAGCCGTGGTCGTGGTGTTATGGTTGTGCTGAAT

GATCGTATTGGTAGCGCACGTTATATTACCAAAACCAATGCAAGCACCCT

GGATACCTTTAAAGCAAATGAAGAAGGTTATCTGGGCGTCATTATTGGCA

ATCGTATCTATTATCAGAACCGCATCGACAAACTGCATACCACCCGTAGC

GTTTTTGATGTTCGTGGTCTGACCAGCCTGCCGAAAGTGGATATTCTGTA

TGGTTATCAGGATGATCCGGAATATCTGTATGATGCAGCAATTCAGCATG

GTGTGAAAGGTATTGTTTATGCAGGTATGGGTGCGGGTAGCGTTAGCGTT

CGTGGTATTGCCGGTATGCGTAAAGCAATGGAAAAAGGTGTTGTTGTGAT

TCGTAGCACCCGTACCGGTAATGGTATTGTTCCGCCTGATGAAGAACTGC

CTGGTCTGGTTAGCGATAGCCTGAATCCGGCACATGCACGTATTCTGCTG

ATGCTGGCACTGACCCGTACCAGCGATCCGAAAGTTATTCAAGAATATTT

TCATACCTATTAAGCTT

SEQ ID NO: 13:
Amino acid sequence of Asparaginase-PA(400)-fusion protein

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AAPAAPAPAAPAAPAPAAPAAAPAAPAPAAPAAPAPAAPAAAPAAPAPAA

PAAPAPAAPAAAPAAPAPAAPAAPAPAAPAAAPAAPAPAAPAAPAPAAPA

AADKLPNIVILATGGTIAGSAATGTQTTGYKAGALGVDTLINAVPEVKKL

ANVKGEQFSNMASENMTGDVVLKLSQRVNELLARDDVDGVVITHGTDTVE

ESAYFLHLTVKSDKPVVFVAAMRPATAISADGPMNLLEAVRVAGDKQSRG

RGVMVVLNDRIGSARYITKTNASTLDTFKANEEGYLGVIIGNRIYYQNRI

DKLHTTRSVFDVRGLTSLPKVDILYGYQDDPEYLYDAAIQHGVKGIVYAG

MGAGSVSVRGIAGMRKAMEKGVVVIRSTRTGNGIVPPDEELPGLVSDSLN

PAHARILLMLALTRTSDPKVIQEYFHTY

SEQ ID NO: 14:
Nucleotide sequence encoding Asparaginase-PA(400)-fusion protein
(XbaI/HindIII)
Mature fusion protein (SEQ ID NO: 13) coded from base 127-2184 (bold letters). Thus, a nucleotide sequence encoding a fusion protein can range from nucleotides at position 127 to 2184 of SEQ ID NO: 14. Accordingly, the term "modified protein comprising or consisting of an amino acid sequence encoded by a nucleic acid having a nucleotide sequence as shown in SEQ ID NO: 14" as used herein can be more narrowly defined as "modified protein comprising or consisting of an amino acid sequence encoded by a nucleic acid having a nucleotide sequence as shown in positions 127 to 2184 of SEQ ID NO: 14".

TCTAGAAATAATTTTGTTTAACTTTAAGAAGGAGATATACATATGTTCAA

ATTCAAAAAAAACTTCCTGGTGGGTCTGAGCGCAGCACTGATGAGCATTA

GCCTGTTTAGCGCAACCGCAAGCGCAGCCGCGCCAGCGGCCCCGGCCCCT

GCCGCGCCCGCTGCTCCCGCCCCTGCTGCCCCAGCCGCCGCTCCTGCGGC

ACCTGCGCCCGCCGCCGGCAGCGCCGGCACCGGCAGCTCCGGCGGCCG

CGCCTGCAGCTCCTGCACCGGCGGCTCCAGCAGCCCGGCGCCGGCCGCA

CCTGCGGCGGCGCCCGCGGCGCCTGCACCCGCAGCGCCTGCGGCACCGGC

CCCAGCAGCCCTGCCGCCGCACCGGCTGCGCCTGCCCAGCGGCCCCCG

CTGCCCCGGCCCCGGCGGCTCCAGCCGCAGCGCCTGCCGCCCCAGCGCCC

GCAGCACCGGCGGCACCAGCTCCGGCGGCGCCGGCGGCGGCTCCGGCAGC

TCCGGCCCCTGCTGCGCCGGCTGCGCCGGCTCCGGCGGCCCCTGCGGCGG

CTCCGGCCGCACCTGCACCTGCCGCGCCGGCTGCTCCGGCCCCGGCTGCC

CCAGCAGCGGCACCAGCAGCGCCTGCTCCTGCGGCGCCTGCAGCTCCGGC

GCCGGCAGCCCCGGCCGCCGCACCCGCGGCTCCAGCCCCCGCCGCTCCAG

CAGCCCCCGCCAGCTGCACCTGCTGCCGCTCCTGCTGCCCCTGCTCCC

GCTGCCCCCGCCGCCCCGCCCCAGCTGCCCCCGCTGCCGCACCTGCTGC

CCCAGCTCCCGCTGCCCCAGCCGCGCCGGCCCCCGCAGCTCCAGCCGCGG

CACCAGCTGCCCCAGCTCCAGCGGCGCCTGCTGCCCCGGCCCCGCGGCA

CCGGCTGCCGCGCCCGCAGCTCCAGCGCCTGCTGCACCGGCTGCTCCGGC

ACCCGCCGCGCCAGCAGCTGCCCCTGCGGCACCAGCTCCTGCTGCCCCCG

CGGCACCTGCACCCGCTGCCCCGGCGGCAGCTCCCGCCGCGCCAGCCCCT

GCAGCTCCTGCTGCACCTGCTCCTGCCGCCCCTGCTGCTGCCCCTGCTGC

TCCAGCCCTGCAGCACCGGCCGCTCCAGCTCCTGCCGCTCCTGCCGCTG

CGCCCGCTGCTCCAGCCCAGCTGCGCCAGCAGCTCCTGCACCTGCTGCC

CCTGCCGCCGCCCCTGCGGCTCCAGCACCTGCTGCACCGGCCGCCCCGGC

GCCCGCTGCCCCCGCAGCAGCCCCAGCCGCACCCGCTCCAGCAGCTCCCG

CAGCCCCAGCACCCGCAGCACCAGCCGCCGCAGATAAACTGCCGAATATT

GTTATTCTGGCAACCGGTGGCACCATTGCAGGTAGCGCAGCAACCGGCAC

CCAGACCACCGGTTATAAAGCCGGTGCACTGGGTGTTGATACCCTGATTA

ATGCAGTTCCGGAAGTTAAAAAACTGGCCAATGTTAAAGGTGAGCAGTTT

AGCAATATGGCCAGCGAAAATATGACCGGTGATGTTGTTCTGAAACTGAG

CCAGCGTGTTAATGAACTGCTGGCACGTGATGATGTTGATGGTGTTGTTA

TTACCCATGGCACCGATACCGTTGAAGAAAGCGCATATTTTCTGCATCTG

ACCGTGAAAAGCGATAAACCGGTTGTTTTTGTTGCAGCAATGCGTCCGGC

AACCGCCATTAGCGACAGATGGTCCGATGAATCTGCTGGAAGCAGTTCGTG

TTGCCGGTGATAAACAGAGCCGTGGTCGTGGTGTTATGGTTGTGCTGAAT

GATCGTATTGGTAGCGCACGTTATATTACCAAAACCAATGCAAGCACCCT

GGATACCTTTAAAGCAAATGAAGAAGGTTATCTGGGCGTCATTATTGGCA

ATCGTATCTATTATCAGAACCGCATCGACAAACTGCATACCACCCGTAGC

GTTTTTGATGTTCGTGGTCTGACCAGCCTGCCGAAAGTGGATATTCTGTA

TGGTTATCAGGATGATCCGGAATATCTGTATGATGCAGCAATTCAGCATG

GTGTGAAAGGTATTGTTTATGCAGGTATGGGTGCGGGTAGCGTTAGCGTT

CGTGGTATTGCCGGTATGCGTAAAGCAATGGAAAAAGGTGTTGTTGTGAT

TCGTAGCACCCGTACCGGTAATGGTATTGTTCCGCCTGATGAAGAACTGC

CTGGTCTGGTTAGCGATAGCCTGAATCCGGCACATGCACGTATTCTGCTG

ATGCTGGCACTGACCCGTACCAGCGATCCGAAAGTTATTCAAGAATATTT

TCATACCTATTAAGCTT

SEQ ID NO: 15: Amino acid sequence of PA(40) peptide

AAPAAPAPAAPAAPAPAAPAAAPAAPAPAAPAAPAPAAPA

SEQ ID NO: 16: Modified PA(20) peptide

Pga-AAPAAPAPAAPAAPAPAAPA-Ahx-COOH

SEQ ID NO: 17: Modified PA(40) peptide

```
Pga-AAPAAPAPAAPAAPAPAAPAAAPAAPAPAAPAAPAPAAPA-
Ahx-COOH
```

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

The invention claimed is:

1. A modified fusion protein comprising
   (i) an L-asparaginase comprising the amino acid sequence of SEQ ID NO: 1, and
   (ii) one or more polypeptides, wherein the one or more polypeptides comprise the amino acid sequence of SEQ ID NO: 7 or 9.

2. The modified fusion protein according to claim 1, wherein the L-asparaginase consists of the amino acid sequence of SEQ ID NO: 1.

3. The modified fusion protein according to claim 1, wherein the modified protein is a fusion protein of the L-asparaginase and the one or more polypeptides.

4. The modified fusion protein according to claim 3, wherein the one or more polypeptides consist of 200 to 600 proline and alanine amino acid residues.

5. The modified fusion protein according to claim 3, wherein the one or more polypeptides consist of 200 to 400 proline and alanine amino acid residues, and the proline amino acid residues constitute more than 10% and less than 70% of the polypeptide.

6. The modified fusion protein according to claim 3, wherein at least one of the one or more polypeptides comprises the amino acid sequence of SEQ ID NO: 7.

7. The modified fusion protein according to claim 3, wherein at least one of the one or more polypeptides comprises the amino acid sequence of SEQ ID NO: 9.

8. The modified fusion protein according to claim 3, wherein the fusion protein comprises the amino acid sequence of SEQ ID NO: 11.

9. The modified fusion protein according to claim 3, wherein the fusion protein comprises the amino acid sequence of SEQ ID NO: 13.

10. The modified fusion protein according to claim 3, wherein the L-asparaginase comprises the amino acid sequence of SEQ ID NO: 1 and the polypeptide consists of the amino acid sequence of SEQ ID NO: 7, or 9.

11. The modified fusion protein according to claim 2, wherein at least one of the one or more polypeptides consists of the amino acid sequence of SEQ ID NO: 7.

12. The modified fusion protein according to claim 2, wherein at least one of the one or more polypeptides consists of the amino acid sequence of SEQ ID NO: 9.

13. The modified fusion protein according to claim 3, wherein the L-asparaginase is composed of four subunits.

14. The modified fusion protein according to claim 3, wherein the fusion protein consists of the amino acid sequence of SEQ ID NO: 11 or 13.

15. A pharmaceutical composition comprising the modified fusion protein according to claim 1 and one or more pharmaceutical acceptable carriers or excipients.

16. The pharmaceutical composition of claim 15, wherein the one or more polypeptides is present in an amount sufficient to mediate a decreased immunogenicity of the modified protein following administration to a human subject.

17. The pharmaceutical composition of claim 15, wherein the one or more polypeptides is present in an amount sufficient to increase the plasma half-life of the L-asparaginase following administration to a human subject.

* * * * *